United States Patent
Gu et al.

(10) Patent No.: US 9,688,812 B2
(45) Date of Patent: *Jun. 27, 2017

(54) POLYMERS FOR FUNCTIONAL PARTICLES

(71) Applicants: Massachusetts Institute of Technology, Cambridge, MA (US); The Brigham and Women's Hospital, Inc., Boston, MA (US)

(72) Inventors: Frank X. Gu, Waterloo (CA); Omid C. Farokhzad, Waban, MA (US); Robert S. Langer, Newton, MA (US); Benjamin A. Teply, Omaha, NE (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/621,551

(22) Filed: Feb. 13, 2015

(65) Prior Publication Data

US 2015/0157737 A1 Jun. 11, 2015

Related U.S. Application Data

(60) Continuation of application No. 13/673,354, filed on Nov. 9, 2012, now Pat. No. 9,080,014, which is a
(Continued)

(51) Int. Cl.
*A61K 9/51* (2006.01)
*C08G 63/91* (2006.01)
(Continued)

(52) U.S. Cl.
CPC .......... *C08G 63/912* (2013.01); *A61K 9/5153* (2013.01); *A61K 47/482* (2013.01);
(Continued)

(58) Field of Classification Search
None
See application file for complete search history.

(56) References Cited

U.S. PATENT DOCUMENTS 3,766,774 A 10/1973 Clark
4,270,537 A 6/1981 Romaine
(Continued)

FOREIGN PATENT DOCUMENTS

CA 2453959 1/2003
CA 2649149 A1 10/2007
(Continued)

OTHER PUBLICATIONS

Abad, et al., "Comparison of a Monoclonal Antibody-Based Enzyme-Linked Immunosorbent Assay and Gas Chromatography for the Determination of Nicotine in Cigarette Smoke Condensates", Anal. Chem., 65:3227-3231 (1993).
(Continued)

*Primary Examiner* — Isaac Shomer
(74) *Attorney, Agent, or Firm* — Pabst Patent Group LLP

(57) ABSTRACT

A method includes producing libraries of nanoparticles having highly controlled properties, which can be formed by mixing together two or more macromolecules in different ratios. One or more of the macromolecules may be a polymeric conjugate of a moiety to a biocompatible polymer. The nanoparticle may contain a drug. The moiety may include a polypeptide or a polynucleotide, such as an aptamer. The moiety may be a targeting moiety, an imaging moiety, a chelating moiety, a charged moiety, or a therapeutic moiety. Another aspect is directed to systems and methods of producing such polymeric conjugates. In some embodiments, a solution containing a polymer is contacted with a liquid, such as an immiscible liquid, to form nanoparticles containing the polymeric conjugate. Other methods use such libraries, use or administer such polymeric conju-
(Continued)

gates, or promote the use of such polymeric conjugates. Kits involving such polymeric conjugates are also described.

12 Claims, 19 Drawing Sheets

Related U.S. Application Data division of application No. 12/873,692, filed on Sep. 1, 2010, now Pat. No. 8,323,698, which is a division of application No. 11/803,843, filed on May 15, 2007, now Pat. No. 8,367,113.

(60) Provisional application No. 60/747,240, filed on May 15, 2006.

(51) Int. Cl.
    *A61K 47/48*     (2006.01)
    *A61K 51/12*     (2006.01)
    *B82Y 5/00*     (2011.01)
    *A61K 49/00*     (2006.01)

(52) U.S. Cl.
CPC .. *A61K 47/48092* (2013.01); *A61K 47/48215* (2013.01); *A61K 47/48246* (2013.01); *A61K 47/48907* (2013.01); *A61K 47/48915* (2013.01); *A61K 49/00* (2013.01); *A61K 51/1244* (2013.01); *B82Y 5/00* (2013.01); *Y10S 977/773* (2013.01); *Y10S 977/906* (2013.01); *Y10S 977/915* (2013.01); *Y10T 428/2982* (2015.01)

(56) References Cited

U.S. PATENT DOCUMENTS

| | | | |
|---|---|---|---|
| 4,446,122 A | 5/1984 | Chu | |
| 4,596,556 A | 6/1986 | Morrow | |
| 4,631,211 A | 12/1986 | Houghten | |
| 4,638,045 A | 1/1987 | Kohn | |
| 4,790,824 A | 12/1988 | Morrow | |
| 4,806,621 A | 2/1989 | Kohn | |
| 4,862,851 A | 9/1989 | Washino | |
| 4,886,499 A | 12/1989 | Cirelli | |
| 4,902,615 A | 2/1990 | Freeman | |
| 4,940,460 A | 7/1990 | Casey | |
| 4,941,880 A | 7/1990 | Burns | |
| 4,946,929 A | 8/1990 | DAmore | |
| RE33,405 E | 10/1990 | Chu | |
| 4,970,299 A | 11/1990 | Bazinet | |
| 5,010,167 A | 4/1991 | Ron | |
| 5,015,235 A | 5/1991 | Crossman | |
| 5,019,379 A | 5/1991 | Domb | |
| 5,055,404 A | 10/1991 | Ueda | |
| 5,064,413 A | 11/1991 | McKinnon | |
| 5,093,246 A | 3/1992 | Cech | |
| 5,118,528 A | 6/1992 | Fessi | |
| 5,141,496 A | 8/1992 | Dalto | |
| 5,162,504 A | 11/1992 | Horoszewicz | |
| 5,175,296 A | 12/1992 | Gerster | |
| 5,190,521 A | 3/1993 | Hubbard | |
| 5,270,163 A | 12/1993 | Gold | |
| 5,312,335 A | 5/1994 | McKinnon | |
| 5,328,483 A | 7/1994 | Jacoby | |
| 5,334,144 A | 8/1994 | Alchas | |
| 5,334,497 A | 8/1994 | Inaba | |
| 5,339,163 A | 8/1994 | Homma | |
| 5,342,781 A | 8/1994 | Su | |
| 5,383,851 A | 1/1995 | McKinnon | |
| 5,389,640 A | 2/1995 | Gerster | |
| 5,399,665 A | 3/1995 | Barrera | |
| 5,417,662 A | 5/1995 | Hjertman | |
| 5,466,220 A | 11/1995 | Brenneman | |
| 5,472,704 A | 12/1995 | Santus | |
| 5,480,381 A | 1/1996 | Weston | |
| 5,500,161 A | 3/1996 | Andrianov | |
| 5,503,627 A | 4/1996 | McKinnon | |
| 5,512,600 A | 4/1996 | Mikos | |
| 5,514,378 A | 5/1996 | Mikos | |
| 5,520,639 A | 5/1996 | Peterson | |
| 5,527,288 A | 6/1996 | Gross | |
| 5,543,158 A * | 8/1996 | Gref | A61K 9/0019 424/451 |
| 5,567,588 A | 10/1996 | Gold | |
| 5,569,189 A | 10/1996 | Parsons | |
| 5,578,325 A | 11/1996 | Domb | |
| 5,595,877 A | 1/1997 | Gold | |
| 5,599,302 A | 2/1997 | Lilley | |
| 5,649,912 A | 7/1997 | Peterson | |
| 5,660,985 A | 8/1997 | Pieken | |
| 5,696,175 A | 12/1997 | Mikos | |
| 5,696,249 A | 12/1997 | Gold | |
| 5,704,911 A | 1/1998 | Parsons | |
| 5,716,404 A | 2/1998 | Vacanti | |
| 5,733,925 A | 3/1998 | Kunz | |
| 5,736,372 A | 4/1998 | Vacanti | |
| 5,763,177 A | 6/1998 | Gold | |
| 5,766,635 A | 6/1998 | Spenleuhauer | |
| 5,770,417 A | 6/1998 | Vacanti | |
| 5,786,204 A | 7/1998 | He | |
| 5,789,163 A | 8/1998 | Drolet | |
| 5,804,178 A | 9/1998 | Vacanti | |
| 5,817,785 A | 10/1998 | Gold | |
| 5,820,879 A | 10/1998 | Fernandez | |
| 5,837,752 A | 11/1998 | Shastri | |
| 5,843,653 A | 12/1998 | Gold | |
| 5,843,732 A | 12/1998 | Davis | |
| 5,853,984 A | 12/1998 | Davis | |
| 5,869,103 A | 2/1999 | Yeh | |
| 5,871,747 A | 2/1999 | GengouxSedlik | |
| 5,874,218 A | 2/1999 | Drolet | |
| 5,876,727 A | 3/1999 | Swain | |
| 5,893,397 A | 4/1999 | Peterson | |
| 5,898,031 A | 4/1999 | Crooke | |
| 5,902,599 A | 5/1999 | Anseth | |
| 5,916,539 A | 6/1999 | Pilgrimm | |
| 5,928,647 A | 7/1999 | Rock | |
| 5,942,252 A | 8/1999 | Tice | |
| 5,958,691 A | 9/1999 | Pieken | |
| 5,977,089 A | 11/1999 | Arimilli | |
| 5,993,412 A | 11/1999 | Deily | |
| 6,001,577 A | 12/1999 | Gold | |
| 6,005,087 A | 12/1999 | Cook | |
| 6,007,845 A * | 12/1999 | Domb | A61K 9/5153 424/451 |
| 6,030,613 A | 2/2000 | Blumberg | |
| 6,031,086 A | 2/2000 | Switzer | |
| 6,039,969 A | 3/2000 | Tomai | |
| 6,043,224 A | 3/2000 | Lee | |
| 6,083,505 A | 7/2000 | Miller | |
| 6,095,148 A | 8/2000 | Shastri | |
| 6,107,094 A | 8/2000 | Crooke | |
| 6,110,462 A | 8/2000 | Barbas | |
| 6,120,666 A | 9/2000 | Jacobson | |
| 6,123,727 A | 9/2000 | Vacanti | |
| 6,127,533 A | 10/2000 | Cook | |
| 6,184,364 B1 | 2/2001 | Pieken | |
| 6,190,913 B1 | 2/2001 | Singh | |
| 6,225,460 B1 | 5/2001 | Jones | |
| 6,232,082 B1 | 5/2001 | Ennifar | |
| 6,238,705 B1 | 5/2001 | Liu | |
| 6,242,246 B1 | 6/2001 | Gold | |
| 6,245,776 B1 | 6/2001 | Skwierczynski | |
| 6,254,890 B1 | 7/2001 | Hirosue | |
| 6,288,040 B1 | 9/2001 | Muller | |
| 6,291,673 B1 | 9/2001 | Fuchs | |
| 6,344,318 B1 | 2/2002 | Gold | |
| 6,348,462 B1 | 2/2002 | Gerster | |
| 6,365,187 B2 | 4/2002 | Mathiowitz | |
| 6,376,190 B1 | 4/2002 | Gold | |
| 6,399,754 B1 | 6/2002 | Cook | |
| 6,403,779 B1 | 6/2002 | Kawasaki | |

(56) References Cited

U.S. PATENT DOCUMENTS

| | | |
|---|---|---|
| 6,429,200 B1 | 8/2002 | Monahan |
| 6,451,527 B1 | 9/2002 | Larocca |
| 6,458,539 B1 | 10/2002 | Gold |
| 6,458,543 B1 | 10/2002 | Gold |
| 6,482,594 B2 | 11/2002 | Gold |
| 6,492,554 B2 | 12/2002 | Dalton |
| 6,506,559 B1 | 1/2003 | Fire |
| 6,506,577 B1 | 1/2003 | Deming |
| 6,558,951 B1 | 5/2003 | Tomai |
| 6,569,896 B2 | 5/2003 | Dalton |
| 6,589,562 B1 | 7/2003 | Shefer |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming |
| 6,656,469 B1 | 12/2003 | Svensson |
| 6,686,446 B2 | 2/2004 | Deming |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming |
| 6,838,484 B2 | 1/2005 | Steiner |
| 6,875,605 B1 | 4/2005 | Ma |
| 6,932,971 B2 | 8/2005 | Bachmann |
| 6,995,284 B2 | 2/2006 | Dalton |
| 6,998,500 B2 | 2/2006 | Dalton |
| 7,008,411 B1 | 3/2006 | Mandrusov |
| 7,022,870 B2 | 4/2006 | Dalton |
| 7,026,500 B2 | 4/2006 | Dalton |
| 7,029,859 B2 | 4/2006 | Thompson |
| 7,030,228 B1 | 4/2006 | Schmitz |
| 7,056,704 B2 | 6/2006 | Tuschl |
| 7,078,196 B2 | 7/2006 | Tuschl |
| 7,097,837 B2 | 8/2006 | Nielsen |
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |
| 7,427,629 B2 | 9/2008 | Kedl |
| 7,488,792 B2 | 2/2009 | Ruoslahti |
| 7,550,441 B2 | 6/2009 | Farokhzad |
| 7,727,969 B2 | 6/2010 | Farokhzad |
| 7,767,803 B2 | 8/2010 | Diener |
| 9,080,014 B2 * | 7/2015 | Gu .................... A61K 9/5153 |
| 2001/0012890 A1 | 8/2001 | Thompson |
| 2002/0009466 A1 | 1/2002 | Brayden |
| 2002/0064780 A1 | 5/2002 | Gold |
| 2002/0068091 A1 | 6/2002 | Davis |
| 2002/0086356 A1 | 7/2002 | Tuschl |
| 2002/0094542 A1 | 7/2002 | Leskovar |
| 2002/0099036 A1 | 7/2002 | Dalton |
| 2002/0099096 A1 | 7/2002 | Dalton |
| 2002/0102613 A1 | 8/2002 | Hoogenboom |
| 2002/0106647 A1 | 8/2002 | Segal |
| 2002/0116054 A1 | 8/2002 | Lundell |
| 2002/0150578 A1 | 10/2002 | He |
| 2002/0151004 A1 | 10/2002 | Craig |
| 2002/0153251 A1 | 10/2002 | Sassi |
| 2002/0156125 A1 | 10/2002 | Broder |
| 2002/0173495 A1 | 11/2002 | Dalton |
| 2003/0003103 A1 | 1/2003 | Thompson |
| 2003/0003114 A1 | 1/2003 | Pan |
| 2003/0009029 A1 | 1/2003 | Buchholz |
| 2003/0022868 A1 | 1/2003 | Dalton |
| 2003/0035804 A1 | 2/2003 | D' Amico |
| 2003/0054360 A1 | 3/2003 | Gold |
| 2003/0087301 A1 | 5/2003 | Smith |
| 2003/0099668 A1 | 5/2003 | Bachmann |
| 2003/0108611 A1 | 6/2003 | Bosch |
| 2003/0108923 A1 | 6/2003 | Tuschl |
| 2003/0133988 A1 | 7/2003 | Fearon |
| 2003/0134810 A1 | 7/2003 | Springate |
| 2003/0138557 A1 | 7/2003 | Allison |
| 2003/0162761 A1 | 8/2003 | Steiner |
| 2003/0165478 A1 | 9/2003 | Sokoll |
| 2003/0175950 A1 | 9/2003 | McSwiggen |
| 2003/0219766 A1 | 11/2003 | Raitano |
| 2003/0225040 A1 | 12/2003 | Dalton |
| 2003/0232013 A1 | 12/2003 | Sieckman |
| 2003/0232792 A1 | 12/2003 | Dalton |
| 2003/0235619 A1 | 12/2003 | Allen |
| 2004/0014789 A1 | 1/2004 | Lau |
| 2004/0014975 A1 | 1/2004 | Dalton |
| 2004/0022727 A1 | 2/2004 | Stanton |
| 2004/0022840 A1 | 2/2004 | Nagy |
| 2004/0029913 A1 | 2/2004 | Dalton |
| 2004/0043923 A1 | 3/2004 | Parma |
| 2004/0052727 A1 | 3/2004 | Dalton |
| 2004/0059094 A1 | 3/2004 | Bachmann |
| 2004/0067196 A1 | 4/2004 | Brunke |
| 2004/0067503 A1 | 4/2004 | Tan |
| 2004/0067979 A1 | 4/2004 | Dalton |
| 2004/0072234 A1 | 4/2004 | Parma |
| 2004/0087810 A1 | 5/2004 | Dalton |
| 2004/0092470 A1 | 5/2004 | Leonard |
| 2004/0136961 A1 | 7/2004 | Prokop |
| 2004/0141958 A1 | 7/2004 | Steinaa |
| 2004/0147489 A1 | 7/2004 | Dalton |
| 2004/0147550 A1 | 7/2004 | Dalton |
| 2004/0156846 A1 | 8/2004 | Daum |
| 2004/0167103 A1 | 8/2004 | Dalton |
| 2004/0192626 A1 | 9/2004 | McSwiggen |
| 2004/0241790 A1 | 12/2004 | Eriksen |
| 2004/0247680 A1 | 12/2004 | Farokhzad |
| 2004/0248088 A1 | 12/2004 | Raitano |
| 2004/0260092 A1 | 12/2004 | Miller |
| 2004/0260108 A1 | 12/2004 | Dalton |
| 2004/0266688 A1 | 12/2004 | Nayak |
| 2005/0017667 A1 | 1/2005 | Yamamoto |
| 2005/0019870 A1 | 1/2005 | Afar |
| 2005/0019872 A1 | 1/2005 | Afar |
| 2005/0020525 A1 | 1/2005 | McSwiggen |
| 2005/0032733 A1 | 2/2005 | McSwiggen |
| 2005/0033074 A1 | 2/2005 | Dalton |
| 2005/0037075 A1 * | 2/2005 | Farokhzad ....... A61K 47/48192 424/468 |
| 2005/0048063 A1 | 3/2005 | Ruoslahti |
| 2005/0069910 A1 | 3/2005 | Turner |
| 2005/0079152 A1 | 4/2005 | Bot |
| 2005/0079553 A1 | 4/2005 | Ayyoub |
| 2005/0080128 A1 | 4/2005 | Tsukamoto |
| 2005/0100877 A1 | 5/2005 | Xu |
| 2005/0107322 A1 | 5/2005 | OHagan |
| 2005/0122550 A1 | 6/2005 | Plewa |
| 2005/0158390 A1 | 7/2005 | Rana |
| 2005/0191294 A1 | 9/2005 | Arap |
| 2005/0207940 A1 | 9/2005 | Butler |
| 2005/0214378 A1 | 9/2005 | Hoarau |
| 2005/0233948 A1 | 10/2005 | DAmico |
| 2005/0244863 A1 | 11/2005 | Mir |
| 2005/0249799 A1 | 11/2005 | Jacob |
| 2005/0260186 A1 | 11/2005 | Bookbinder |
| 2006/0002852 A1 | 1/2006 | Saltzman |
| 2006/0004042 A1 | 1/2006 | Dalton |
| 2006/0009529 A1 | 1/2006 | Dalton |
| 2006/0035966 A1 | 2/2006 | Dalton |
| 2006/0062787 A1 | 3/2006 | Hitraya |
| 2006/0083711 A1 | 4/2006 | Berry |
| 2006/0111271 A1 | 5/2006 | Cerny |
| 2006/0173170 A1 | 8/2006 | Chamberlain |
| 2006/0183931 A1 | 8/2006 | Dalton |
| 2006/0228371 A1 | 10/2006 | Raso |
| 2006/0239907 A1 | 10/2006 | Luzzi |
| 2006/0240093 A1 | 10/2006 | MacLachlan |

(56) References Cited

U.S. PATENT DOCUMENTS

| | | |
|---|---|---|
| 2006/0241180 A1 | 10/2006 | Dalton |
| 2006/0258628 A1 | 11/2006 | Steiner |
| 2006/0269557 A1 | 11/2006 | Sherman |
| 2006/0276540 A1 | 12/2006 | Dalton |
| 2006/0287547 A1 | 12/2006 | Dalton |
| 2007/0014807 A1 | 1/2007 | Maida |
| 2007/0116768 A1 | 5/2007 | Chorny |
| 2007/0184068 A1 | 8/2007 | Renner |
| 2007/0225213 A1 | 9/2007 | Kosak |
| 2008/0026000 A1 | 1/2008 | Ennifar |
| 2008/0031899 A1 | 2/2008 | Reddy |
| 2008/0081074 A1 | 4/2008 | Gu |
| 2008/0171059 A1 | 7/2008 | Howland |
| 2008/0213377 A1 | 9/2008 | Bhatia |
| 2008/0268063 A1 | 10/2008 | Jon |
| 2008/0299177 A1 | 12/2008 | Hardy |
| 2009/0004118 A1 | 1/2009 | Nie |
| 2009/0028910 A1 | 1/2009 | DeSimone |
| 2009/0117549 A1 | 5/2009 | Tan |
| 2009/0298710 A1 | 12/2009 | Farokhzad |
| 2010/0022680 A1 | 1/2010 | Karnik |
| 2010/0092425 A1 | 4/2010 | vonAndrian |
| 2010/0129392 A1 | 5/2010 | Shi |
| 2010/0129439 A1 | 5/2010 | Alexis |
| 2010/0144845 A1 | 6/2010 | Farokhzad |
| 2010/0183727 A1 | 7/2010 | Iannacone |
| 2010/0196482 A1 | 8/2010 | Radovic-Moreno |
| 2010/0203142 A1 | 8/2010 | Zhang |
| 2010/0233251 A1 | 9/2010 | VonAndrian |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 1279404 | 1/2003 |
| EP | 1752141 A1 | 2/2007 |
| EP | 1932538 | 6/2008 |
| WO | 8804300 | 6/1988 |
| WO | 9011364 | 3/1990 |
| WO | 9704747 | 2/1997 |
| WO | 9713537 A1 | 4/1997 |
| WO | 9737705 A1 | 10/1997 |
| WO | 9808856 | 3/1998 |
| WO | 9814216 | 4/1998 |
| WO | 9851325 | 11/1998 |
| WO | 9901498 | 1/1999 |
| WO | 9934850 A1 | 7/1999 |
| WO | 9961054 | 12/1999 |
| WO | 0021572 | 4/2000 |
| WO | 0027363 | 5/2000 |
| WO | 0032239 | 6/2000 |
| WO | 0044895 | 8/2000 |
| WO | 0175164 | 10/2001 |
| WO | 0218477 | 3/2002 |
| WO | 02076469 | 10/2002 |
| WO | 02076603 | 10/2002 |
| WO | 02100442 | 12/2002 |
| WO | 03004654 | 1/2003 |
| WO | 03028657 | 4/2003 |
| WO | 03030941 | 4/2003 |
| WO | 03051304 | 6/2003 |
| WO | 03072637 | 9/2003 |
| WO | 03074679 | 9/2003 |
| WO | 03102708 | 12/2003 |
| WO | 2004030608 | 4/2004 |
| WO | 2004071493 A1 | 8/2004 |
| WO | 2004096998 | 11/2004 |
| WO | 2004105782 | 12/2004 |
| WO | 03000777 | 1/2005 |
| WO | 2005012407 | 2/2005 |
| WO | 2005028539 | 3/2005 |
| WO | 2005042573 | 5/2005 |
| WO | 2005072710 | 8/2005 |
| WO | 2005111192 | 11/2005 |
| WO | 2005112885 | 12/2005 |
| WO | 2005121181 | 12/2005 |
| WO | 2006037979 | 4/2006 |
| WO | 2006042146 | 4/2006 |
| WO | 2006066158 | 6/2006 |
| WO | 2006078278 | 7/2006 |
| WO | 2006090924 | 8/2006 |
| WO | 2006096754 | 9/2006 |
| WO | 2006117217 | 11/2006 |
| WO | 2006133271 | 12/2006 |
| WO | 2006138463 | 12/2006 |
| WO | 2007001448 A2 | 1/2007 |
| WO | 2007021142 | 2/2007 |
| WO | 2007024026 | 3/2007 |
| WO | 2007070682 | 6/2007 |
| WO | 2007076371 | 7/2007 |
| WO | 2007084797 | 7/2007 |
| WO | 2007098254 | 8/2007 |
| WO | 2007109364 | 9/2007 |
| WO | 2007118653 | 10/2007 |
| WO | 2007150030 | 12/2007 |
| WO | 2008051291 | 5/2008 |
| WO | 2009051837 | 4/2009 |
| WO | 2009109428 | 9/2009 |

OTHER PUBLICATIONS

Ackermand & Cresswell, "Cellular mechanisms governing cross-presentation presentation of exogenous antigens", Nat. Immunol., 5(7):678-684 (2004).

Aime, et al., "Lanthanide(III) chelates for NMR biomedical applications", Chemical Society Reviews, 27:19-29 (1998).

Akagi, et al., "Development of vaccine adjuvants using polymeric nanoparticles and their potential applications for anti-HIV vaccine", Yakugaku Zasshi, 127(2):307-17 (2007) English Abstract.

Akagi, et al., "Multifunctional conjugation of proteins on/into bio-nanoparticles prepared by amphiphilic poly(gamma-glutamic acid)", J Biomat Sci Polym Ed., 17 (8):875-92 (2006).

Akaishi, et al., "Targeting chemotherapy using antibody-combined liposome against human pancreatic cancer cell-line.", The Tohoku Journal of Experimental Medicine, 175(1):29-42 (1995).

Allen, et al., "Nano-engineering block copolymer aggregates for drug delivery.", Colloids Surfaces B-Biointerfaces, 16:3-27 (1999).

Allison, et al., "The mode of action of immunological adjuvants.", Dev. Biol. Stand., 92:3-11 (1998).

Altschul, et al., "Basic local alignment search tool.", J. Mol Biol., 215 (3):403-10 (1990).

Altschul, et al., "Gapped BLAST and PSI-BLAST: a new generation of protein database search programs.", Nucleic Acids Res., 25(17):3389-3402 (1997).

Angelucci, et al., "Neuroendocrine transdifferentiation induced by VPA is mediated by PPAR$^3$ activation and confers resistance to antiblastic therapy in prostate carcinoma", The Prostate, 68(6):588-598 (2008).

Argov-Argaman, et al., "Lactosomes: Structural and compositional classification of unique nanometer-sized protein lipid particles of human milk", J Agric Food Chem., 58:11234-42 (2010).

Astete and Sabliov, "Synthesis and characterization of PLGA nanoparticles", J. Biomat. Sci.,—Polymer Ed., 17:247-289 (2006).

Atkinson, et al., "Conjugation of folate via gelonin carbohydrate residues retains ribosomal-inactivating properties of the toxin and permits targeting to folate receptor positive cells.", J. Biol. Chem., 276(30):27930-27935 (2001).

Avgoustakis, "Pegylated poly(lactide) and poly(lactide-co-glycolide) nanoparticles: preparation, properties and possible applications in drug delivery" Curr Drug Deliv., 1:321-33 (2004).

Baba, et al., "Human neutralizing monoclonal antibodies of the IgG1 subtype protect against mucosal simian-human immunodeficiency virus infection.", Nat. Med., 6(2):200-206 (2000).

Babaian, et al., "Radioimmunological imaging of metastatic prostatic cancer with 111indium-labeled monoclonal antibody PAY 276.", J. Urol., 137(3):439-443 (1987).

(56) References Cited

OTHER PUBLICATIONS

Bachmann, et al., "T helper cell-independent neutralizing B cell response against vesicular stomatitis virus: role of antigen patterns in B cell induction?", Eur. J. Immunol., 25 (12):3445-3451 (1995).
Bagalkot, et al., "An Aptamer-Doxorubicin Physical Conjugate as a Novel Targeted Drug-Delivery Platform", Angew. Chem. Int. Ed., 45(48):8149-8152 (2006).
Bander, et al., "Targeting metastatic prostate cancer with radiolabeled monoclonal antibody J591 to the extracellular domain of prostate specific membrane antigen.", J. Urol., 170(5)1717-1721 (2003).
Barchet, et al., "Virus-induced interferon alpha production by a dendritic cell subset in the absence of feedback signaling in vivo.", J. Exp. Med., 195 (4):507-516 (2002).
Barrera, et al., "Synthesis and RGD peptide modification of a new biodegradable copolymer: poly(lactic acid-co-lysine)", J. Am. Chem. Soc., 115 (23):11010-11011 (1993).
Bauer, et al., "SMS 201-995: a very potent and selective octapeptide analogue of somatostatin with prolonged action.", Life Sci., 31(11):1133-1140 (1982).
Beaureparie, et al., " Functionalized Fluorescent Oxide Nanoparticles: Artificial Toxins for Sodium Channel Targeting and Imaging at the Single-Molecule Level", Nano Letters, 4 (11):2079-2083 (2004).
Bennett, et al., "Inhibition of the Aminopeptidase from Aeromonas Proteolytica by I-Leucinephosphonic Acid, a Transition State Analogue of Peptide Hydrolysis", J. Am. Chem. Soc., 120(46):12139-12140 (1998).
Bies et al., Lectin-medicated drug targeting: history and applications\, Advanced Drug Delivery Reviews, 56:425-435 (2004).
Binetruy-Tournaire, et al., "Identification of a peptide blocking vascular endothelial growth factor (VEGF)-mediated angiogenesis.", EMBO J., 19 (7):1525-1533 (2000).
Bjerke, et al., "Comparison of monoclonal and polyclonal antibodies to continine in nonisotopic and isotopic immunoassays", J. Immunol. Meth., 96:239-246 (1987).
Bocca, et al., "Phagocytic uptake of fluorescent slealth solid lipid nanoparticles", Int. J. Pharmaceutics, 175:185-193 (1998).
Boes, et al., "T-cell engagement of dendritic cells rapidly rearranges MHC class II transport.", Nature, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance,", J. Exp. Med., 196(12):1627-1638 (2002).
Bottausci, et al., "Mixing in the shear superposition micromixer: three-dimensional analysis", Philosophical Transactions of the Royal Society of London Series a—Mathematical Physical and Engineering Sciences, 362:1001-1018 (2004).
Boussif, et al., "A versatile vector for gene and oligonucleotide transfer into cells in culture and in vivo: polyethylenimine.", Proc. Natl. Acad. Sci., USA, 1995, 92:7297-7301 (1995).
Bozzacco, et al., "DEC-205 receptor on dendritic cells mediates presentation of HIV gag protein to CD8+ T cells in a spectrum of human MHC I haplotypes.", Proc. Natl. Acad, Sci., USA, 104(4):1289-1294 (2007).
Brito, et al., "Nanoparticulate carriers for the treatment of coronary restenosis.", Int J Nanomedicine, 2(2):143-161 (2007).
Brooking et al., "Transport of Nanoparticles Across the Rat Nasal Mucosa", Journal of Drug Targeting, 9(4):267-279 (2001).
Burmeister, et al., "Direct in vitro selection of a 2'-O-methyl aptamer to VEGF.", Chem Biol, 12(1):25-33 (2005).
Caring, et al., "Nanosphere based oral insulin delivery," J. Control. Release, 65 (1-2):261-9 (2000).
Casola, et al., "B cell receptor signal strength determines B cell fate.", Nat. Immunol., 5(3):317-327 (2004).
Castro, et al., "Nicotine Antibodies: Comparison of Ligand Specificities of Antibodies Produced against Two Nicotine Conjugates", Eur. J. Biochem 104:331-340 (1980).
Castro & Prieto, "Nicotine Antibody Production: Comparison of two nicotine conjugates in different animal species", Biochem. Biophys. Res. Comm., 67 (2):583-589 (1975).
Cerchia, et al. "Neutralizing aptamers from whole-cell SELEX inhibit the RET receptor tyrosine kinase", PLoS Biology, 3(4):849-60 (2005).
Chacon, et al., "Optimized preparation of poly D,L (lactic-glycolic) microspheres and nanoparticles for oral administration", Int'l J. Pharmaceutics, 141:81-91 (1996).
Chaires, et al., "Preferential binding of daunomycin to 5'ATCG and 5'ATGC sequences revealed by footprinting titration experiments.", Biochemistry, 29 (26):6145-6153 (1990).
Chandy, et al., "5-Fluorouracil-loaded chitosan coated polylactic acid pmicrospheres as biodegradable drug carriers for cerebral tumors", J. Microencapsulation, 17(5):625-638 (2000).
Chandy et al., "Development of Poly(Lactic Acid)/Chitosan Co-Matrix Microspheres: Controlled Release of Taxol-Heparin for Preventing Restenosis", Drug Delivery, 8:77-86 (2001).
Chang, et al., "Five Different Anti-Prostate-specific Membrane Antigen (PSMA) Antibodies Confirm Psma Expression in Tumor-associated Neovasculature", Cancer Res., 59:3192-3198 (1999).
Cheng, et al., "Formulation of functionalized PLGA-PEG nanoparticles for in vivo targeted drug delivery.", Biomaterials, 28(5):869-876 (2007).
Christian, et al., "Nucleolin expressed at the cell surface is a marker of endothelial cells in angiogenic blood vessels.", J. Cell Biol., 163(4):871-878 (2003).
Chu, et al, "Aptamer:toxin conjugates that specifically target prostate tumor cells", Cancer Res., 66:5989-92 (2006).
Chu, et al., "Aptamer mediated siRNA delivery", Nuc. Acid Res., 34:e73 (2006).
Chu, et al., "Labeling tumor cells with fluorescent nanocrystal-aptamer bioconjugates.", Biosens. Bioelectron., 21:1859-1866 (2006).
Clark, "The reticulum of lymph nodes in mice studied with the electron microscope.", Am. J. Anat., 110:217-257 (1962).
Connor, et al., "Ex vivo evaluation of anti-EpCAM immunocytokine huKS-IL2 in ovarian cancer.", J. Immunother., 27(3):211-219 (2004).
Coppi, et al., "Chitosan-Alginate Microparticles as a Protein Carrier", Drug Development and Industrial Pharmacy, 27(5):393-400 (2001).
Croy and Kwon, "Polymeric micells for drug delivery", Curr. Pharm. Design, 12:4669-4684 (2006).
Dang and Rock, "Stimulation of B lymphocytes through surface Ig receptors induces LFA-1 and ICAM-1-dependent adhesion.", J. Immunol., 146 (10):3273-3279 (1991).
De Graaf, et al., "A fully human anti-Ep-CAM scFv-beta-glucuronidase fusion protein for selective chemotherapy with a glucuronide prodrug.", Br. J. Cancer, 86 (5):811-818 (2002).
De Jaeghere, et al., "Freeze-drying and lyopreservation of diblock and triblock poly (lactic acid)-poly(ethylene oxide) (PLA-PEO) copolymer nanoparticles.", Pharm. Dev. Technol., 5(4):473-483 (2000).
Delemarre, et al., "Repopulation of macrophages in popliteal lymph nodes of mice after liposome-mediated depletion.", J. Leukoc. Biol., 47(3):251-257 (1990).
Demello, "Control and detection of chemical reactions in microfluidic systems.", Nature, 442(7101):394-402 (2006).
Demello and Demello, "Microscale reactors: nanoscale products.", Lab on a Chip, 4(2):11N-15N (2004).
Deming, et al., "Facile synthesis of block copolypeptides of defined architecture." Nature, 390(6658):386-389 (1997).
Derfus, et al., "Intracellular Delivery of Quantum Dots for Live Cell Labeling and Organelle Tracking", Advanced Materials, 16:961-966 (2004).
Dimarco and Arcamone, "DNA complexing antibiotics: Daunomycin, adriamycin and their derivates.", Arzneim-Forsch. (Drug Res.), 25:368-375 (1975).
Ding, et al., "Syntheses of conformationally constricted molecules as potential NAALADase/PSMA inhibitors.", Org. Lett., 6(11):1805-1808 (2004).

(56) References Cited

OTHER PUBLICATIONS

Dinkla, et al., "Identification of a streptococcal octapeptide motif involved in acute rheumatic fever." ,J. Biol. Chem., 282(26):18686-18693 (2007).
Dykxhoorn, et al., "Killing the messenger: short RNAs that silence gene expression." , Nat. Rev. Mol. Cell Biol., 4(6):457-467 (2003).
D\Antonio, et al., "Longitudinal analysis of androgen deprivation of prostate cancer cells identifies pathways to androgen independence" , The Prostate, 68 (7):698-714 (2008).
Eklund, et al., "Denileukin diftitox: a concise clinical review." , Expert Rev. Anticancer Ther., 5(1):33-38 (2005).
Elamanchili, et al., "Pathogen-mimicking nanoparticles for vaccine delivery to dendritic cells" , J Cont. Rel., 30(4):378-95 (2007).
Elbashir, et al., "RNA interference is mediated by 21- and 22-nucleotide RNAs." , Genes Dev., 15(2):188-200 (2001).
Eldridge, et al., "Biodegradable microspheres as a vaccine delivery system," Mol. Immunol., 28(3):287-94 (1991).
Elsässer-Beile, et al., "A new generation of monoclonal and recombinant antibodies against cell-adherent prostate specific membrane antigen for diagnostic and therapeutic targeting of prostate cancer," , Prostate, 66(13)1359-1370 (2006).
Elvassore, et al., "Production iof Insulin-Loaded Poly(Ethylene Glycol)/Poly(I-Lactide) (PEG/PLA) Nanoparticles by Gas Antisolvent Techniques" , Journal of Pharmacrutical Sciences, 90(10):1628-36 (2001).
Ermak and Giannasca, "Microparticle targeting to M cells" , Advanced Drug Delivery Reviews, 34:261-283 (1998).
Farokhazad, et al., "Nanoparticle-Aptamer Bioconjugates: A New Approach for Targeting Prostate Cancer Cells," Cancer Research, 64:7668-7672 (2004).
Farokhzad, et al., "Nanoparticle-aptamer bioconjugates for cancer targeting" , Expert Opin. Drug Delivery, 3(3):311-324 (2006).
Farokhzad, et al., "Targeted nanoparticle-aptamer bioconjugates for cancer chemotherapy in vivo." , Proc. Natl. Acad. ScL, USA, 103(16):6315-6320 (2006).
Farr, et al., "The structure of the sinus wall of the lymph node relative to its endocytic properties and transmural cell passage." , Am. J. Anat., 157(3):265-284 (1980).
Fire, et al., "Potent and specific genetic interference by double-stranded RNA in Caenorhabditis elegans." , Nature, 391(6669):806-811 (1998).
Fi Li Povic-Grcic et al., "Mucoadhesive chitosan-coated liposomes: characteristics and stability" , J. Microencapsulation, 18 1 :3-12 (2001).
Fonseca, et al., "Paclitaxel-loaded PLGA nanoparticles: preparation, physicochemical characterization and in vitro anti-tumoral activity." , J. Control. Release, 83(2):273-286 (2002).
Foss, et al., "Radiolabeled small-molecule ligands for prostate-specific membrane antigen: in vivo imaging in experimental models of prostate cancer" , Clin. Cancer Res., 11:4022-28 (2005).
Fracasso, et al., "Anti-tumor effects of toxins targeted to the prostate specific membrane antigen." , Prostate, 53(1):9-23 (2002).
Francis, et al., "A phase I trial of antibody directed enzyme prodrug therapy (ADEPT) in patients with advanced colorectal carcinoma or other CEA producing tumours." , Br. J. Cancer, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia." , Clin. Cancer Res., 8(5):1004-1013 (2002).
Frederick, et al., "Structural comparison of anticancer drug-DNA complexes: adriamycin and daunomycin." , Biochemistry, 29(10):2538-2549 (1990).
Froidevaux, et al., "Somatostatin analogs and radiopeptides in cancer therapy." , Biopolymers, 66(3):161-183 (2002).
Fujita, et al., "Cytokine profiling of prostatic fluid from cancerous prostate glands identifies cytokines associated with extent of tumor and inflammation" , The Prostate, 68 (8):872-882 (2008).

Gao, et al., "A method for the generation of combinatorial antibody libraries using pIX phage display," Proc. Natl. Acad. Sci. U.S.A., 99(20): 12612-6 (2002).
Gao, et al., "In vivo cancer targeting and imaging with semiconductor quantum dots." , Nat. Biotechnol., 22(8):969-976 (2004).
Gao, et al., "In vivo molecular and cellular imaging with quantum dots." , Curr. Op. Biotechnol., 16:63-72 (2005).
Gaserod et al., "The enhancement of the bioadhesive properties of calcium alginate gel beads by coating with chitosan" , Intl. J. of Pharmaceutics, 175:237-246 (1998).
Gershlick, "Treating atherosclerosis: local drug delivery from laboratory studies to clinical trials," Atherosclerosis, 160(2): 259-71 (2002).
Gillies, et al., "An anti-CD20-IL-2 immunocytokine is highly efficacious in a SCID mouse model of established human B lymphoma." , Blood, 105 (10):3972-3978 (2005).
Gorelik, et al., "Scanning surface confocal microscopy for simultaneous topographical and fluorescence imaging: application to single virus-like particle entry into a cell" , PNAS, 99(25):16018-23 (2002).
Govender, et al., "Defining the drug incorporation properties of PLA-PEG nanoparticles" , Intl J of Pharmaceutics, 1999:95-110(2000).
Grauer, et al., "Identification, purification, and subcellular localization of prostate-specific membrane antigen PSM' protein in the LNCaP prostatic carcinoma cell line." , Cancer Res., 58(21):4787-4789 (1998).
Gref, et al., "Biodegradable long-circulating polymeric nanospheres." , Science, 263(5153):1600-1603 (1994).
Haensler, et al., "Polyamidoamine cascade polymers mediate efficient transfection of cells in culture" , Bioconjugate Chem., 4(5):372-379 (1993).
Haj, et al., "New findings in the study on the intercalation of bisdaunorubicin and its monomeric analogues with naked and nucleus DNA." , Chem. Biol. Interact., 145(3):349-358 (2003).
Hallahanm, et al., "Integrin-mediated targeting of drug delivery to irradiated tumor blood vessels" , Cancer Cell, 3:63-74 (2003).
Hanes, et al., "Polymer microspheres for vaccine delivery." , Pharm. Biotechnol., 6:389-412 (1995).
Hangartner, et al., "Antiviral immune responses in gene-targeted mice expressing the immunoglobulin heavy chain of virus-neutralizing antibodies." , Proc. Natl. Acad. Sci., USA, 100:12883-12888 (2003).
Hannon, et al., "Unlocking the potential of the human genome with RNA interference" , Nature, 431(7006):371-378 (2004).
Harada and Kataoka, "Supramolecular assemblies of block copolymers in aqueous media as nanocontainers relevant to biological applications" , Progress Polymer Sci., 31(11):949-982 (2006).
Harper, et al., "Efficacy of a bivalent L1 virus-like particle vaccine in prevention of infection with human papiliomavirus types 16 and 18 in young women: a randomised controlled trial." , Lancet, 364 (9447):1757-1765 (2004).
Harris, et al., "Proteolytic actuation o nanoparticle self-assembly" , Angewandte Chemie, 118:3233-7 (2006).
Haseloff and Gerlach, "Simple RNA enzymes with new and highly specific endoribonuclease activities." , Nature, 334(6183):585-591 (1988).
Hawiger, et al., "Dendritic cells induce peripheral T cell unresponsiveness under steady state conditions in vivo." , Nature, 334(6183):585-591 (1988).
He et al., "A microRNA polycistron as a potential human oncogene," Nature, 435 (7043): 828-833 (2005).
Heald, et al., "Poly(lactic acid)-polyethylene oxide) (PLA-PEG) nanoparticles: NMR studies of the central solidlike PLA core and the liquid PEG corona" , Langmuir, 18:3669-3675 (2002).
Hejazi et al ., "Stomach-specific anti-H. pylon therapy. I: preparation and characterization of tetracyline-loaded chitosan microshpheres" , Intl. J. of Pharmaceutics, 235:87-94 (2002).
Helene, et al., "Control of gene expression by triple helix-forming oligonucleotides. The antigene strategy." , Ann, N.Y. Acad. Sci. 660:27-36 (1992).
Hennenfent, et al., "Novel formulations of taxanes: a review. Old wine in a new bottle" , Ann Oncol., 17:735-49 (2005).

(56) References Cited

OTHER PUBLICATIONS

Hermann and Patel, "Adaptive recognition by nucleic acid aptamers," Science, 287: 820-825 (2000).
Hieda, et al., "Active Immunization Alters the Plasma Nicotine Concentration in Rats", J. Pharmacol. Exp. Therapeutics, 283:1076-1081 (1997).
Hieda, et al., "Immunization of rats reduces nicotine distribution to brain", Psychopharmacology, 143:150-157 (1999).
Horoszewicz, et al., "Monoclonal antibodies to a new antigenic marker in epithelial prostatic cells and serum of prostatic cancer patients.", Anticancer Res., 7(5B):927-935 (1987).
Houghton, "General method for the rapid solid-phase synthesis of large numbers of peptides: Specificity of antigen-antibody interaction at the level of individual amino acids", Immunol., 82:5131-5135 (1985).
Huang et al., "Microencapsulation of Chlorpheniramine Maleate-Resin Particles with Crosslinked Chitosan for Sustained Release", Pharmaceutical Development and Technology, 4 1:107-115 (1999).
Héléne, "The anti-gene strategy: control of gene expression by triplex-forming-oligonucleotides.", Anticancer Drug Des. 6(6):569-584 (1991).
Jackson, et al., "Design and pharmacological activity of phosphinic acid based NAALADase inhibitors.", J. Med. Chem., 44(24):4170-4175 (2001).
Jackson, et al., "Design of NAALADase inhibitors: a novel neuroprotective strategy.", Curr. Med. Chem., 8(8):949-957 (2001).
Janes et al., "Chitosan nanoparticles as delivery systems for doxorubicin", Journal of Controlled Release, 73:255-267 (2001).
Jayaprakash, et al., "Design and synthesis of a PSMA inhibitor-doxorubicin conjugate for targeted prostate cancer therapy", Chem Med Chem., 1:299-302 (2006).
Jayasena, "Aptamers: An Emerging Class of Molecules That Rival Antibodies in Diagnostics", Clinical Chemistry, 45(9):1628-1650 (1999).
Johnson and Prud/Homme, "Mechanism for rapid self-assembly of block copolymer nanoparticles.", Phys. Rev. Lett., 91(11):118302 (2003).
Jones and Leroux, "Polymeric micelles a new generation of colloidal drug carriers", Eur. J. Pharmaceutics Biopharmaceutics, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", Pharmaceutical Research, 18(3):352-360 (2001).
Junt, et al., "Subcapsular sinus macrophages in lymph nodes clear lymph-borne viruses and present them to antiviral B cells", Nature, 450:110-116 (2007).
Kabanov, et al., "DNA Complexes with Polycations for the Delivery of Genetic Material into Cells", Bioconjugate Chem., 6(1):7-20 (1995).
Kamentsky, "Laser scanning cytometry.", Methods Cell Biol., 63:51-87 (2001).
Kanashiro, et al., "Inhibition of mutant p53 expression and growth of DMS-153 small cell lung carcinoma by antagonists of growth hormone-releasing hormone and bombesin.", Proc. Natl. Acad. Sci., USA, 100(26):15836-15041 (2003).
Karlin and Altschul, "Applications and statistics for multiple high-scoring segments in molecular sequences.", Proc. Nati Acad. Sci. USA, 90 (12):5873-5877 (1993).
Karlin and Altschul, "Methods for assessing the statistical significance of molecular sequence features by using general scoring schemes.", Proc. Natl Acad Sci. USA, 87:2264-2268 (1990).
Karrer, et al., "On the key role of secondary lymphoid organs in antiviral immune responses studied in alymphoplastic (aly/aly) and spleenless (Hox11(-)/-) mutant mice.", J. Exp. Med., 185(12):2157-2170 (1997).
Kawamura, et al., "Dendritic cells that endocytosed antigen-containing IgG-liposomes elicit effective antitumor immunity", J Immunother., 29(2):165-74 (2006).

Kawashima, et al., "Mucoadhesive DL-Lactide/Glycolide Copolymer Nanoshperes Coated with Chitosan to Improve Oral Delivery of Elcatonin", Pharmaceutical Development and Technology, 5(1):77-85 (2000).
Kelly, et al., "The Optical Properties of Metal Nanoparticles: The Influence of Size, Shape, and Dielectric Environment", J. Phys. Chem. B., 107(3):668-677 (2003).
Khademhosseini, et al., "Cell docking inside microwells within reversibly sealed microfluidic channels for fabricating multiphenotype cell arrays," Lab Chip, 5(12):1380-6 (2005).
Khandare, et al., "Polymer-drug conjugates: Progress in polymeric prodrugs," Progress in Polymer Science, 31(4): 359-397 (2006).
Kim, et al., "Target-specific cellular uptake of PLGA nanoparticles coated with poly(L-lysine)-poly(ethyleneglycol)-folate conjugate", Langmuir, 21(19): 8852-8857 (2005).
Knight, et al., "Hydrodynamic Focusing on a Silicon Chip: Mixing Nanoliters in Microseconds", Phys. Rev. Lett., 80:3863-3866 (1998).
Koenig, et al., "Immunologic factors in human milk: the effects of gestational age and pasteurization", J Human Lactation, 21:439-43 (2002).
Koivunen, et al., "Phage libraries displaying cyclic peptides with different ring sizes: ligand specificities of the RGD-directed integrins.", Biotechnology (NY), 13 (3):265-270 (1995).
Koivunen, et al., "Tumor targeting with a selective gelatinase inhibitor", Nat. Biotechnol., 17:768-774 (1999).
Konan, et al., "Preparation and characterization of sterile sub-200 nm meso-tetra(4- hydroxylphenyl)porphyrin-loaded nanoparticles for photodynamic therapy", Eur. J. Pharmaceutics Biopharmaceutics, 55:115-124 (2003).
Kozikowski, et al., "Synthesis of urea-based inhibitors as active site probes of glutamate carboxypeptidase II: efficacy as analgesic agents.", J. Med. Chem., 47 (7):1729-1738 (2004).
Kreitman, et al., "Efficacy of the anti-CD22 recombinant immunotoxin BL22 in chemotherapy-resistant hairy-cell leukemia.", N. Engl J. Med., 345(4):241-347 (2001).
Kreitman, et al., "Phase 1 trial of recombinant immunotoxin anti-Tac(Fv)-PE38 (LMB-2) in patients with hematologic malignancies.", J. Clin. Oncol., 18 (8):1622-1636 (2000).
Krieg, et al., "CpG motifs in bacterial DNA trigger direct B-cell activation." Nature, 374(6522):546-549 (1995).
Kukowska-Latallo, et al., "Efficient transfer of genetic material into mammalian cells using Starburst polyamidoamine dendrirners", Proc. Natl. Acad. Sci., USA, 93(10):4897-4902 (1996).
Kumar, et al., "Inhibition of angiogenesis and tumor growth by SCH221153, a dual alpha(v)beta3 and alpha(v)beta5 integrin receptor antagonist.", Cancer Res., 61(5):2232-2238 (2001).
Kwon, et al., "Pseudopoly(amino acids): A study of the synthesis and characterization of poly(acyl-hydroxyproline-esters)", Macromolecules, 22:3250-3255 (1989).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", Nucleic Acids Res., 32(21):6200-6211 (2004).
Köhrer, et al., "Import of amber and ochre suppressor tRNAs into mammalian cells: a general approach to site-specific insertion of amino acid analogues into proteins.", Proc. Natl. Acad. Sci., USA, 98(25):14310-14315 (2001).
Köhrer and Rajbhandary, "Proteins carrying one or more unnatural amino acids," In Ibba, et al., (eds.), Aminoacyl-tRNA Synthetases, Landes Bioscience, Chapter 31 (2005).
Laakkonen, et al., "Antitumor activity of a homing peptide that targets tumor lymphatics and tumor cells.", Proc. Natl. Acad. Sci., USA, 101(25):9381-9386 (2004).
Labhasetwar, et al., "Arterial uptake of biodegradable nanoparticles: Effect of surface modifications," J. Pharm. Sci., 87(10): 1229-34 (1998).
Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).

(56) References Cited

OTHER PUBLICATIONS

Langer, "Biomaterials in drug delivery and tissue engineering: one laboratory's experience.", Acc. Chem. Res., 33(2):94-101 (2000).
Langer, "New methods of drug delivery," Science, 249(4976):1527-33 (1990).
Langer, "Selected advances in drug delivery and tissue engineering", J. Control. Release, 62:7-11 (1999).
Langone, et al., "Nicotine and its metabolites. Radioimmunoassays for nicotine and cotinine", Biochem., 12(24):5025-5030 (1973).
Langone & Van Vunakis, "Radioimmunoassay of Nicotine, Cotinine, and $^3$-(3-Pyridyl)-$^3$-oxo-N-methylbutyramide", Met. Enzymol., 84:628-640 (1982).
Leamon, et al., "Cytotoxicity of folate-Pseudomonas exotoxin conjugates toward tumor cells. Contribution of translocation domain.", J. Biol. Chem., 268 (33):24847-24854 (1993).
Leamon, et al., "Selective targeting of malignant cells with cytotoxin-folate conjugates.", J. Drug Target., 2(2):101-112 (1994).
Lee, et al. "Adaptations of Nanoscale Viruses and Other Protein Cages for Medical Applications" Nanomedicine-Nanotechnology Biology and Medicine. 2 (3):137-149 (2006).
Lehr, "Lectin-mediated drug delivery: The second generation of bioadhesives", J. of Controlled Release, 65:19-29 (2000).
Leopold, et al., "Fluorescent virions: dynamic tracking of the pathway of adenoviral gene transfer vectors in living cells.", Human Gene Therapy, 9 (3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo," Cancer, 64(1):1-5 (1989).
Leucuta, et al., "Albumin microspheres as a drug delivery system for epirubicin: pharmaceutical, pharmacokinetic and biological aspects," International Journal of Pharmaceutics, 41: 213-7 (1988).
Lim, et al., "A Self-Destroying Polycationic Polymer: Biodegradable Poly(4-hydroxy-l-proline ester)", J. Am. Chem. Soc., 121(24):5633-5639 (1999).
Lim, et al., "Cationic hyperbranched poiy(amino ester): a novel class of DNA condensing molecule with cationic surface, biodegradable three-dimensional structure, and tertiary amine groups in the interior.", J. Am. Chem. Soc, 123(10)2460-2461 (2001).
Lim et al., "Preparation and evaluation of the in vitro drug release properties and mucoadhesion of novel microspheres of hyaluronic acid and chitosan", J. of Controlled Release, 66:281-292 (2000).
Lin, et al, "A microRNA polycistron as a potential human oncogene p828", Nature, 435(7043):828-833 (2005).
Lin, et al., "Well-Ordered Mesoporous Silica Nanoparticles as Cell Markers", Chem. Mater., 17:4570-4573 (2005).
Liu, et al., "Cell-Surface labeling and internalization by a fluorescent inhibitor of prostate-specific membrane antigen", The Prostate, 68(9):955-964 (2008).
Liu, et al., "Constitutive and antibody-induced internalization of prostate-specific membrane antigen.", Cancer Res., 58(18):4055-4060 (1998).
Liu, et al., "Folate-targeted enzyme prodrug cancer therapy utilizing penicillin-V amidase and a doxorubicin prodrug.", J. Drug Target., 7:43-53 (1999).
Liu, et al., "Hypermethylation of MCAM gene is associated with advanced tumor stage in prostate cancer", The Prostate, 68(4):418-426 (2008).
Liu, et al., "Monoclonal antibodies to the extracellular domain of prostate-specific membrane antigen also react with tumor vascular endothelium.", Cancer Res., 57 (17):3629-3634 (1997).
Low, et al., "Folate receptor-targeted drugs for cancer and inflammatory diseases.", Adv. Drug Deily. Rev., 56(8):1055-1058 (2004).
Lu, et al., "MicroRNA expression profiles classify human cancers", Nature, 435 (7043):834-838 (2005).
Ludewig, et al., "Induction of optimal anti-viral neutralizing B cell responses by dendritic cells requires transport and release of virus particles in secondary lymphoid organs.", Eur. J. Immunol., 30 (1):185-196 (2000).
Lupold, et al., "Identification and characterization of nuclease-stabilized RNA molecules that bind human prostate cancer cells via the prostate-specific membrane antigen.", Cancer Res., 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", Mol. Cancer Thor., 4(8):1205-1213 (2005).
Maher, "DNA triple-helix formation: An approach to artificial gene repressors?", Bioassays 14:807-815 (1992).
Majer, et al., "Synthesis and biological evaluation of thiol-based inhibitors of glutamate carboxypeptidase II: discovery of an orally active GCP II inhibitor.", J. Med. Chem., 46 (10)1989-1996 (2003).
Manolova, et al., "Nanoparticles target distinct dendritic cell populations according to their size", Eur. J. Immunol., 38:1404-1413 (2008).
Manz, et al., "Capillary electrophoresis on a chip", J. Chromatography, 593:253-258 (1992).
Martin, et al., "Crystal structure at 2.8 A of an FcRn/heterodimeric Fc complex: mechanism of pH-dependent binding.", Mal Cell, 7:867-77 (2001).
Mathiowitz, et al., "Novel microcapsules for delivery systems", Reactive Polymers, 6:275-283 (1987).
Mathiowitz, et al., "Polyanhydride Microspheres as Drug Carriers. II.. Microencapsulation by Solvent Removal", J. Appl. Polymer Sci., 35:755-774 (1988).
Mathiowitz, et al., "Polyanhydride Microspheres as Drug Carriers I. Hot Melt Encapsulation", J. Control. Release, 5:13-22 (1987).
Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).
Mattheakis, et al., "Optical coding of mammalian cells using semiconductor quantum dots.", Analytical Biochemistry, 327(2):200-208 (2004).
Maung, et al., "Probing for a hydrophobic a binding register in prostate-specific membrane antigen with phenylalkylphosphonamidates.", Bioorg. Med. Chem., 12 (18):4969-4979 (2004).
McDevitt, et al., "An alpha-particle emitting antibody ([213Bi]J591) for radioimmunotherapy of prostate cancer.", Cancer Res., 60(21):6095-6100 (2000).
McDevitt, et al., "Tumor therapy with targeted atomic nanogenerators.", Science, 294(5546):1537-1540 (2001).
McNeil, "Nanotechnology for the biologist", J Leukoc Biol., 78:575-94 (2005).
Mead, et al., "Laboratory vector competence of black flies (*Diptera simuliidae*) for the Indiana serotype of vesicular stomatitis virus.", Ann. N.Y. Acad. Sci., 916:437-443 (2000).
Meister, et al., "Mechanisms of gene silencing by double-stranded RNA.", Nature, 431(7006):343-349 (2004).
Melani, et al., "Targeting of interleukin 2 to human ovarian carcinoma by fusion with a single-chain Fv of antifolate receptor antibody.", Cancer Res., 58 (18):4146-4154 (1998).
Mempel, et al., "T-cell priming by dendritic cells in lymph nodes occurs in three distinct phases.", Nature, 427(6970):154-159 (2004).
Metelitsa, el al., "Antidisialoganglioside/granulocyte macrophage-colony-stimulating factor fusion protein facilitates neutrophil antibody-dependent cellular cytotoxicity and depends on FcgammaRII (CD32) and Mae-1 (CD11b/CD18) for enhanced effector cell adhesion and azurophil granule exocytosis.", Blood, 99(11):4166-4173 (2002).
Meyers, et al., "Development of monoclonal antibody imaging of metastatic prostatic carcinoma.", Prostate, 14(3):209-220 (1989).
Milligan and Uhlenbeck, "Synthesis of small RNAs using T7 RNA polymerase," Methods in Enzymology, 180: 51-62 (1989).
Mitra, et al., "Tumour targeted delivery of encapsulated dextran-doxorubicin conjugate using chitosan nanoparticles as carrier", J Controlled Release, 74:317-23 (2001).
Mi, et al., "Release of Indomethacin from a Novel Chitosan Microsphere Prepared by a Natrually Occurring Crosslinker:

(56) References Cited

OTHER PUBLICATIONS

Examination of Crosslinking and Polycation-Anionic Drug Interaction", J. of Applied Polymer Science, 81:1700-1711 (2001).
Moghimi, et al., "Long-circulating and target-specific nanoparticles: theory to practice," Pharmacol. Rev., 53(2): 283-318 (2001).
Moon, et al., "Engineering Nano- and microparticles to tune immunity", Adv Mater., DOI:10.1002/adma.201200446 (2012).
Mulligan, "The basic science of gene therapy," Science, 260(5110):926-32 (1993).
Murphy, et al., "isolation and characterization of monoclonal antibodies specific for the extracellular domain of prostate specific membrane antigen.", J. Urol., 160(6 Pt 2):2396-2401 (1998).
Murray, et al., "Synthesis and characterization of monodisperse nanocrystals and close-packed nanocrystal assemblies", Ann. Rev. Mat. Sci., 30:545-610 (2000).
Myers and Miller, Optimal alignments in linear space, CABIOS, 4(1):11-17 (1988).
Nan, et al., "Dual function glutamate-related ligands: discovery of a novel, potent inhibitor of glutamate carboxypeptidase II possessing mGluR3 agonist activity.", J. Med. Chem., 43 (5):772-774 (2000).
Neidle, "The molecular basis for the action of some DNA-binding drugs.", Prog. Med. Chem., 16:151-221 (1979).
Nguyen and Wu, "Micromixers a review.", J. Micromechan. Microeng., 15:R1 (2005).
Notter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
O'Donnell, et al., "c-Myc-regulated microRNAs modulate E2F1 expression," Nature, 435(7043): 839-843 (2005).
Ochsenbein, et al., "Control of early viral and bacterial distribution and disease by natural antibodies.", Science, 286(5447):2156-2159 (1999).
Ochsenbein, et al., "Protective T cell-independent antiviral antibody responses are dependent on complement,", J. Exp. Med., 190(8):1165-1174 (1999).
Okada, et al., "Antigen-engaged B cells undergo chemotaxis toward the T zone and form motile conjugates with helper T cells.", PLoS Biol., 3(6):e150 (2005).
Oliver, et al., "Conformational and SAR analysis of NAALADase and PSMA inhibitors.", Bioorg. Med. Chem., 11(20):4455-4461 (2003).
Olivier, et al., "Drug Transport to Brain with Targeted Nanoparticles", J. of the Am. Society of Experimental NeuroTherapeutics, 2:108-119 (2005).
Oyewumi, et al., "Comparison of cell uptake, biodistribution and tumor retention of folate-coated and PEG-coated gadolinium nanoparticles in tumor-bearing mice", J Control Rel., 93:613-26 (2004).
Oyewumi, et al., "Nano-microparticles as immune adjuvants: correlating particle sizes and the resultant immune responses", Exp Rev Vaccines, 9(9):1095-1107 (2010).
Pape, et al., "The humoral immune response is initiated in lymph nodes by B cells that acquire soluble antigen directly in the follicles.", Immunity, 26 (4):491-502 (2007).
Papisov, "Acyclic Polyacetals from Polysaccharides: Biomimetic Biomedical "Stealth" Polymers", ACS Symposium Series, 786:301-314 (2001).
Parekh, et al., "Biomarkers for Prostate Cancer Detection", The Journal of Urology, 178(6):2252-2259 (2007).
Pasqualini, et al., "Aminopeptidase N is a receptor for tumor-homing peptides and a target for inhibiting angiogenesis.", Cancer Res., 60(3):722-727 (2000).
Patri, et al., "Synthesis and in Vitro Testing of J591 Antibody Dendrimer Conjugates for Targeted Prostate Cancer Therapy", Bioconj. Chem., 15:1174-1181 (2004).
Pellegrino, et al., "On the development of colloidal nanoparticles towards multifunctional structures and their possible use for biological applications.", Small, 1(1):48-63 (2005).

Pfohl, et al., "Trends in microfluidics with complex fluids.", Chemphyschem, 4 (12):1291-1298 (2003).
Phillips, et al., "Enhanced antibody response to liposome-associated protein antigens: preferential stimulation of IgG2a/b production.", Vaccine, 10(3):151-158 (1992).
Pimentel, et al., "Peptide nanoparticles as novel immunogens: design and analysis of a prototypic severe acute respiratory syndrome vaccine", Chemical Biology & Drug Design, 73(1):53-61 (2009).
Ponchel, et al., "Specific and non-specific bioadhesive particulate systems for oral delivery to the gastrointestinal tract", Advanced Drug Delivery Reviews, 34:191-219 (1998).
Porkka, et al., "A fragment of the HMGN2 protein homes to the nuclei of tumor cells and tumor endothelial cells in vivo.", Proc. Natl. Acad. Sci., USA, 99 (11):7444-7449 (2002).
Putnam, et al., "Poly(4-hydroxy-l-proline ester): Low-Temperature Polycondensation and Plasmid DNA Complexation", Macromolecules, 32 (11):3658-3662 (1999).
Qi, et al., "Extrafollicular activation of lymph node B cells by antigen-bearing dendritic cells", Science, 312(5780):1672-1676 (2006).
Quintanar-Guerrero, et al., "Preparation Techniques and Mechanisms of Formation of Biodegradable Nanoparticles from Preformed Polymers", Drug Dev. Industrial Pharmacy, 24(12):1113-1128 (1998).
Reddy, et al., "Exploiting lymphatic transport and complement activation in nanoparticle vaccines", Nat. Biotech., 25(10):1159-1164 (2007).
Reif, et al., "Balanced responsiveness to chemoattractants from adjacent zones determines B-cell position.", Nature, 416(6876):94-99 (2002).
Reiher, et al., "Inhibition of tumor growth by systemic treatment with thrombospondin-1 peptide mimetics.", Int. J. Cancer, 98(5):682-689 (2002).
Reubi, et al., "Peptide receptors as molecular targets for cancer diagnosis and therapy.", Endocr. Rev., 24(4):389-427 (2003).
Reynolds, et al., "Rational siRNA design for RNA interference.", Nat. Biotechnol., 22(3):326-330 (2004).
Riley, et al., "Physicochemical evaluation of nanoparticles assembled from Poly(lactic acid)-Poly(ethylene glycol) (PLA__PEG) block copolymers as drug delivery vehicles", Langmuir, 17:3168-74 (2001).
Riley, et al., "Colloidal stability and drug incorporation aspects of micellar-like PLA-PEG nanoparticles", Colloids Surfaces B Biointerfaces, 16:147-59 (1999).
Robbins, et al., "Stable expression of shRNAs in human CD34+ progenitor cells can avoid induction of interferon responses to siRNAs in vitro", Nature Biotechnology, 24(5):566-571 (2006).
Robinson, et al., "LEAPT: lectin-directed enzyme-activated prodrug therapy.", Proc. Natl. Acad. Sci., USA, 101(40):14527-14532 (2004).
Roost, et al., "Mapping of the dominant neutralizing antigenic site of a virus using infected cells.", J. Immunol. Methods, 189(2):233-242 (1996).
Rossbacher and Shlomchik, "The B cell receptor itself can activate complement to provide the complement receptor 1/2 ligand required to enhance B cell immune responses in vivo.", J. Exp. Med., 198(4):591-602 (2003).
Sampson, et al., "Progress report of a Phase I study of the intracerebral microinfusion of a recombinant chimeric protein composed of transforming growth factor (TGF)-alpha and a mutated form of the Pseudomonas exotoxin termed PE-38 (TP-38) for the treatment of malignant brain tumors.", J. Neurooncol., 65(427-35 (2003).
Santoyo, et al., "Highly specific and accurate selection of siRNAs for high-throughput throughput functional assays.", Bioinformatics, 21(8):1376-1382 (2005).
Sarkar, et al., "Ligand-DNA interaction in a nanocage of reverse micelle", Biopolymer., 83(6):675-86 (2006).
Sarver, et al., "Ribozymes as potential anti-HIV-1 therapeutic agents.", Science 247(4947):1222-1225 (1990).
Schally, et al., "Peptide analogs in the therapy of prostate cancer.", Prostate, 45(2):158-166 (2000).

(56) References Cited

OTHER PUBLICATIONS

Schiffelers, et al., "Cancer siRNA therapy by tumor selective delivery with ligand-targeted sterically stabilized nanoparticle", Nucleic Acids Res., 32(19):1-10 (2004).
Schultz, et al., "Single-target molecule detection with nonbleaching multicolor optical immunolabels.", Proc. Natl. Acad. Sci., USA, 97(3):996-1001(2000).
Schultz, "Plasmon resonant particles for biological detection", Curr. Op. Biotechnol., 14:13-22 (2003).
Shaida, et al., "Expression of BNIP3 correlates with hypoxia-inducible factor (HIF)-1a, HIF-2a and the androgen receptor in prostate cancer and is regulated directly by hypoxia but not androgens in cell lines", The Prostate, 68(3):336-343 (2008).
Shen, et al. 'Enhanced and Prolonged Cross-Presentation Following Endosomal Escape of Exogenus Antigens Encapsulated in Biodegradable Nanoparticles' Immunology. 117(1):78-88 (2006).
Shestopalov, et al., "Multi-step synthesis of nanoparticles performed on millisecond time scale in a microfluidic droplet-based system.", Lab on a Chip, 4 (4):316-321 (2004).
Shields, et al., "High resolution mapping of the binding site on human IgGI for Fc gamma RI, Fc gamma RII, Fc gamma RIII, and FcRn and design of IgG1 variants with improved binding to the Fc gamma R", J Biolo Chem., 276(9):6591-6604 (2001).
Shim, "One target different effects: a comparison of distinct therapeutic antibodies against the same targets", Exp Mole Med.,43(10):539-49 (2011).
Shimoda, et al., "Bioadhesive Characteristics of Chitosan Mircroshperes to the Mucosa of Rat Small Intestine", Drug Delvelopment and Inustrial Pharmacy, 27 (6):567-576 (2001).
Shiow, et al., "CD69 acts downstream of interferon-alpha/beta to inhibit S1P1 and lymphocyte egress from lymphoid organs.", Nature, 440(7083):540-544 (2006).
Silver, et al., "Prostate-specific membrane antigen expression in normal and malignant human tissues.", Clin. Cancer Res., 3(1):81-85 (1997).
Simberg, et al., "Biomimetic amplification of nanoparticle homing to tumors", Nat\l. Acad. Sic. USA, 104(3):921-936 (2007).
Smith-Jones, et al., "In vitro characterization of radiolabeled monoclonal antibodies specific for the extracellular domain of prostate-specific membrane antigen.", Cancer Res., 60(18):5237-5243 (2000).
Sondel, et al., "Preclinical and clinical development of immunocytokines.", Curr. Opin. Investig. Drugs, 4(6):696-700 (2003).
Song, et al., "A Microfluidic System for Controlling Reaction Networks in Time", Angewandte Chemie—Int'l Ed., 42:768-772 (2003).
Spooner, et al., "A novel vascular endothelial growth factor-directed therapy that selectively activates cytotoxic prodrugs.", Br. J. Cancer, 88(10):1622-1630 (2003).
Stoermer, et al., "Synthesis and biological evaluation of hydroxamate-Based inhibitors of glutamate carboxypeptidase II.", Bioorg. Med. Chem. Lett., 13 (13):2097-2100 (2003).
Storm, et al., "Surface Modification of Nanoparticles to Oppose Uptake by the Mononuclear Phagocyte System", Adv. Drug Deliv. Rev., 17:31-48 (1995).
Stroock, et al., "Chaotic mixer for microchannels.", Science, 295 (5555):647-651 (2002).
Sutcliffe, et al., "Antibodies that react with predetermined sites on proteins", Science, 219:660-666 (1983).
Suzuki, et al., "Development of effective antigen delivery carrier to dendritic cells via Fc receptor in cancer immunotherapy",Yakugaku Zasshi, 127(2):301-6 (2007). English Abstract.
Takeuchi, et al., "Enteral Absorption of Insulin in Rats from Mucoadhesive Chitosan-Coated Liposomes", Pharmaceutical Research, 13(6):896-901 (1996).
Takeuchi, et al., "Spray-Dried Lactose Composite Particles Containing an Ion Complex of Alginate-Chitosan for Desinging a Dry-Coated Tablet Having a Time-Controlled Releasing Function", Pharmaceutical Research, 17 (1):94-99 (2000).
Takeuchi et al., "Mucoashesive Lipsomes Coated with Chitosan or Carbopol for Oral Administration of Peptide Drugs", Proceed. Intl. Symp. Control. Rel. Bioact. Mater., 26:988-989 (1999).
Tang, et al., "In Vitro Gene Delivery by Degraded Polyamidoamine Dendrimers", Bioconjugate Chem., 7:703-714 (1996).
Tang, et al., "Prostate targeting ligands based on N-acetylated alpha-linked acidic dipeptidase.", Biochem. Biophys. Res. Commun., 307(1):8-14 (2003).
Tavitian, et al., "In vivo imaging with oligonucleotides for diagnosis and drug development", Gut, 52 Su, I IV :40-47 (2003).
Taylor, et al., "Development of a specific system for targeting protein to metallophilic macrophages", PNAS, 101(7):1963-8 (2004).
Taylor, et al., "Macrophage receptors and immune recognition.", Annu. Rev. Immunol, 23:901-944 (2005).
Tindall, et al, "The Rationale for Inhibiting 5a-Reductase Isoenzymes in the Prevention and Treatment of Prostate Cancer", The Journal of Urology, 179 (4):1235-1242 (2008).
Tobio, et al,"Role of PEG on the stability in digestive fluids and in vivo fate of PEG-PLA nanoparticles following oral administration", Colloids and Surfaces B: Biointerferences, 18:315-323 (2000).
Tomai, et al., "Resiquimod and other immune response modifiers as vaccine adjuvants", Expert Rev Vaccines, 6:835-847 (2007) Abstract Only.
Trindade, et al., "Nanocrystalline Semiconductors: Synthesis, Properties, and Perspectives", Chem. Mat., 13(11):3843-3858 (2001).
Tsukamoto, et al., "Phosphonate and phosphinate analogues of N-acylated gamma-glutamylglutamate. potent inhibitors of glutamate carboxypeptidase II.", Bioorg. Med. Chem. Lett., 12(16):2189-2192 (2002).
Uhrich, et al., "Polymeric Systems for Controlled Drug Release", Chem. Rev., 99(11):3181-3198 (1999).
Unkeless, et al., "Structure and function of human and murine receptors for IgG.", Annu. Rev. Immunol., 6:251-281 (1998).
Uto, et al., "Targeting of antigen to dendritic cells with poly(gamma-glutamic acid) nanoparticles induces antigen-specific humoral and cellular immunity", J Immunology, 178 (5):2979-86 (2007).
Uwatoku, et al., "Application of Nanoparticle Technology for the Prevention of Restenosis After Balloon Injury in Rats," Circ. Res., 92(7): e62-9 (2003).
Valentini, et al., "Association of anthracycline derivatives with DNA: a fluorescence study.", Farmaco [Sci], 40:377-390 (1985).
Vallabhajosula, et al., "Radioimmunotherapy of prostate cancer in human xenografts using monoclonal antibodies specific to prostate specific membrane antigen (PSMA): studies in nude mice.", Prostate, 58(2):145-155 (2004).
Vascotto, et al., "Antigen presentation by B lymphocytes: how receptor signaling directs membrane trafficking.", Curr., Opin., Immunol., 19(1):93-98 (2007).
Vihko, et al., "Radioimaging of Prostatic Carcinoma With Prostatic Acid Phosphatase—Specific Antibodies", Biotechnology in Diagnostics, 131-134 (1985).
Vila, et al., "Design of biodegradable particles for protein delivery", Journal of Controlled Release, 78:15-24 (2002).
Vila, et al., "PLA-PEG Nanospheres: New Carriers for Transmucosal Delivery of Proteins and Plasmid DNA", Poly. Adv. Technol., 13:851-858 (2002).
Villa, et al., "PLA-PEG particles as nasal protein carriers: the influence of the particle size", Int. J Pharmaceut., 292:43-52 (2005).
Von Allmen, et al., "V domain of RAGE interacts with AGEs on prostate carcinoma cells", The Prostate, 68(7):748-758 (2008).
Von Andrian and Mempel, "Homing and cellular traffic in lymph nodes.", Nat. Rev. Immunol., 3(11):867-878 (2003).
Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).
Wang, et al., "A novel biodegradable gene carrier based on polyphosphoester.", J. Am. Chem. Soc., 123(38):9480-9481 (2001).
Wang, et al., "Autoantibody signatures in prostate cancer.", N Engl J Med, 353 (12):1224-1235 (2005).

(56) References Cited

OTHER PUBLICATIONS

Wang, et al., "Identification of prostate specific membrane antigen (PSMA) as the target of monoclonal antibody 107-1A4 by proteinchip; array, surface-enhanced laser desorption/ionization (SELDI) technology.", Int. J. Cancer, 92(6):871-876 (2001).
Wang, et al., "Interactions between an anthracycline antibiotic and DNA: molecular structure of daunomycin complexed to d(CpGpTpApCpG) at 1.2-A resolution,", Biochemistry, 26(4):1152-1163 (1987).
Weaver, et al., "Transferrin receptor ligand-targeted toxin conjugate (Tf-CRM107) for therapy of malignant gliomas.", J. Neurooncol., 65(1):3-13 (2003).
Wessels, et al., "Studies of group B streptococcal infection in mice deficient in complement component C3 or C4 demonstrate an essential role for complement in both innate and acquired immunity.", Proc. Natl. Acad. Sci., USA, 92(25):11490-11494 (1995).
Whelan, et al., "Efficient recovery of infectious vesicular stomatitis virus entirely from cDNA clones.", Proc. Natl. Acad. Sci., USA, 92(18):8388-8392 (1995).
Wilson, et al., "The Structure of an Antigenic Determinant in a Protein", Cell, 37:767-778 (1984).
Wind, et al., "An integrated confocal and magnetic resonance microscope for cellular research.", J. Magn. Reson., 147(2):371-377 (2000).
Wlotzka, et al., "In vivo properties of an anti-GnRH Spiegelmer: an example of an oligonucleotide-based therapeutic substance class," Proc. Natl. Acad. Sci. U. S. A., 99 (13):8898-902 (2002).
Wright, et al., "Cyclophosphamide/granulocyte colony-stimulating factor causes selective mobilization of bone marrow hematopoietic stem cells into the blood after M phase of the cell cycle.", Blood, 97(8):2278-2285 (2001).
Wu, et al., "Immunofluorescent labeling of cancer marker Her2 and other cellular targets with semiconductor quantum dots.", Nat. Biotechnol., 21(1):41-46 (2003).
Wu, et al., Selection of oligonucleotide apatamers with enhanced uptake and activation of human leukemia B cells Human Gene., 14:849-860 (2003).
Wu, "Arming antibodies: prospects and challenges for immunoconjugates.", Nat. Biotechnol., 23(9):1137-1146 (2005).
Yamada, et al., "In Vitro and in Vivo Evaluation of Sustained Release Chitosan-Coat Ketoprofen Microparticles", Yakugaku Zasshi, 121(3):239-245 (2001).
Yang, et al., "Micelles formed by self-assmbling of polylactide(ethylene glycol) block copolymers in aqueous solutions", J Colloid interfac Si., 314:470-77 (2007).
Yang, "Imaging of vascular gene therapy.", Radiology, 228:36-249 (2003).
Yoo, et al., "In vitro and in vivo anti-tumor activities of nanoparticles based on doxorubicin-PLGA conjugates.", J. Control. Release, 68(3):419-431 (2000).
Yourong, et al., "Preparation of DHAQ-loaded mPEG-PLGA-mPEG nanoparticles and evaluation of drug release behaviors in vitro/in vivo," J. Mat. Sci.: Mat. Med., 17(6): 509-16 (2006).
Yu, et al., "Engineered bio-nanocapsules, the selective vector for drug delivery system", IUBMB Like, 58(1):1-6 (2006).
Yuan, et al. 'Intranasal Immunization with Chitosan/pCETP Nanoparticles inhibits Atherosclerosis in a Rabbit Model of Atherosclerosis' Vaccine. 26 (29-30):3727-3734 (2008).
Yuan, et al., "siRNA Selection Server: an automated siRNA oligonucleotide prediction server.", Nucl. Acids. Res., 32:W130-W134 (2004).
Zamore, et al., "RNAi: double-stranded RNA directs the ATP-dependent cleavage of mRNA at 21 to 23 nucleotide intervals.", Cell, 101(1):25-33 (2000).
Zauner, et al., "Polylysine-basedtransfection systems utilizing receptor-mediated mediated delivery.", Adv. Drug Del. Rev., 30:97-113 (1998).
Zhang, et al., "The proliferative effect of estradiol on human prostate stromal cells is mediated through activation of ERK", The Prostate, 68(5):508-516 (2008).
Zheng, et al., "Highly fluorescent, water-soluble, size-tunable gold quantum dots.", Phys. Rev. Lett., 93(7):077402 (2004).
Zhou, et al., "Investigation on a novel core-coated microspheres protein delivery system.", J. Control. Release, 75(1-2):27-36 (2001).
Zhou, et al., "NAAG peptidase inhibitors and their potential for diagnosis and therapy", Nature Rev. Drug Disc., 4:1015-26 (2005).
Zhou, et al., "Preparation of poly(L-serine ester): a structural analog of conventional poly(L-serine)", Macromolecules, 23(14):3399-3406 (1990).
Zuker, "Mfold web server for nucleic acid folding and hybridization prediction", Nuc. Acid. Res., 31:3406-3415 (2003).

* cited by examiner

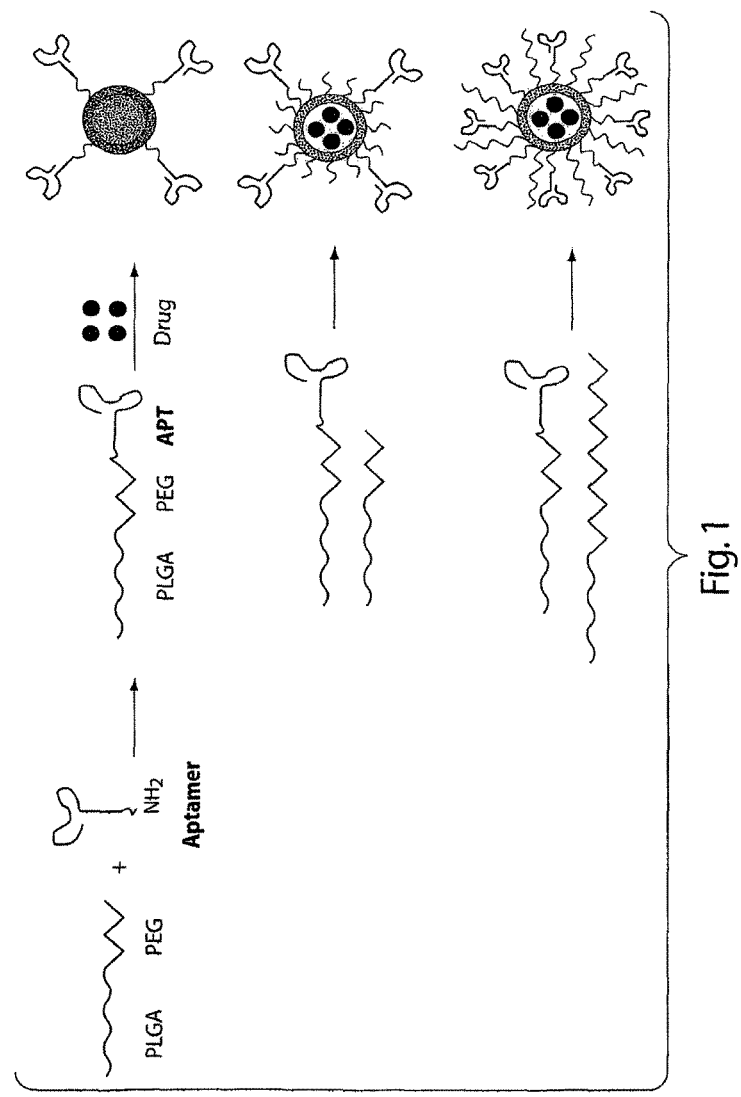

POLYMERS FOR FUNCTIONAL PARTICLES

RELATED APPLICATIONS

This application is a continuation of pending application U.S. Ser. No. 13/673,354, filed Nov. 9, 2012 entitled "Polymers For Functional Particles," by Frank X. Gu, Omid C. Farokhzad, Robert S. Langer and Benjamin A. Teply, which is a divisional of U.S. Ser. No. 12/873,692, filed Sep. 1, 2010, now U.S. Pat. No. 8,323,698, which is a divisional of U.S. Ser. No. 11/803,843, filed May 15, 2007, now U.S. Pat. No. 8,367,113 and claims the benefit of and priority to U.S. Provisional Patent Application Ser. No. 60/747,240, filed May 15, 2006, all of which are incorporated herein in their entirety by reference.

STATEMENT OF GOVERNMENT SUPPORT

This invention was made with Government Support under Grant Nos. EB003647 and CA119349 awarded by the National Institutes of Health. The government has certain rights in the invention.

REFERENCE TO SEQUENCE LISTING

The Sequence Listing submitted on Feb. 13, 2015, as a text file named "MIT_12176_DIV_2_CON_ST25.txt," created on Feb. 3, 2015, and having a size of 611 bytes is hereby incorporated by reference pursuant to 37 C.F.R. §1.52(e)(5).

FIELD OF INVENTION

The present invention generally relates to polymers and macromolecules and, in particular, to block polymers useful in particles such as nanoparticles.

BACKGROUND

The delivery of a drug to a patient with controlled-release of the active ingredient has been an active area of research for decades and has been fueled by the many recent developments in polymer science and the need to deliver more labile pharmaceutical agents such as nucleic acids, proteins, and peptides. In addition, controlled release polymer systems can be designed to provide a drug level in the optimum range over a longer period of time than other drug delivery methods, thus increasing the efficacy of the drug and minimizing problems with patient compliance.

Biodegradable particles have been developed as sustained release vehicles used in the administration of small molecule drugs as well as protein and peptide drugs and nucleic acids. The drugs are typically encapsulated in a polymer matrix which is biodegradable and biocompatible. As the polymer is degraded and/or as the drug diffuses out of the polymer, the drug is released into the body. Typically, polymers used in preparing these particles are polyesters such as poly (lactide-co-glycolide) (PLGA), polyglycolic acid, poly-beta-hydroxybutyrate, polyacrylic acid ester, etc. These particles can also protect the drug from degradation by the body. Furthermore, these particles can be administered using a wide variety of administration routes.

Targeting controlled release polymer systems (e.g., targeted to a particular tissue or cell type or targeted to a specific diseased tissue but not normal tissue) is desirable because it reduces the amount of a drug present in tissues of the body that are not targeted. This is particularly important when treating a condition such as cancer where it is desirable that a cytotoxic dose of the drug is delivered to cancer cells without killing the surrounding non-cancerous tissue. Effective drug targeting should reduce the undesirable and sometimes life threatening side effects common in anticancer therapy.

SUMMARY OF THE INVENTION

The present invention generally relates to polymers and macromolecules and, in particular, to block polymers useful in particles such as nanoparticles. The subject matter of the present invention involves, in some cases, interrelated products, alternative solutions to a particular problem, and/or a plurality of different uses of one or more systems and/or articles.

In one aspect, the present invention is directed to a method. In one set of embodiments, the method is a method of developing nanoparticles with desired properties. According to a first embodiment, the method includes acts of providing a first macromolecule comprising a first biocompatible polymer and a moiety selected from the group consisting of a targeting moiety, an imaging moiety, a chelating moiety, a moiety having multiple charge groups, and a therapeutic moiety; providing a second macromolecule comprising a second biocompatible polymer; producing a library of nanoparticles having different ratios of the first and second macromolecules by forming nanoparticles from mixtures comprising the first and second macromolecules at different ratios; and identifying a nanoparticle from the library of nanoparticles having one or more desired properties.

The method, in another embodiment, includes acts of providing a first macromolecule comprising a first block having a repeat unit and a second block comprising a moiety selected from the group consisting of a targeting moiety, an imaging moiety, a chelating moiety, a moiety having multiple charge groups, and a therapeutic moiety; providing a second polymer comprising the first repeat unit but not comprising the targeting moiety; and producing a library of nanoparticles having different ratios of the first macromolecule and second polymer by forming nanoparticles from mixtures comprising the first macromolecule and the second polymer at different ratios.

In yet another embodiment, the method includes acts of providing a first biocompatible hydrophobic polymer; providing a second biocompatible hydrophilic polymer; providing a moiety selected from the group consisting of a targeting moiety, an imaging moiety, a chelating moiety, a moiety having multiple charge groups, and a therapeutic moiety; reacting the first biocompatible hydrophobic polymer, the second biocompatible hydrophilic polymer, and the moiety to produce a macromolecule; producing a library of nanoparticles comprising the macromolecule and at least one other polymer by forming nanoparticles from mixtures comprising the macromolecule and the at least one other polymer at different ratios; and identifying a nanoparticle from the library of nanoparticles having one or more desired properties In accordance with still another embodiment, the method includes acts of providing a biocompatible hydrophilic polymer; providing a moiety selected from the group consisting of a targeting moiety, an imaging moiety, a chelating moiety, a moiety having multiple charge groups, and a therapeutic moiety; reacting the biocompatible hydrophilic polymer and the moiety to produce a macromolecule; producing a library of nanoparticles comprising the macromolecule and at least one other polymer by forming nanoparticles from mixtures comprising the macromolecule and the at least one other polymer at different ratios; and identifying a nanoparticle from the library of nanoparticles having one or more desired properties.

The method, in one embodiment, includes acts of providing a biocompatible hydrophobic polymer; providing a moiety selected from the group consisting of a targeting moiety, an imaging moiety, a chelating moiety, a moiety having multiple charge groups, and a therapeutic moiety; reacting the biocompatible hydrophobic polymer and the moiety to produce a macromolecule; producing a library of nanoparticles comprising the macromolecule and at least one other polymer by forming nanoparticles from mixtures of the macromolecule and the at least one other polymer at different ratios; and identifying a nanoparticle from the library of nanoparticles having one or more desired properties.

In another set of embodiments, the method includes acts of providing a first macromolecule comprising a biocompatible hydrophobic polymer, a biocompatible hydrophilic polymer, and a moiety selected from the group consisting of a targeting moiety, an imaging moiety, a chelating moiety, a moiety having multiple charge groups, and a therapeutic moiety; providing a second macromolecule comprising the biocompatible hydrophobic polymer, the second macromolecule having a polymeric portion distinguishable from the polymer portion of the first macromolecule; producing a library of nanoparticles having different ratios of the first and second macromolecules by forming nanoparticles from mixtures of the first and second macromolecules at different ratios; and identifying a nanoparticle from the library of nanoparticles having one or more desired properties.

In still another set of embodiments, the method includes acts of providing a first macromolecule comprising a biocompatible hydrophobic polymer, a biocompatible hydrophilic polymer, and a moiety selected from the group consisting of a targeting moiety, an imaging moiety, a chelating moiety, a moiety having multiple charge groups, and a therapeutic moiety; providing a second macromolecule comprising the biocompatible hydrophobic polymer and the biocompatible hydrophilic polymer, the second macromolecule having a polymeric portion distinguishable from the polymer portion of the first macromolecule; producing a library of nanoparticles having different ratios of the first and second macromolecules by forming nanoparticles from mixtures of the first and second macromolecules at different ratios; and identifying a nanoparticle from the library of nanoparticles having one or more desired properties.

According to yet another embodiment, the method includes acts of providing a first macromolecule comprising a biocompatible hydrophobic polymer and a biocompatible hydrophilic polymer; providing a second macromolecule comprising the biocompatible hydrophobic polymer and a moiety selected from the group consisting of a targeting moiety, an imaging moiety, a chelating moiety, a moiety having multiple charge groups, and a therapeutic moiety, the second macromolecule having a polymeric portion distinguishable from the polymer portion of the first macromolecule; producing a library of nanoparticles having different ratios of the first and second macromolecules by forming nanoparticles from mixtures of the first and second macromolecules at different ratios; and identifying a nanoparticle from the library of nanoparticles having one or more desired properties.

In another set of embodiments, the method is a method of producing a library. According to one embodiment, the method includes acts of providing a first block copolymer comprising a biocompatible polymer, a poly(alkylene glycol), and a moiety selected from the group consisting of a targeting moiety, an imaging moiety, a chelating moiety, a moiety having multiple charge groups, and a therapeutic moiety; providing a second polymer comprising a block copolymer comprising a biocompatible polymer and a poly(alkylene glycol) and having a polymeric portion distinguishable from the polymeric portion of the first polymer; and producing a library of nanoparticles having different ratios of the first and second polymers by forming nanoparticles from mixtures of the first and second polymers at different ratios.

According to another embodiment, the method includes acts of providing a first block copolymer comprising first and second polymers; providing a second block copolymer comprising the first and second polymers and further comprising a moiety selected from the group consisting of a targeting moiety, an imaging moiety, a chelating moiety, a moiety having multiple charge groups, and a therapeutic moiety; and producing a library of nanoparticles having different ratios of the first and second polymers by forming nanoparticles from mixtures of the first and second polymers at different ratios.

The method, in one set of embodiments, includes acts providing an solution comprising an amphiphilic macromolecule comprising a repeat unit and a moiety selected from the group consisting of a targeting moiety, an imaging moiety, a chelating moiety, a moiety having multiple charge groups, and a therapeutic moiety; and contacting the solution with a polymer nonsolvent to produce particles comprising the amphiphilic macromolecule, the particles having an average characteristic dimension of less than about 1 micrometer. In another set of embodiments, the method includes acts of providing a solution comprising a first block copolymer and a second block copolymer; and contacting the solution with a polymer nonsolvent to produce particles particle having an average characteristic dimension of less than about 1 micrometer. In still another set of embodiments, the method includes acts of providing a solution comprising a polymer comprising a biocompatible polymer, a poly(alkylene glycol), and a moiety selected from the group consisting of a targeting moiety, an imaging moiety, a chelating moiety, a moiety having multiple charge groups, and a therapeutic moiety; and contacting the solution with a polymer nonsolvent to produce particles having an average characteristic dimension of less than about 1 micrometer.

In accordance with yet another set of embodiments, the method includes an act of reacting a carboxylic acid-terminated poly(ester-ether) copolymer with a moiety selected from the group consisting of a targeting moiety, an imaging moiety, a chelating moiety, a moiety having multiple charge groups, and a therapeutic moiety, the moiety comprising an amine, without using N-hydroxysuccinimide to produce a block copolymer.

The method, in still another set of embodiments, includes in a single reaction, an act of reacting a carboxylic acid-terminated poly(ester-ether) copolymer with a moiety selected from the group consisting of a targeting moiety, an imaging moiety, a chelating moiety, a moiety having multiple charge groups, and a therapeutic moiety, the targeting moiety comprising an amine, to produce a block copolymer.

In another aspect, the present invention is directed to a composition. In one set of embodiments, the composition comprises a particle having an average characteristic dimension of less than about 1 micrometer, where the particle comprises a macromolecule comprising a first portion comprising a biocompatible polymer and a second portion comprising a moiety selected from the group consisting of a targeting moiety, an imaging moiety, a chelating moiety, a moiety having multiple charge groups, and a therapeutic moiety. In some cases, the moiety has an essentially nonzero concentration internally of the particle.

According to another set of embodiments, the composition includes a particle having an average characteristic dimension of less than about 1 micrometer, where the particle includes a first macromolecule and a second macromolecule. In some cases, the first macromolecule is a block copolymer comprising a first biocompatible polymer, a poly(alkylene glycol), and a moiety selected from the group consisting of a targeting moiety, an imaging moiety, a chelating moiety, a moiety having multiple charge groups, and a therapeutic moiety. In certain instances, the second macromolecule is a block copolymer comprising a poly(alkylene glycol) and a second biocompatible polymer distinguishable from the first biocompatible polymer In yet another set of embodiments, the composition includes a particle having an average characteristic dimension of less than about 1 micrometer, where the particle has a surface comprising a first macromolecule and a second macromolecule. In some cases, the first macromolecule comprises a first poly(alkylene glycol) chain having a first length and a moiety selected from the group consisting of a targeting moiety, an imaging moiety, a chelating moiety, a moiety having multiple charge groups, and a therapeutic moiety, and the second macromolecule comprises a second poly(alkylene glycol) chain having a second length different from the first length.

The composition, in accordance with one set of embodiments, includes a particle, having an average characteristic dimension of less than about 1 micrometer, comprising a first macromolecule comprising a first biocompatible polymer and a moiety selected from the group consisting of a targeting moiety, an imaging moiety, a chelating moiety, a moiety having multiple charge groups, and a therapeutic moiety, and a second macromolecule comprising a second biocompatible polymer. In some cases, the particle is chosen from a library of nanoparticles having different ratios of the first and second macromolecules.

In another set of embodiments, the composition includes a particle, having an average characteristic dimension of less than about 1 micrometer, comprising a macromolecule comprising a first biocompatible hydrophobic polymer, a second biocompatible hydrophilic polymer, and a moiety selected from the group consisting of a targeting moiety, an imaging moiety, a chelating moiety, a moiety having multiple charge groups, and a therapeutic moiety. The particle may further comprise at least one other polymer. The particle, in some cases, may be chosen from a library of nanoparticles having different ratios of the macromolecule and the at least one other polymer.

In yet another set of embodiments, the composition includes a particle, having an average characteristic dimension of less than about 1 micrometer, comprising a macromolecule comprising a biocompatible hydrophilic polymer and a moiety selected from the group consisting of a targeting moiety, an imaging moiety, a chelating moiety, a moiety having multiple charge groups, and a therapeutic moiety. In some cases, the particle further comprises at least one other polymer. In addition, the particle may be chosen from a library of nanoparticles having different ratios of the macromolecule and the at least one other polymer.

The composition, in still another set of embodiments, includes a particle, having an average characteristic dimension of less than about 1 micrometer, comprising a macromolecule comprising a biocompatible hydrophobic polymer and a moiety selected from the group consisting of a targeting moiety, an imaging moiety, a chelating moiety, a moiety having multiple charge groups, and a therapeutic moiety. In one embodiment, the particle further comprising at least one other polymer, and in some cases, the particle is chosen from a library of nanoparticles having different ratios of the macromolecule and the at least one other polymer.

In one set of embodiments, the composition includes a particle, having an average characteristic dimension of less than about 1 micrometer, comprising a first macromolecule comprising a biocompatible hydrophobic polymer, a biocompatible hydrophilic polymer, and a moiety selected from the group consisting of a targeting moiety, an imaging moiety, a chelating moiety, a moiety having multiple charge groups, and a therapeutic moiety, and a second macromolecule comprising the biocompatible hydrophobic polymer. The second macromolecule may have, in some cases, a polymeric portion distinguishable from the polymer portion of the first macromolecule. In certain instances, the particle is chosen from a library of nanoparticles having different ratios of the first and second macromolecules.

In another set of embodiments, the composition includes a particle, having an average characteristic dimension of less than about 1 micrometer, comprising a first macromolecule comprising a biocompatible hydrophobic polymer, a biocompatible hydrophilic polymer, and a moiety selected from the group consisting of a targeting moiety, an imaging moiety, a chelating moiety, a moiety having multiple charge groups, and a therapeutic moiety, and a second macromolecule comprising the biocompatible hydrophobic polymer and the biocompatible hydrophilic polymer. In one embodiment, the second macromolecule has a polymeric portion distinguishable from the polymer portion of the first macromolecule. In some cases, the particle is chosen from a library of nanoparticles having different ratios of the first and second macromolecules.

The composition, in yet another set of embodiments, includes a particle, having an average characteristic dimension of less than about 1 micrometer, comprising a first macromolecule comprising a biocompatible hydrophobic polymer and a biocompatible hydrophilic polymer, and a second macromolecule comprising the biocompatible hydrophobic polymer and a moiety selected from the group consisting of a targeting moiety, an imaging moiety, a chelating moiety, a moiety having multiple charge groups, and a therapeutic moiety. In some cases, the second macromolecule has a polymeric portion distinguishable from the polymer portion of the first macromolecule. In one embodiment, the particle is chosen from a library of nanoparticles having different ratios of the first and second macromolecules.

In still another set of embodiments, the composition includes a particle having an average characteristic dimension of less than about 1 micrometer, comprising a polymer comprising a first component comprising a biocompatible polymer suitable for drug encapsulation, a second component comprising a polymeric material for decreasing immunogenicity, and a third component comprising a moiety selected from the group consisting of a targeting moiety, an imaging moiety, a chelating moiety, a moiety having multiple charge groups, and a therapeutic moiety. In one embodiment, the third component has an essentially nonzero concentration internally of the particle.

According to yet another set of embodiments, the composition includes a particle having an average characteristic dimension of less than about 1 micrometer, produced using a macromolecule comprising a first component comprising a biocompatible polymer suitable for drug encapsulation, a second component comprising a polymeric material for decreasing immunogenicity, and a third component comprising a moiety selected from the group consisting of a targeting moiety, an imaging moiety, a chelating moiety, a moiety having multiple charge groups, and a therapeutic moiety. In one embodiment, the particle is produced by a method comprising providing a solution comprising the macromolecule, and contacting the solution with a polymer nonsolvent to produce the particle.

In another set of embodiments, the composition includes a particle having an average characteristic dimension of less than about 1 micrometer, comprising a biocompatible polymer and a moiety selected from the group consisting of a targeting moiety, an imaging moiety, a chelating moiety, a moiety having multiple charge groups, and a therapeutic moiety. In some cases, the moiety is contained within the particle and covalently bonded to the biocompatible polymer.

In another aspect, the present invention is directed to a method of making one or more of the embodiments described herein, for example, nanoparticles such as those described herein. In another aspect, the present invention is directed to a method of using one or more of the embodiments described herein, for example, nanoparticles such as those described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 is a schematic diagram illustrating a method of producing libraries of nanoparticles having highly controlled properties, in accordance with one embodiment of the invention;

FIGS. 5A-5C illustrate the in vitro targeting of an aptamer-containing nanoparticle, produced in yet another embodiment of the invention;

DETAILED DESCRIPTION

Figure 2A:
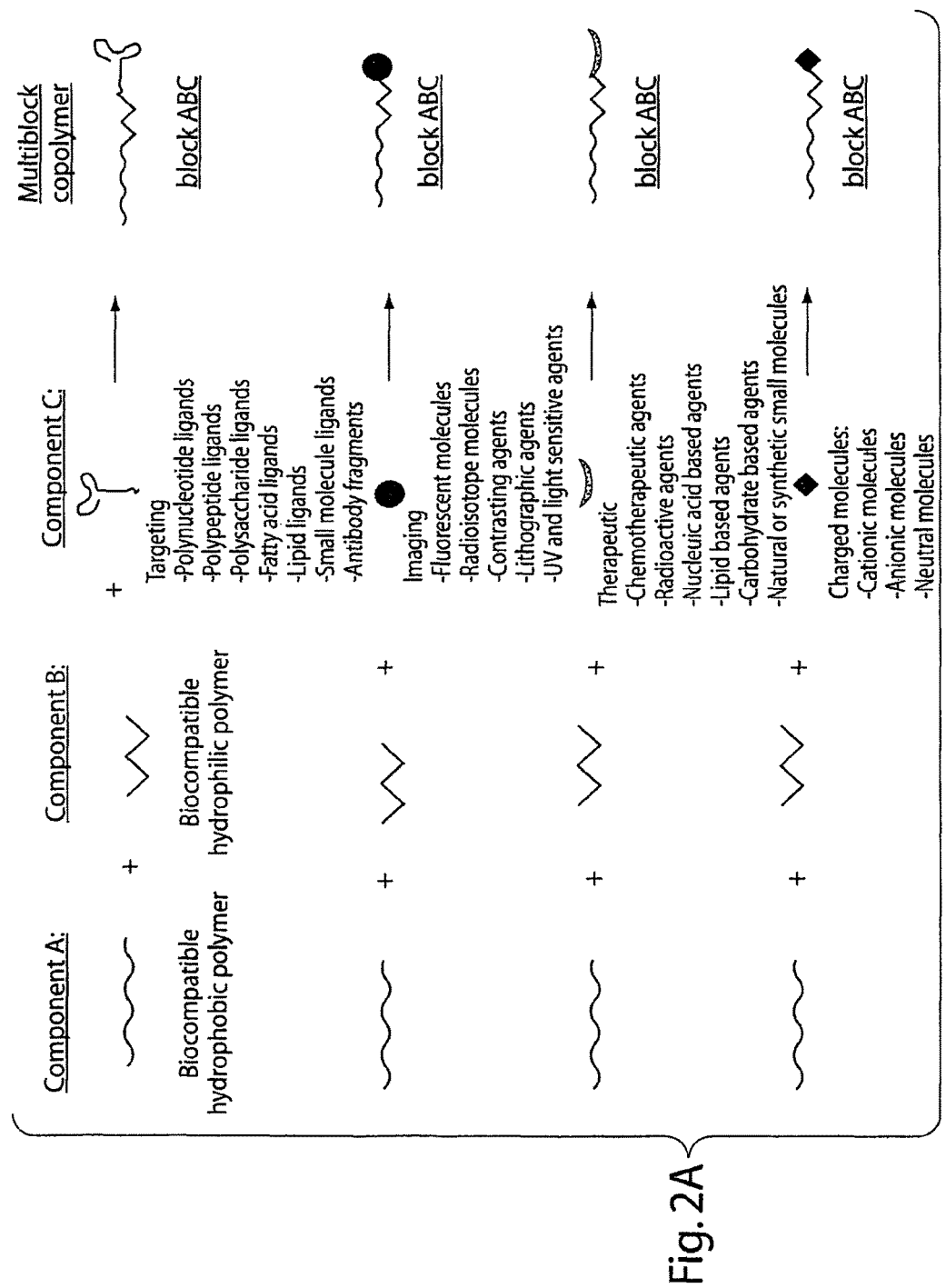
FIG. 2A-2C illustrate schematic diagrams of various polymers of certain embodiments of the present invention, useful for producing particles.

The present invention generally relates to polymers and macromolecules, in particular, to block polymers useful in particles such as nanoparticles. One aspect of the invention is directed to a method of developing nanoparticles with desired properties. In one set of embodiments, the method includes producing libraries of nanoparticles having highly controlled properties, which can be formed by mixing together two or more macromolecules in different ratios. One or more of the macromolecules may be a polymeric conjugate of a moiety to a biocompatible polymer. In some cases, the nanoparticle may contain a drug. The moiety, in some embodiments, may have a molecular weight greater than about 1000 Da; for example, the moiety may include a polypeptide or a polynucleotide, such as an aptamer. The moiety may also be a targeting moiety, an imaging moiety, a chelating moiety, a moiety having multiple charge groups, or a therapeutic moiety. Another aspect of the invention is directed to systems and methods of producing such polymeric conjugates. In some embodiments, a solution containing a polymer is contacted with a liquid, such as an immiscible liquid, to form nanoparticles containing the polymeric conjugate. Other aspects of the invention are directed to methods using such libraries, methods of using or administering such polymeric conjugates, methods of promoting the use of such polymeric conjugates, kits involving such polymeric conjugates, or the like.

As mentioned, one aspect of the invention is directed to a method of developing nanoparticles with desired properties, such as desired chemical, biological, or physical properties. In one set of embodiments, the method includes producing libraries of nanoparticles having highly controlled properties, which can be formed by mixing together two or more macromolecules in different ratios. By mixing together two or more different macromolecules in different ratios and producing particles from the macromolecules, particles having highly controlled properties may be formed. For example, one macromolecule may include a moiety such as a targeting moiety, an imaging moiety, a chelating moiety, a moiety having multiple charge groups, a neutral moiety, or a therapeutic moiety (as discussed in detail below), while another macromolecule may be chosen for its biocompatibility and/or its ability to control immunogenicity of the resultant particle. In some cases, one or more of these macromolecules may be copolymers, as discussed below.

By creating a library of such particles, particles having any desirable properties may be identified. For example, properties such as surface functionality, surface charge, size, zeta (ζ) potential, hydrophobicity, ability to control immunogenicity, and the like, may be highly controlled. For instance, a library of particles may be synthesized, and screened to identify the particles having a particular ratio of polymers or macromolecules that allows the particles to have a specific density of moieties (e.g., therapeutic moieties) present on the surface of the particle. This allows particles having one or more specific properties to be prepared, for example, a specific size and a specific surface density of moieties, without an undue degree of effort. Accordingly, certain embodiments of the invention are directed to screening techniques using such libraries, as well as any particles identified using such libraries. In addition, identification may occur by any suitable method. For instance, the identification may be direct or indirect, or proceed quantitatively or qualitatively.

As a specific, non-limiting example, one embodiment is shown schematically in FIG. 1. In this figure, a first polymer (PLGA-PEG, poly(lactide-co-glycolide) and poly(ethylene glycol)) is conjugated to a targeting moiety (an aptamer, "Apt") to form a PLGA-PEG-Apt macromolecule. The first macromolecule is mixed with a second macromolecule (PLGA-PEG in this example) at varying ratios to form a series of particles having different properties, for example, different surface densities of aptamer as shown in this example. For example, by controlling parameters such as PLGA molecular weight, the molecular weight of PEG, the aptamer surface density, and the nanoparticle surface charge, very precisely controlled particles may be obtained.

More generally, the polymers or macromolecules chosen to be used to create the library of particles may be any of a wide variety of polymers or macromolecules, such as described in detail below. Generally, two, three, four, or more polymers and/or macromolecules are mixed, in a wide range of ratios (e.g., each ranging from 0% to 100%), to form particles such as nanoparticles having different ratios of each of the polymers or macromolecules. The two or more macromolecules may be distinguishable in some fashion, e.g., having different polymeric groups, having the same polymeric groups but with different molecular weights, having some polymeric groups in common but having others that are different (e.g., one may have a polymeric group that the other does not have), having the same polymeric groups but in different orders, etc. The library of particles may have any number of members, for example, the library may have 2, 3, 5, 10, 30, 100, 300, 1000, 3000, 10,000, 30,000, 100,000, etc. members, which can be identified in some fashion. In some cases, the library may exist contemporaneously; for example, the library may be contained in one or more microliter plates, vials, etc., or in some embodiments, the library may have include members created at different times.

The library of particles can then be screened in some fashion to identify those particles having one or more desired properties, for example, surface functionality, surface charge, size, zeta (ζ) potential, hydrophobicity, ability to control immunogenicity, and the like. One or more of the macromolecules within the particles may include one or more polymers chosen to be biocompatible or biodegradable, one or more polymers chosen to reduce immunogenicity, and/or one or more moieties, for instance, a targeting moiety, an imaging moiety, a chelating moiety, a moiety having multiple charge groups, a neutral moiety, or a therapeutic moiety. These are discussed in detail below. The macromolecules within the library may comprise some or all of these polymers, in any suitable combination (including, but not limited to, combinations in which a first polymer comprises all of these species and a second polymer does not contain any of these species).

As a specific example, in one embodiment, the particles may include a first macromolecule comprising a biocompatible polymer, and a moiety selected from the group consisting of a targeting moiety, an imaging moiety, a chelating moiety, a moiety having multiple charge groups, and a therapeutic moiety, and a second macromolecule comprising a biocompatible polymer, which may or may not be the same as that of the first macromolecule. As another example, a first macromolecule may be a block copolymer comprising a biocompatible hydrophobic polymer, a biocompatible hydrophilic polymer, and a moiety selected from the group consisting of a targeting moiety, an imaging moiety, a chelating moiety, a moiety having multiple charge groups, a neutral moiety, and a therapeutic moiety; and a second macromolecule distinguishable from the first macromolecule in some fashion. For instance, the second macromolecule may comprise the same (or a different) biocompatible hydrophobic polymer and the same (or a different) biocompatible hydrophilic polymer, but a different moiety (or no moiety at all) than the first macromolecule. As another example, the first macromolecule may comprise a biocompatible hydrophilic polymer and a moiety selected from the group consisting of a targeting moiety, an imaging moiety, a chelating moiety, a moiety having multiple charge groups, a neutral moiety, and a therapeutic moiety, and a second macromolecule distinguishable from the first macromolecule in some fashion; or the first macromolecule may comprise a biocompatible hydrophobic polymer and a moiety selected from the group consisting of a targeting moiety, an imaging moiety, a chelating moiety, a moiety having multiple charge groups, a neutral moiety, and a therapeutic moiety, and a second macromolecule distinguishable from the first macromolecule in some fashion.

The first macromolecule may also contain, as another example, a first polymer comprising a biocompatible hydrophobic polymer, a biocompatible hydrophilic polymer, and a moiety selected from the group consisting of a targeting moiety, an imaging moiety, a chelating moiety, a moiety having multiple charge groups, a neutral moiety, and a therapeutic moiety, and a second macromolecule that is distinguishable from the first macromolecule. For instance, the second macromolecule may contain none of the polymers of the first macromolecule, the second macromolecule may contain one or more polymers of the first macromolecule and one or more polymers not present in the first macromolecule, the second macromolecule may lack one or more of the polymers of the first macromolecule, the second macromolecule may contain all of the polymers of the first macromolecule, but in a different order and/or with one or more of the polymers having different molecular weights, etc.

As yet another example, the first macromolecule may comprising a biocompatible hydrophobic polymer, a biocompatible hydrophilic polymer, and a moiety selected from the group consisting of a targeting moiety, an imaging moiety, a chelating moiety, a moiety having multiple charge groups, a neutral moiety, and a therapeutic moiety, and the second macromolecule may comprise the biocompatible hydrophobic polymer and the biocompatible hydrophilic polymer, and be distinguishable from the first macromolecule in some fashion. As still another example, the first macromolecule may comprise a biocompatible hydrophobic polymer and a biocompatible hydrophilic polymer, and the second macromolecule may comprise the biocompatible hydrophobic polymer and a moiety selected from the group consisting of a targeting moiety, an imaging moiety, a chelating moiety, a moiety having multiple charge groups, a neutral moiety, and a therapeutic moiety, where the second macromolecule is distinguishable from the first macromolecule in some fashion.

Figure 2B:
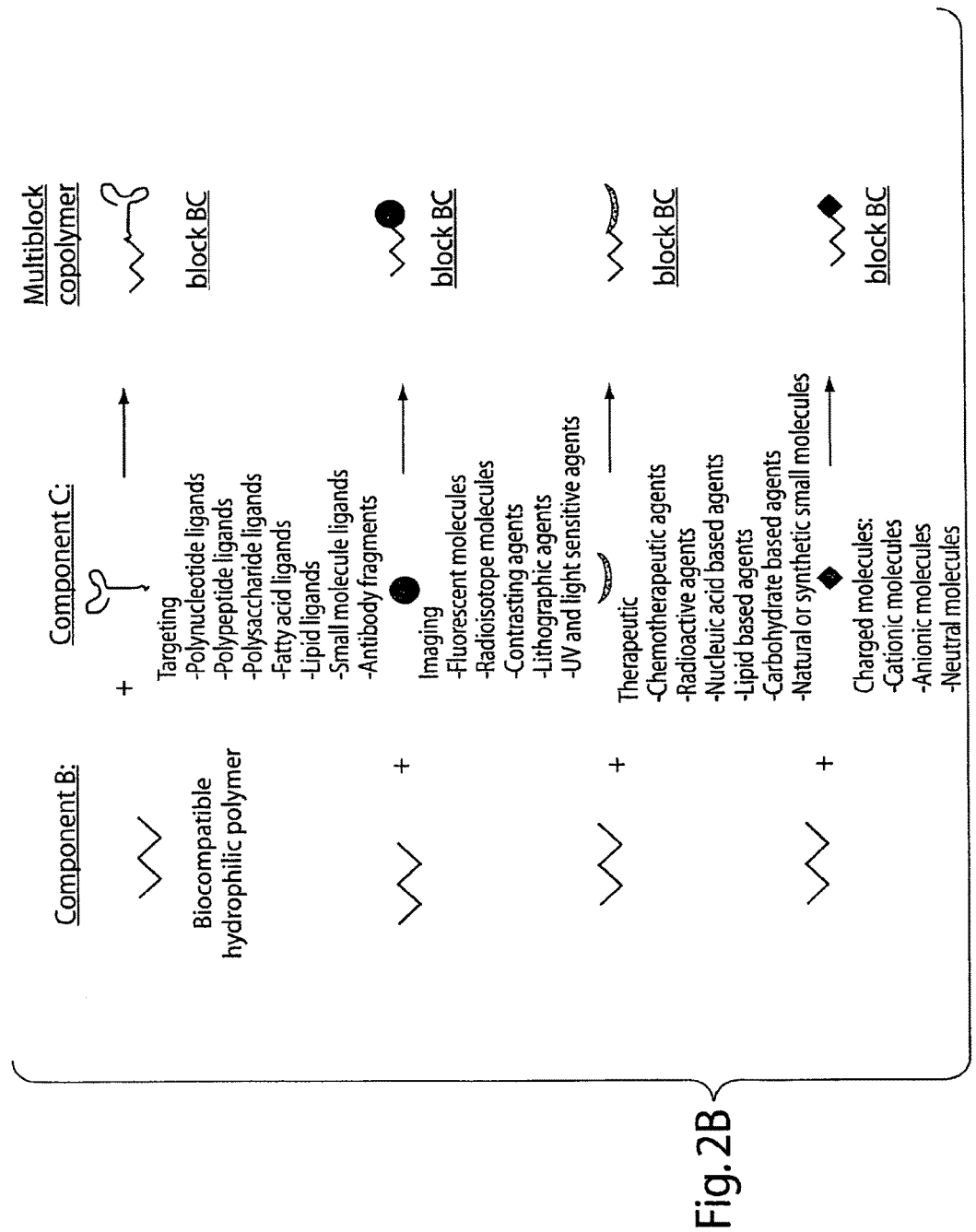
Figure 2C:
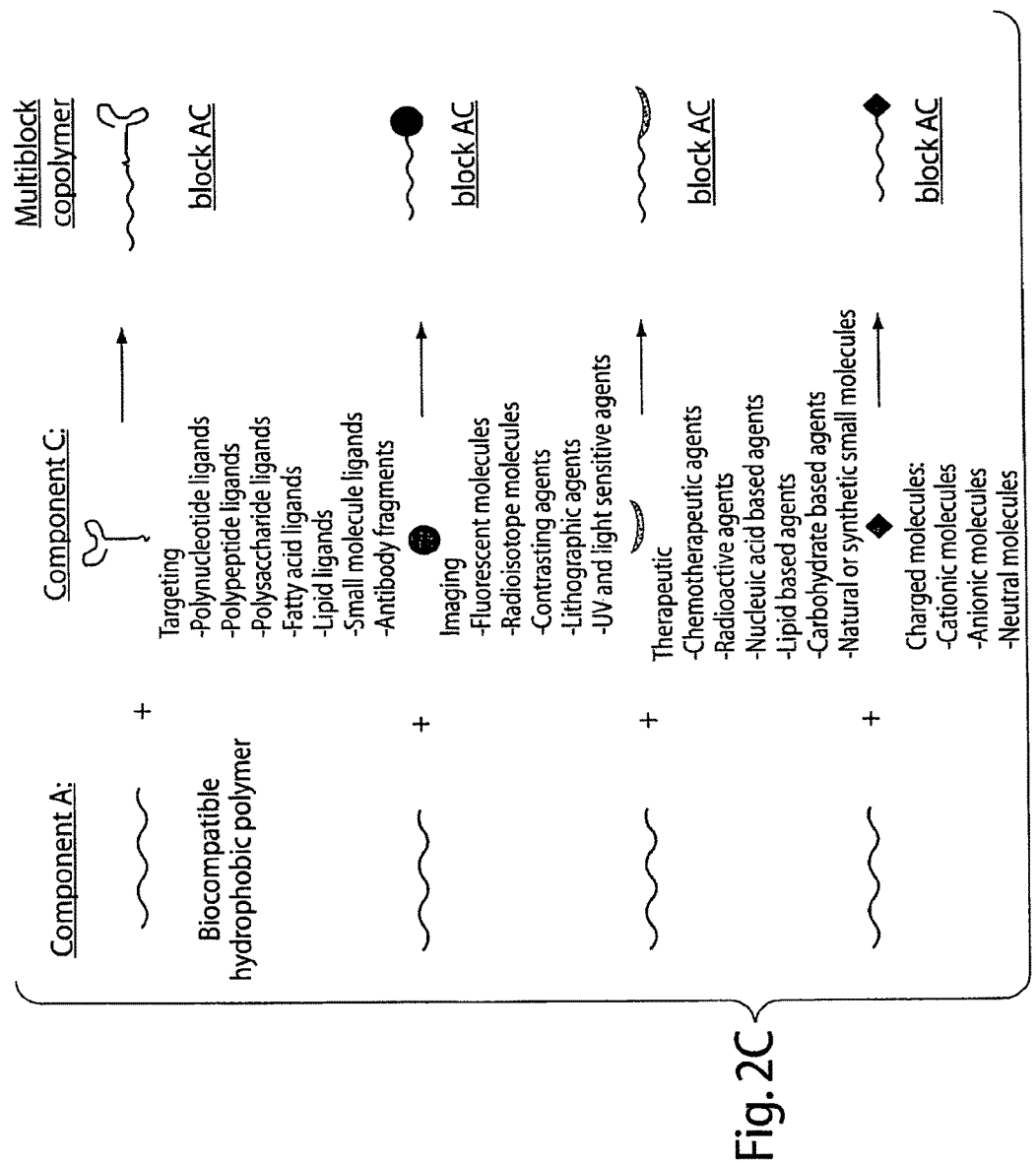

Referring now to FIGS. 2-4, non-limiting examples of various libraries of the present invention are shown. In FIGS. 2A-2C, examples of the synthesis of various macromolecules useful in libraries of the present invention are shown. In FIG. 2A, a block copolymer comprising three components is illustrated: a biocompatible hydrophobic polymer, a biocompatible hydrophilic polymer, and a moiety, which may be a targeting moiety, an imaging moiety, a therapeutic moiety, a moiety having multiple charge groups, a neutral moiety, or the like. Examples of targeting moieties include, but are not limited to, a polynucleotide, a polypeptide, a polysaccharide, a fatty acid, a lipid, a small molecule, or an antibody. Examples of imaging moieties include, but are not limited to, a fluorescent molecule, a radioactive molecule (e.g., comprising a radioisotope), a contrast agent, a lithographic agent, an agent sensitive to ultraviolet light, or an agent sensitive to visible light. Examples of therapeutic agents include, but are not limited to, a chemotherapeutic agent, a radioactive agent, a nucleic acid-based agent, a lipid-based agent, a carbohydrate based agent, a natural small molecule, or a synthetic small molecule. Examples of charged molecules include cationic molecules, or anionic molecules. In some cases, the moiety may be an uncharged (i.e., neutral) or zwitterionic. In one embodiment, the moiety is a moiety having multiple charge groups, for example, a zwitterionic molecule, a molecule having multiply charged portions, etc. In another embodiment, the moiety is divalent or a polyvalent.

It should be noted that the macromolecules need not include each of the components described above. For instance, as is illustrated in FIG. 2B, a polymer useful in a library of the present invention may include a hydrophilic biocompatible polymer and a moiety, which may be a targeting moiety, an imaging moiety, a therapeutic moiety, a moiety having multiple charge groups, or a neutral moiety, i.e., the polymer need not include a biocompatible hydrophobic polymer. Similarly, as is illustrated in FIG. 2C, a polymer useful in a library of the present invention may include a hydrophobic biocompatible polymer and a moiety, which may be a targeting moiety, an imaging moiety, a therapeutic moiety, a moiety having multiple charge groups, or a neutral moiety, i.e., the polymer need not include a biocompatible hydrophilic polymer.

Figure 3A:
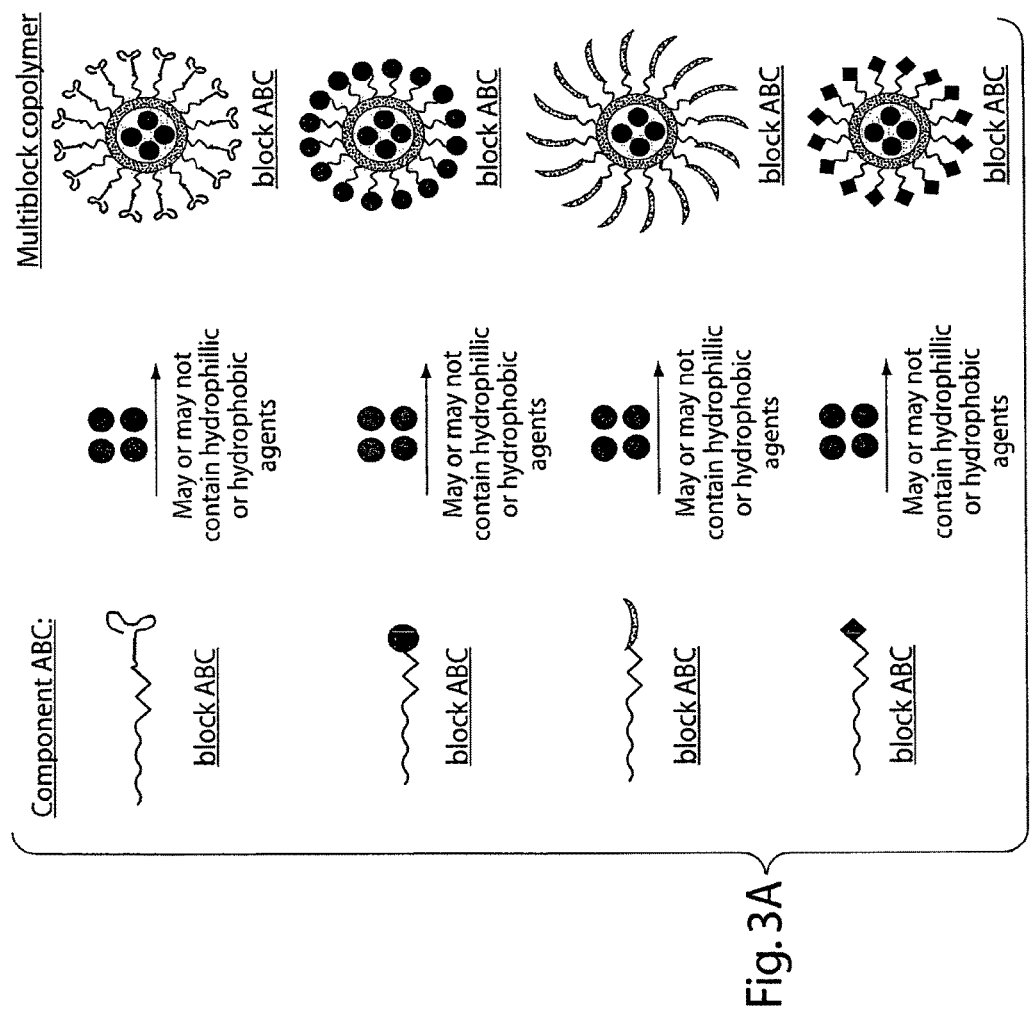
FIGS. 3A-3D illustrate schematic diagrams of various polymeric particles of certain embodiments of the present invention.

The polymers or macromolecules may then be formed into a particle, using techniques such as those discussed in detail below. The geometry formed by the particle from the polymer or macromolecule may depend on factors such as the polymers that form the particle. In addition, also as discussed below, in some cases, the particle may include a hydrophilic agent or a hydrophobic agent, depending on the structure of the particle. For example, the particle may contain a drug or other therapeutic agent. The hydrophilic or hydrophobic agent may be incorporated in the particle during formation of the particle, e.g., by including the agent in a solution containing the polymers that are used to form the particle, and/or the agent may be incorporated in the particle after its formation. Examples of such particles are shown in FIG. 3A for various moieties such as a targeting moiety, an imaging moiety, a therapeutic moiety, a moiety having multiple charge groups, or a neutral moiety.

Figure 3B:
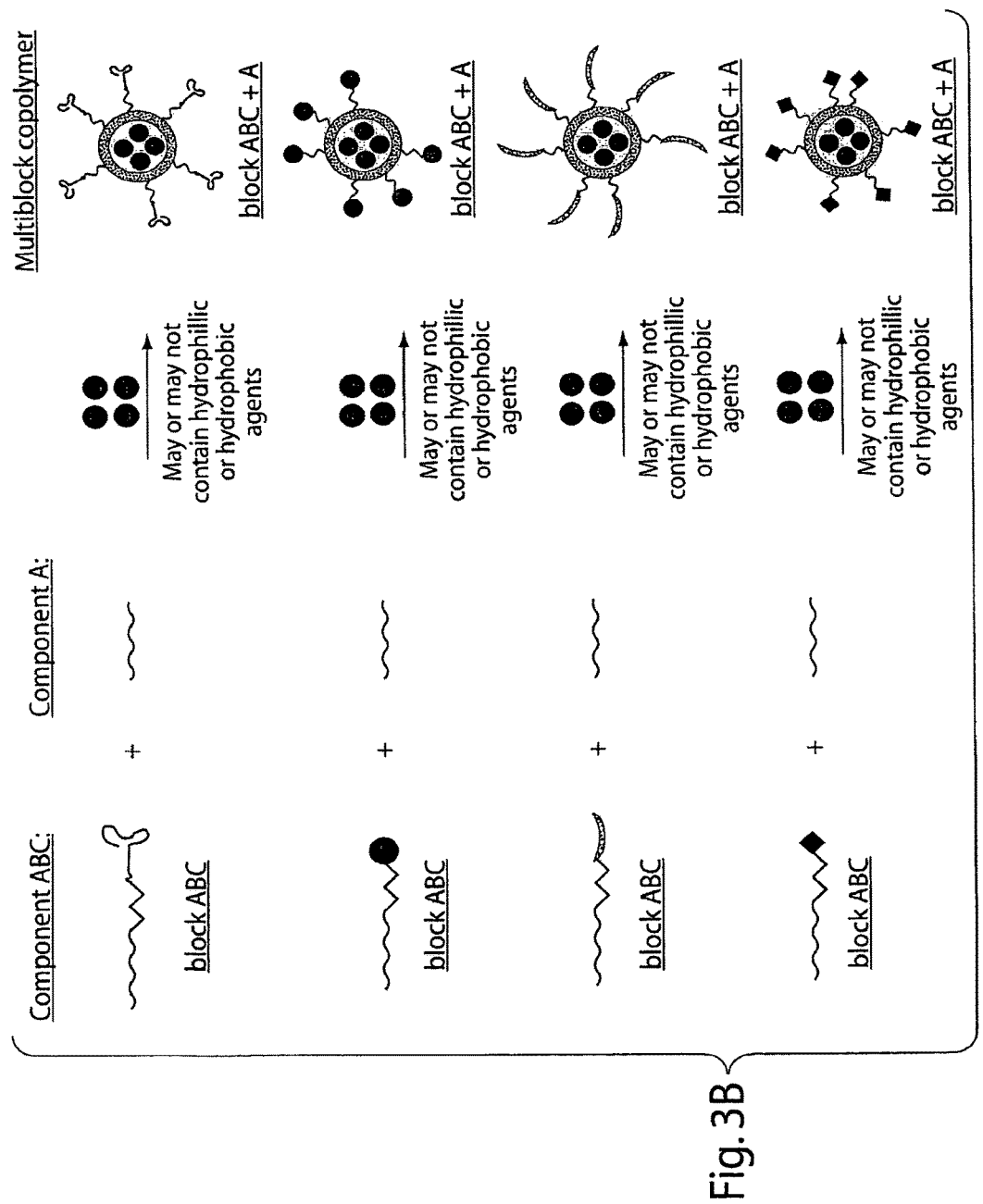
Figure 3C:
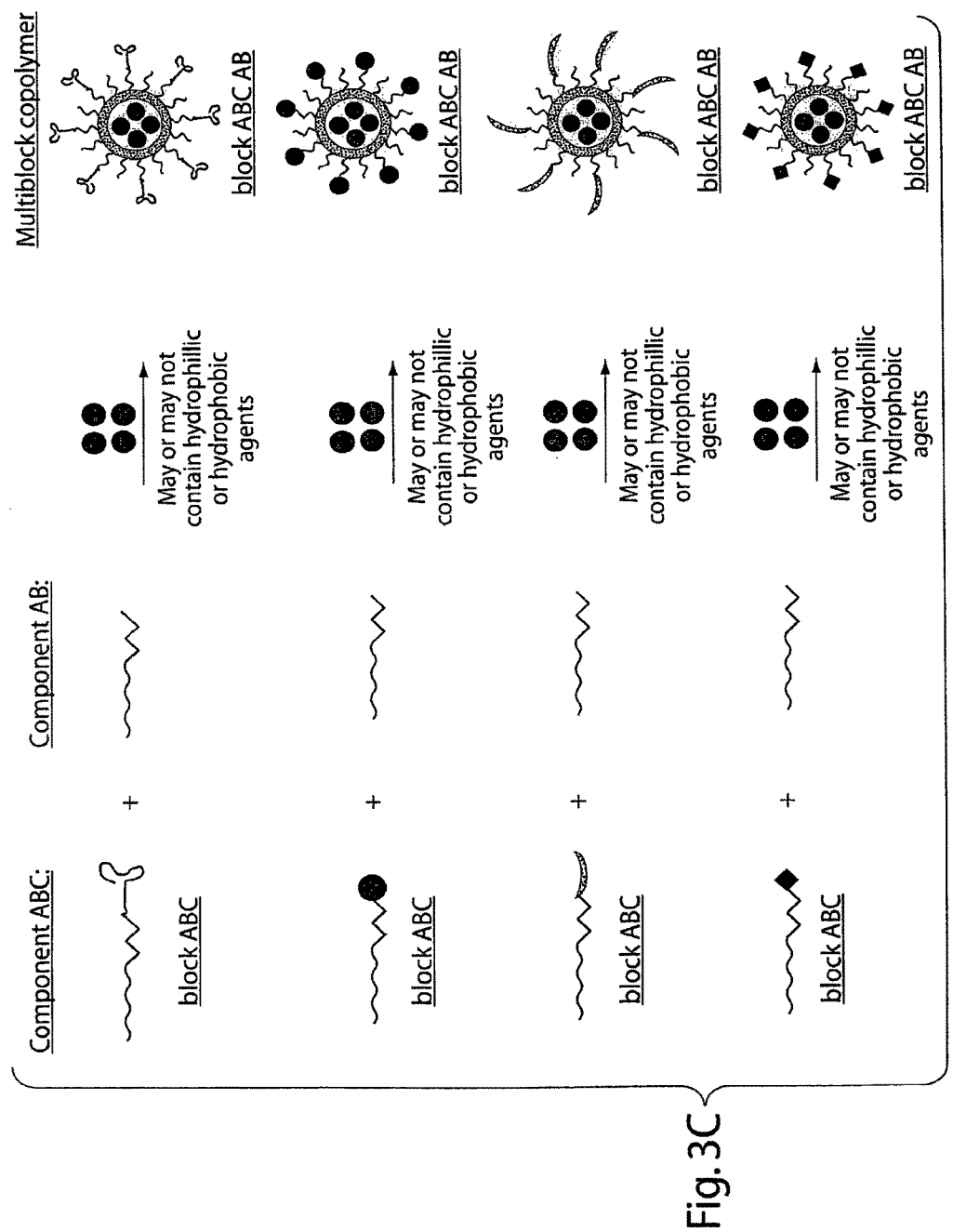
Figure 3D:
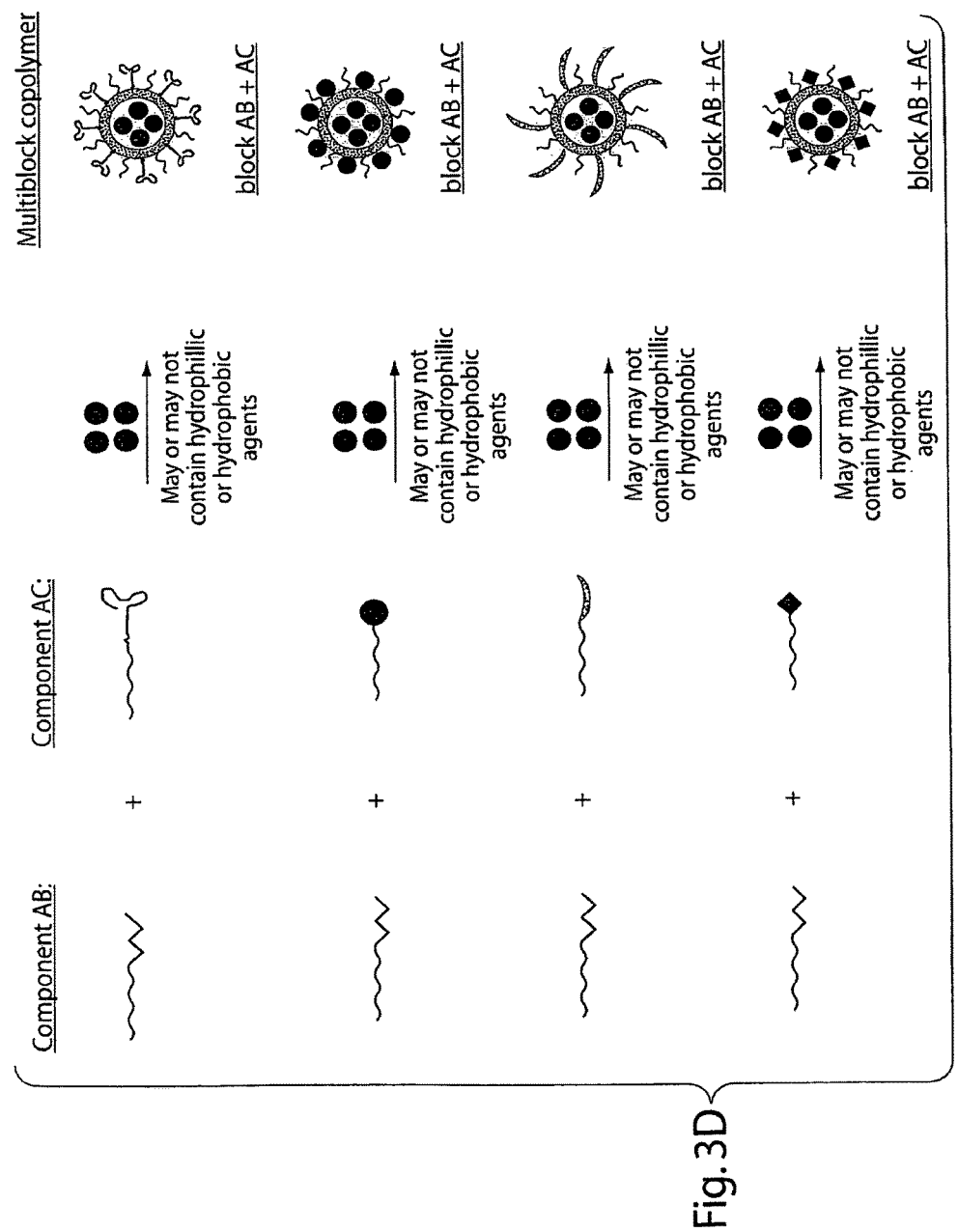

In addition, the particle may contain additional polymers or macromolecules, which may be distinguishable from the polymers or macromolecules discussed above. Non-limiting examples are shown in FIGS. 3B-3D. In FIG. 3B, a first macromolecule comprising a biocompatible hydrophobic polymer, a biocompatible hydrophilic polymer, and a moiety, which may be a targeting moiety, an imaging moiety, a therapeutic moiety, a moiety having multiple charge groups, or a neutral moiety, is combined with a second macromolecule comprising a biocompatible hydrophobic polymer, to form a particle of the preset invention. The biocompatible hydrophobic polymer of the second macromolecule may or may not be the same as the biocompatible hydrophobic polymer of the first macromolecule (e.g., the second biocompatible hydrophobic polymer may have a different molecular structure, or the same molecular structure but the same or a different molecular weight, as the first biocompatible hydrophobic polymer). As previously discussed, the first and second macromolecules may be combined together at different ratios to produce particles comprising the first and second macromolecules.

Similarly, as is depicted in FIG. 3C, a particle of the invention may comprise a first macromolecule comprising a biocompatible hydrophobic polymer, a biocompatible hydrophilic polymer, and a moiety, which may be a targeting moiety, an imaging moiety, a therapeutic moiety, a moiety having multiple charge groups, or a neutral moiety, and a second macromolecule that comprises a biocompatible hydrophobic polymer and a biocompatible hydrophilic polymer, but does not contain the moiety of the first macromolecule (i.e., the second macromolecule may comprise a different moiety, or no moiety at all, as is shown in FIG. 3C). Similar to the above, the first and second macromolecules may be combined together at different ratios to produce particles comprising the first and second macromolecules. In FIG. 3D, as another embodiment, a first macromolecule comprising a biocompatible hydrophobic polymer and a biocompatible hydrophilic polymer, is combined with a second macromolecule comprising a biocompatible hydrophobic polymer and a moiety, which may be a targeting moiety, an imaging moiety, a therapeutic moiety, a moiety having multiple charge groups, or a neutral moiety. The biocompatible hydrophobic polymer of the first macromolecule may or may not be the same as the biocompatible hydrophobic polymer of the second macromolecule. For instance, the two hydrophobic polymers may have different molecular structures, or the same molecular structures but the same or different molecular weights.

Figure 4A:
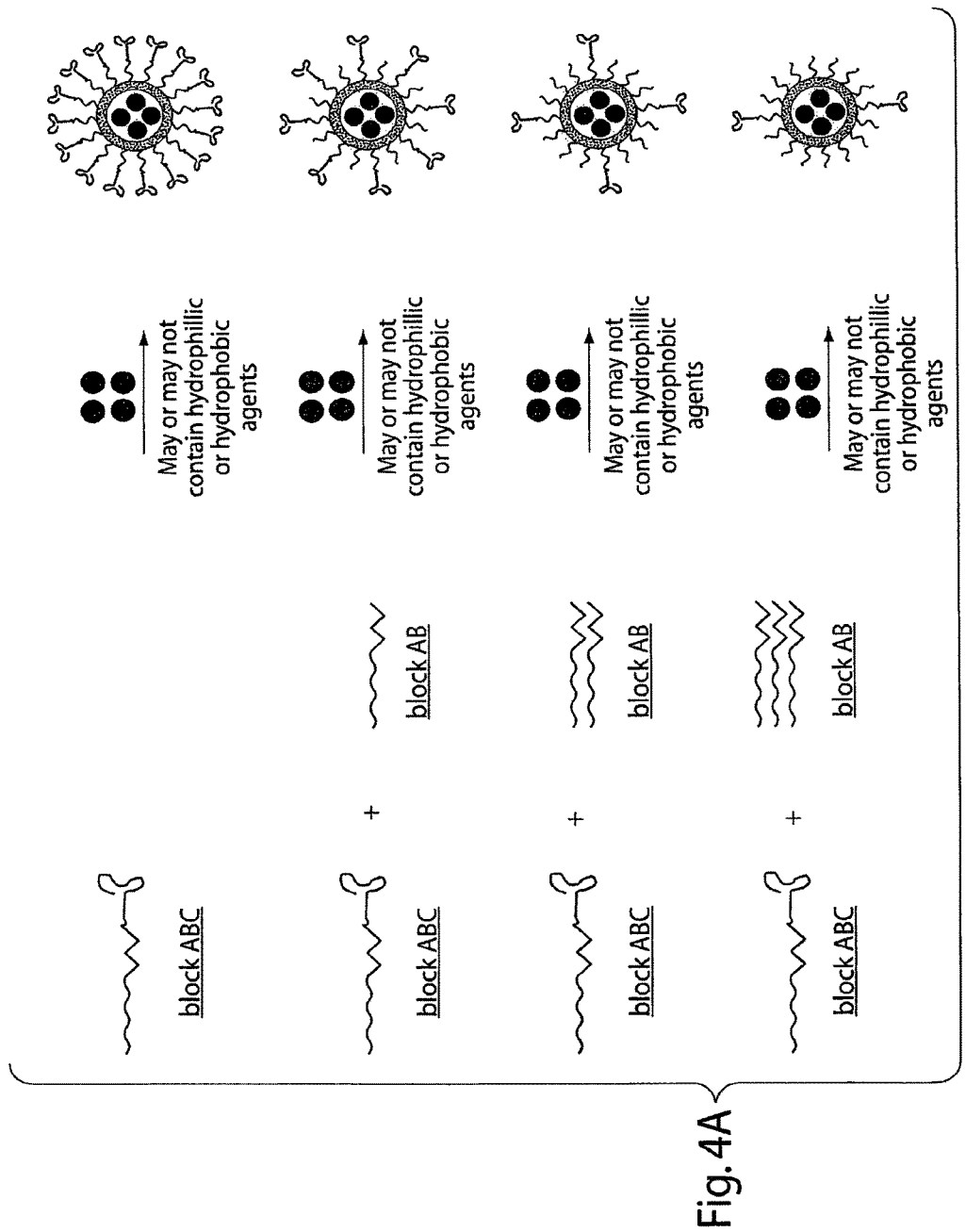
FIGS. 4A-4C illustrate schematic diagrams of various polymeric particles comprising two or more polymers, according to another embodiment of the invention.

FIG. 4 illustrates that libraries can be produced using polymers such as those described above. For example, in FIG. 4A, polymeric particles comprising a first macromolecule comprising a biocompatible hydrophobic polymer, a biocompatible hydrophilic polymer, and a moiety, which may be a targeting moiety, an imaging moiety, a therapeutic moiety, a moiety having multiple charge groups, or a neutral moiety, and a second macromolecule that comprises a biocompatible hydrophobic polymer and a biocompatible hydrophilic polymer (e.g., as discussed in FIG. 3C) may be used to create a library of particles having different ratios of the first and second macromolecules. Such a library may be useful in achieving particles having any number of desirable properties, for instance properties such as surface functionality, surface charge, size, zeta ($\zeta$) potential, hydrophobicity, ability to control immunogenicity, or the like.

In FIG. 4A, different ratios of the first and second macromolecules (including ratios where one of the macromolecules is absent) are combined to produce particles that form the basis of the library. For instance, as shown in FIG. 4A, as the amount of the first macromolecule is increased, relative to the second macromolecule, the amount of moiety (e.g., a targeting moiety) present on the surface of the particle may be increased. Thus, any suitable concentration of moiety on the surface may be achieved simply by controlling the ratio of the first and second macromolecules in the particles. Accordingly, such a library of particles may be useful in selecting or identifying particles having a particular functionality.

Figure 4B:
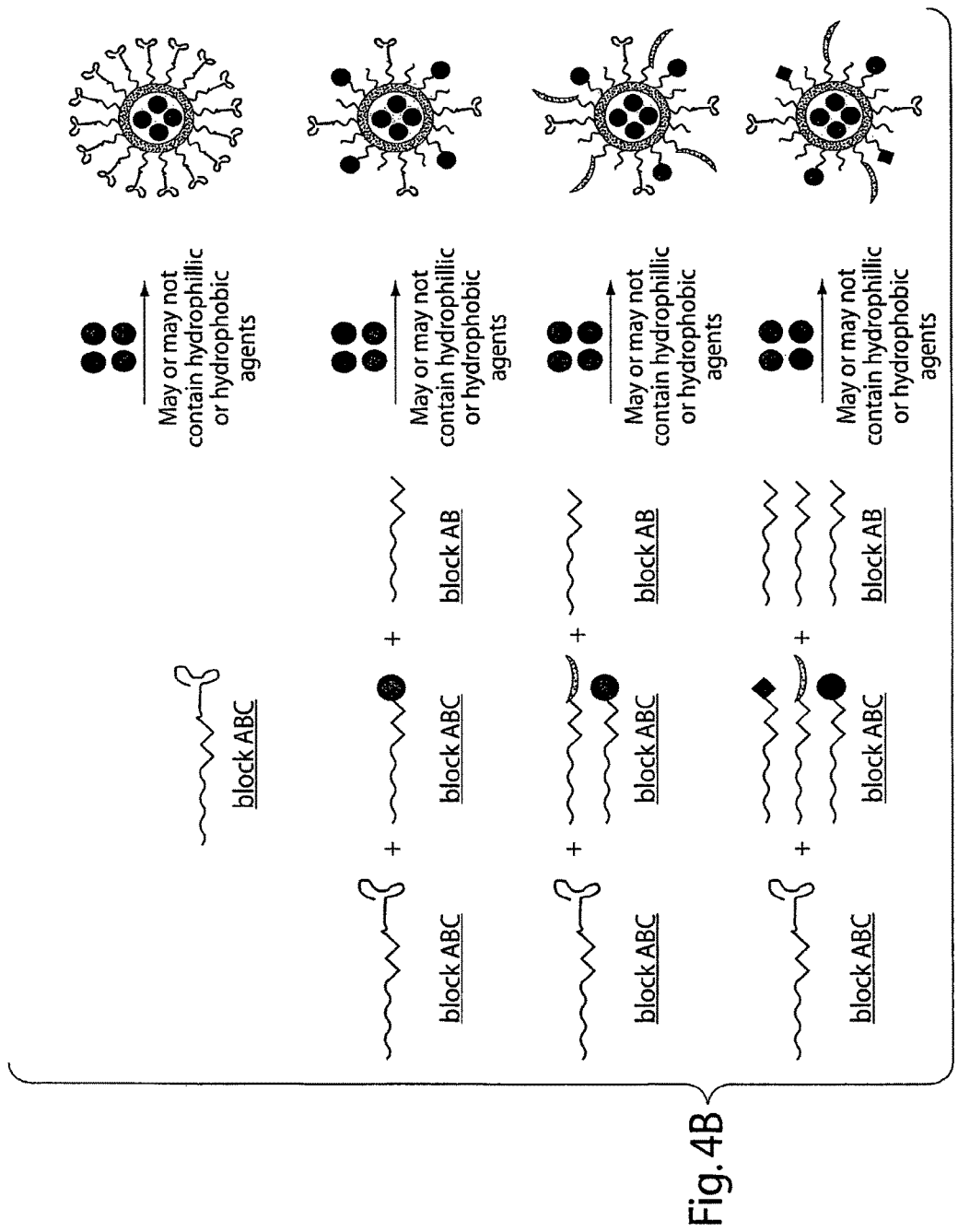
Figure 4C:
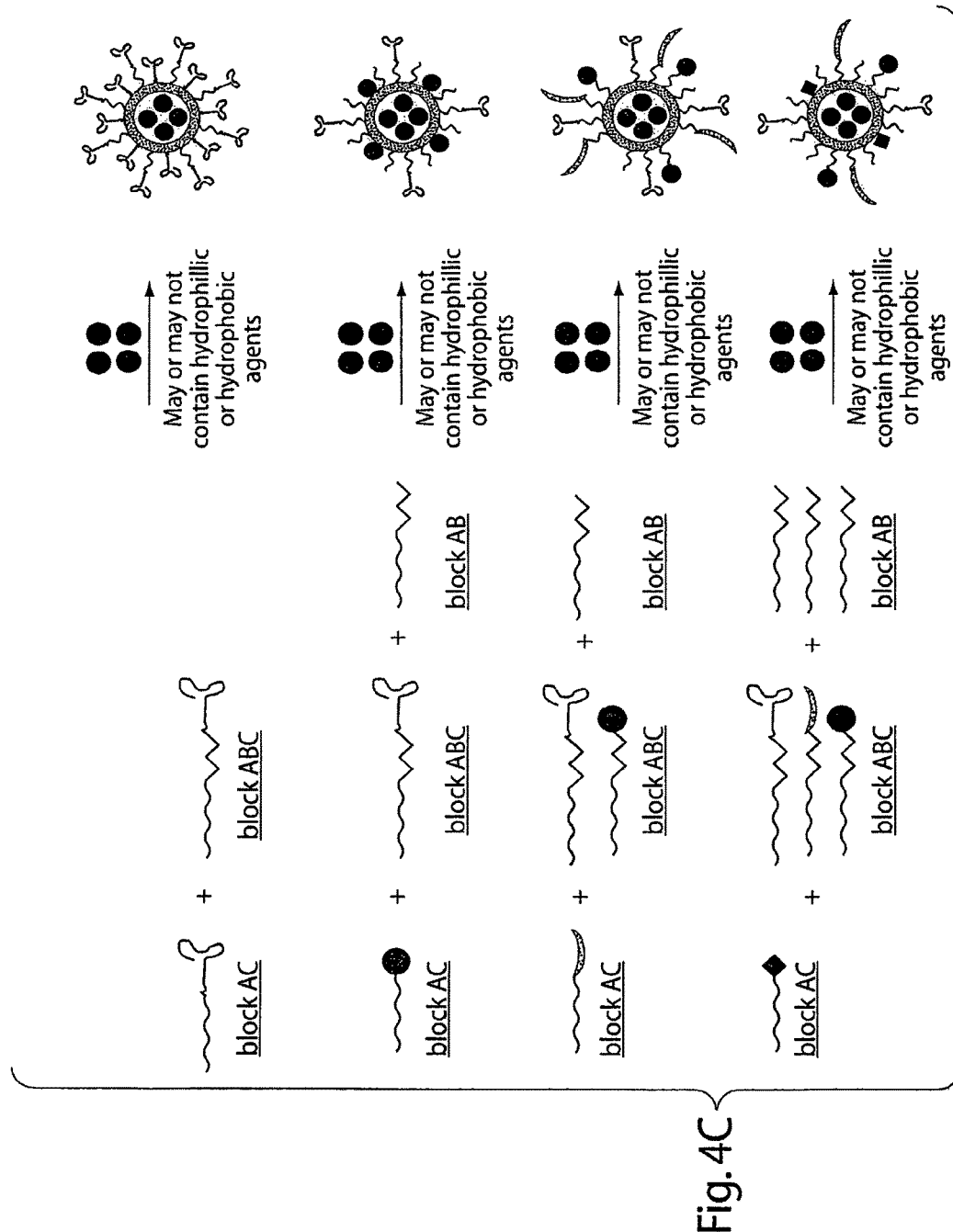

FIGS. 4B and 4C illustrates embodiments in which more than one type of macromolecule is used. For instance, in some cases, the particle may include more than one type of moiety, for instance, more than one type of therapeutic moiety, a therapeutic moiety and an imaging moiety, etc. Any of polymeric systems herein, such as those previously described with reference to FIGS. 2 and 3, may be used. Particles having such moieties present on the surface of the particle, and in any suitable concentration, may be created through the use of a library of such particles, created as described above. In addition, the overall concentration of moieties present on the surface may also be controlled, for instance, by the use of polymers that do not contain any moieties (i.e., "block AB" in FIGS. 4A and 4B). Thus, a wide range of moieties may be presented on the surface of the particles at any suitable concentration, and each concentration may be independently controlled. In addition, more than two polymers or macromolecules may be used in certain embodiments of the invention. For example, the library may have three, four, or more polymers or macromolecules, in which the ratios of each are independently controlled.

Figure 5:
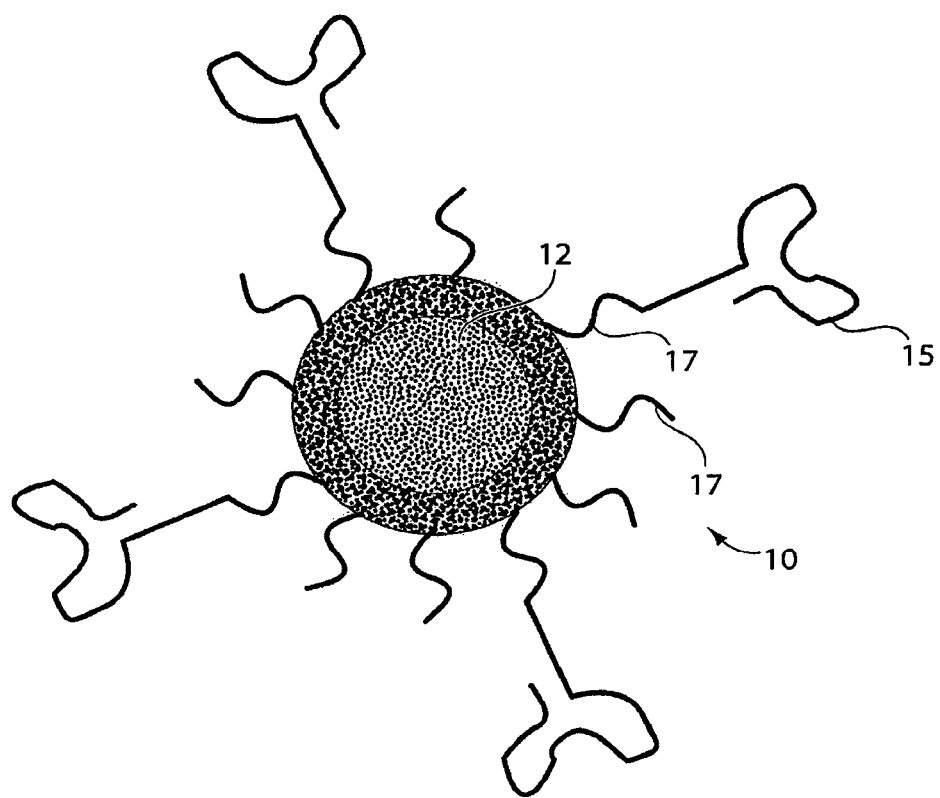
FIG. 5 is a schematic diagram a nanoparticle formed in accordance with another embodiment of the invention.

As specific examples, in some embodiments of the present invention, the library includes particles comprising polymeric conjugates of a biocompatible polymer and a moiety selected from a targeting moiety, an imaging moiety, a chelating moiety, a moiety having multiple charge groups, a neutral moiety, or a therapeutic moiety, as discussed herein. Referring now to FIG. 5, one such particle is shown as a non-limiting example. In this figure, a polymeric conjugate of the invention is used to form a particle 10. The polymer forming particle 10 includes a targeting moiety 15, present on the surface of the particle, and a biocompatible portion 17. In some cases, as shown here, targeting moiety 15 may be conjugated to biocompatible portion 17. However, not all of biocompatible portion 17 is shown conjugated to targeting moiety 15. For instance, in some cases, particles such as particle 10 may be formed using a first polymer comprising biocompatible portion 17 and targeting moiety 15, and a second polymer comprising biocompatible portion 17 but not targeting moiety 15. By controlling the ratio of the first and second polymers, particles having different properties may be formed, and in some cases, libraries of such particles may be formed. In addition, contained within the center of particle 10 is drug 12. In some cases, drug 12 may be contained within the particle due to hydrophobic effects. For instance, the interior of the particle may be relatively hydrophobic with respect to the surface of the particle, and the drug may be a hydrophobic drug that associates with the relatively hydrophobic center of the particle. As a specific example, particle 10 may contain polymers including a relatively hydrophobic biocompatible polymer and a relatively hydrophilic targeting moiety 15, such that, during particle formation, a greater concentration of the hydrophilic targeting moiety is exposed on the surface and a greater concentration of the hydrophobic biocompatible polymer is present within the interior of the particle.

Thus, various aspects of the invention are generally directed to polymeric conjugates comprising a biocompatible polymer, and a moiety such as a targeting moiety, an imaging moiety, a chelating moiety, a moiety having multiple charge groups, a neutral moiety, or a therapeutic moiety. In some cases, the polymeric conjugate is a block copolymer, and in some embodiments, the polymeric conjugate is amphiphilic, i.e., having a relatively hydrophilic portion and a relatively hydrophobic portion. The targeting moiety may be, for example, a peptide or a polynucleotide, such as an aptamer. In some cases, the targeting moiety is able to specifically bind to a biological substrate, for example, a cell surface receptor. The biocompatible portion of the polymer may be biodegradable and/or hydrolyzable, in some cases. In some embodiments, the biocompatible polymer is a hydrophobic polymer. Non-limiting examples of biocompatible polymers include polylactide, polyglycolide, and/or poly(lactide-co-glycolide).

In some cases, the polymeric conjugate is part of a controlled release system. A controlled release system, as used herein, is a polymer combined with an active agent or a drug or other payload, such as a therapeutic agent, a diagnostic agent, a prognostic, a prophylactic agent, etc., and the active agent is released from the controlled release system in a predesigned or controlled manner. For example, the active agent may be released in a constant manner over a predetermined period of time, the active agent may be released in a cyclic manner over a predetermined period of time, or an environmental condition or external event may trigger the release of the active agent. The controlled release polymer system may include a polymer that is biocompatible, and in some cases, the polymer is biodegradable.

A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer is biologically derived, i.e., a biopolymer. Non-limiting examples include peptides or proteins (i.e., polymers of various amino acids), or nucleic acids such as DNA or RNA, as discussed below. In some cases, additional moieties may also be present in the polymer, for example biological moieties such as those described below.

If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

It should be understood that, although the terms "first," "second," etc. may be used herein to describe various elements, including polymeric components, these terms should not be construed as being limiting (e.g., describing a particular order or number of elements), but rather, as being merely descriptive, i.e., labels that distinguish one element from another, as is commonly used within the field of patent law. Thus, for example, although one embodiment of the invention may be described as having a "first" element present and a "second" element present, other embodiments of the invention may have a "first" element present but no "second" element present, a "second" element present but no "first" element present, two (or more) "first" elements present, and/or two (or more) "second" elements present, etc., and/or additional elements such as a "first" element, a "second" element, and a "third" element, without departing from the scope of the present invention.

Various embodiments of the present invention are directed to polymeric conjugates. As used herein, a "polymeric conjugate" describes two or more polymers (such as those described herein) that have been associated with each other, usually by covalent bonding of the two or more polymers together. Thus, a polymeric conjugate may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to nonpolymeric moieties).

In some embodiments, the polymeric conjugate is amphiphilic, i.e., having a hydrophilic portion and a hydrophobic portion, or a relatively hydrophilic portion and a relatively hydrophobic portion. A hydrophilic polymer is one generally that attracts water and a hydrophobic polymer is one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymeric conjugate of the present invention includes a biocompatible polymer, i.e., the polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In certain embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.). Examples of biodegradable polymers include, but are not limited to, poly(lactide) (or polylactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In another set of embodiments, a polymeric conjugate of the present invention includes a polymer able to control immunogenicity, for example a poly(alkylene glycol) (also known as poly(alkylene oxide)), such as polypropylene glycol), or poly(ethylene oxide), also known as poly(ethylene glycol) ("PEG"), having the formula —(CH$_2$—CH$_2$—O)$_n$—, where n is any positive integer. The poly(ethylene glycol) units may be present within the polymeric conjugate in any suitable form. For instance, the polymeric conjugate may be a block copolymer where one of the blocks is poly(ethylene glycol). A polymeric conjugate containing poly(ethylene glycol) repeat units is also referred to as a "PEGylated" polymer. Such polymers can control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly(ethylene glycol) repeat units may increase plasma half-life of the polymeric conjugate, for instance, by decreasing the uptake of the polymeric conjugate by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, as discussed in the examples below, by ring opening polymerization techniques (ROMP), or the like.

In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(esterether).

In yet another set of embodiments a polymeric conjugate of the present invention includes a targeting moiety, i.e., a moiety able to bind to or otherwise associate with a biological entity, for example, a membrane component, a cell surface receptor, prostate specific membrane antigen, or the like. The term "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

Non-limiting examples of biological moieties include a peptide, a protein, an enzyme, a nucleic acid, a fatty acid, a hormone, an antibody, a carbohydrate, a peptidoglycan, a glycopeptide, or the like. These and other biological moieties are discussed in detail below. In some cases, the biological moiety may be relatively large, for example, for peptides, nucleic acids, or the like. For example, the biological moiety may have a molecular weight of at least about 1,000 Da, at least about 2,500 Da, at least about 3000 Da, at least about 4000 Da, or at least about 5,000 Da, etc. Relatively large targeting moieties may be useful, in some cases, for differentiating between cells. For instance, in some cases, smaller targeting moieties (e.g., less than about 1000 Da) may not have adequate specificity for certain targeting applications, such as targeting applications. In contrast, larger molecular weight targeting moieties can offer a much higher targeting affinity and/or specificity. For example, a targeting moiety may offer smaller dissociation constants, e.g., tighter binding. However, in other embodiments, the targeting moiety may be relatively small, for example, having a molecular weight of less than about 1,000 Da or less than about 500 Da.

In one embodiment, the targeting moiety includes a protein or a peptide. "Proteins" and "peptides" are well-known terms in the art, and are not precisely defined in the art in terms of the number of amino acids that each includes. As used herein, these terms are given their ordinary meaning in the art. Generally, peptides are amino acid sequences of less than about 100 amino acids in length, but can include sequences of up to 300 amino acids. Proteins generally are considered to be molecules of at least 100 amino acids. A protein may be, for example, a protein drug, an antibody, an antibody fragment, a recombinant antibody, a recombinant protein, an enzyme, or the like. In some cases, one or more of the amino acids of the protein or peptide may be modified in some instances, for example, by the addition of a chemical entity such as a carbohydrate group, a phosphate group, a farnesyl group, an isofarnesyl group, a fatty acid group, a linker for conjugation, functionalization, or other modification, etc.

Other examples of peptides or proteins include, but are not limited to, ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor alpha, transforming growth factor beta, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocyte function-associated antigen, intercellular adhesion molecule, vascular cell adhesion molecule, Thy-1, antiporters, CA-15-3 antigen, fibronectins, laminin, myelin-associated glycoprotein, GAP, GAP-43.

As used herein, an "antibody" refers to a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well characterized fragments produced by digestion with various peptidases.

Non-limiting examples of antibodies and other suitable targeting moieties include anti-cluster of differentiation antigen CD-1 through CD-166 and the ligands or counter receptors for these molecules; anti-cytokine antibodies, e.g., anti-IL-1 through anti-IL-18 and the receptors for these molecules; anti-immune receptor antibodies, antibodies against T cell receptors, major histocompatibility complexes I and II, B cell receptors, selectin killer inhibitory receptors, killer activating receptors, OX-40, MadCAM-1, GlyCAM1, integrins, cadherens, sialoadherens, Fas, CTLA-4, Fc-gamma receptor, Fc-alpha receptors, Fc-epsilon receptors, Fc-mu receptors, and their ligands; anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitrous oxide, thromboxanes; or anti-adhesion molecules, e.g., carcioembryonic antigens, lamins, or fibronectins.

Other examples of targeting moieties include cytokines or cytokine receptors, such as Interleukin-1 (IL-1), IL-2, IL-3, IL-4, IL-5, IL-6, IL-7, IL-8, IL-9, IL-10, IL11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor beta, tumor necrosis factor, lymphotoxin, Fas, granulocyte colony stimulating factor, granulocyte macrophage colony stimulating factor, interferon alpha, interferon beta, interferon gamma.

Still other examples of targeting moieties include growth factors and protein hormones, for example, erythropoietin, angiogenin, hepatocyte growth factor, fibroblast growth factor, keratinocyte growth factor, nerve growth factor, tumor growth factor alpha, thrombopoietin, thyroid stimulating factor, thyroid releasing hormone, neurotrophin, epidermal growth factor, VEGF, ciliary neurotrophic factor, LDL, somatomedin, insulin growth factor, or insulin-like growth factor I and II.

Additional examples of targeting moieties include chemokines, for example, ENA-78, ELC, GRO-alpha, GRO-beta, GRO-gamma, HRG, LIF, IP-10, MCP-1, MCP-2, MCP-3, MCP-4, MIP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors such as CXCR1, CXCR2, CXCR3, CXCR4, CXCR5, CXCR6, CXCR7, or beta-chemokine receptors such as CCR1, CCR2, CCR3, CCR4, CCR5, CCR6, or CCR7.

In another embodiment, the targeting moiety includes a nucleic acid. The term "nucleic acids," or "oligonucleotides," as used herein, refers to a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "0," cytidine or "C," or uridine or "U"). In some cases, the polymer may also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitropyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynyl-cytidine, 5-propynyluridine, 5-bromouridine, 5-fluorouridine, 5-methylcytidine, 7-deazaadenosine, 7-deazaguanos-ine, 8-oxoadenosine, 8-oxoguanosine, O(6)-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. Other suitable base and/or polymer modifications are well-known to those of skill in the art. In some cases, the polynucleotide may include DNA, RNA, modified DNA, modified RNA, antisense oligonucleotides, expression plasmid systems, nucleotides, modified nucleotides, nucleosides, modified nucleosides, aptamers, intact genes, or combinations thereof. Other examples of polynucleotides include interfering RNA, natural or unnatural siRNAs, shRNAs, microRNAs, ribozymes, DNA plasmids, aptamers, antisense oligonucleotides, randomized oligonucleotides, or ribozymes.

Figure 6:
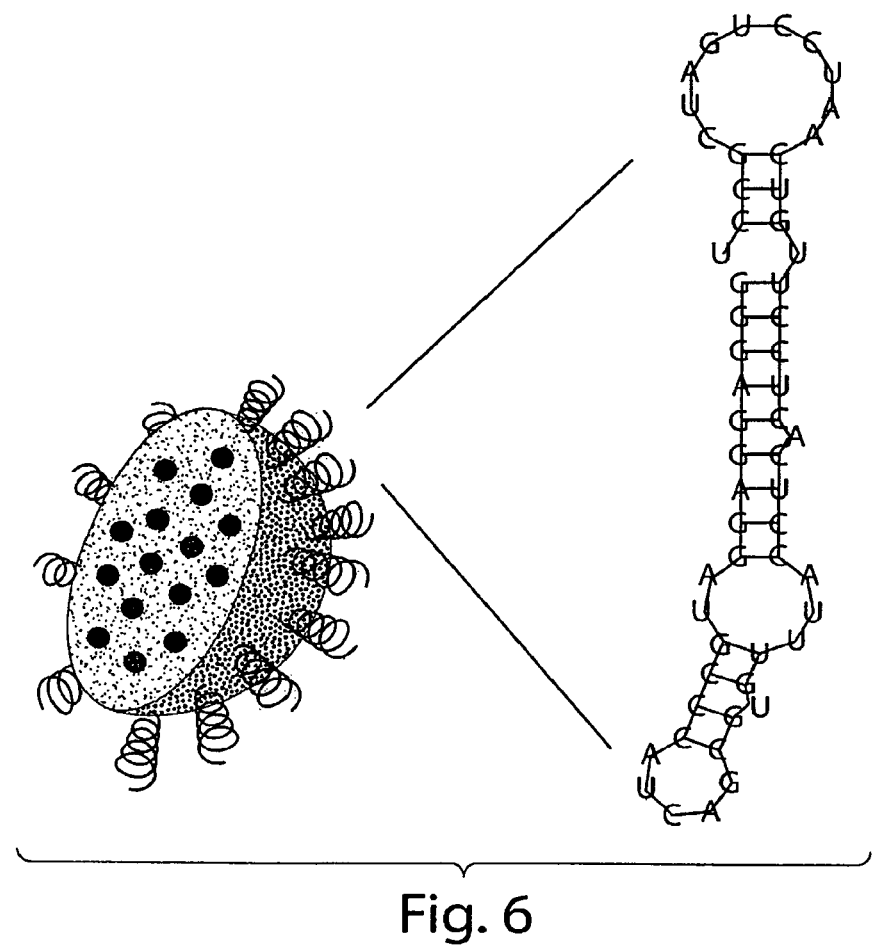
FIG. 6 is a schematic diagram illustrating a nanoparticle having aptamers, in yet another embodiment of the invention.

As a specific non-limiting example, the targeting moiety may include an aptamer, i.e. a nucleic acid able to specifically bind a specific target molecule, such as a biological moiety. Non-limiting examples of aptamers include RNA aptamers and DNA aptamers. For example, the size of the aptamer may be at least about 5 kDa, at least about 10 kDa, at least about 15 kDa, or at least about 20 kDa. A non-limiting example of a particular aptamer is prostate specific membrane antigen (PSMA) aptamer (FIG. 6). The PSMA aptamer may have the sequence

```
                                            (SEQ ID NO: 1)
GGGAGGACGAUGCGGAUCAGCCAUGUUUACGUCACUCCUUGUCAAUCCUC
AUCGGC.
```

In still another set of embodiments a polymeric conjugate of the present invention includes an imaging moiety or a sensing moiety, i.e., a moiety that can be determined in some fashion, either directly or indirectly. For instance, the imaging entity may be fluorescent, radioactive, electron-dense, a member of a binding pair, a substrate for an enzymatic reaction, an antigen for an antibody, etc. In some cases, the imaging entity itself is not directly determined, but instead interacts with a second entity in order to effect determination; for example, coupling of the second entity to the imaging entity may result in a determinable signal. Non-limiting examples of imaging moieties includes fluorescent compounds such as FITC or a FITC derivative, fluorescein, GFP, etc; a radioactive atom, for example, $^{3}H$, $^{14}C$, $^{33}P$, $^{32}P$, $^{125}I$, $^{131}I$, $^{35}S$, etc.; or a heavy metal species, for example, gold or osmium. As a specific example, an imaging moiety may be a gold nanoparticle.

In still another set of embodiments, a polymer conjugate of the present invention includes a therapeutic moiety, i.e., a moiety that has a therapeutic or prophylactic effect when given to a subject. Examples of therapeutic moieties include, but are not limited to, antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In yet another set of embodiments a polymeric conjugate of the present invention includes a chelating moiety, i.e., a moiety that can bind one or more ions, typically divalent (or higher) ions such as $Ca^{2+}$, $Mg^{2+}$, or $Fe^{2+}$. An example of such a moiety is ethylenediamine tetraacetic acid. In another set of embodiments a polymeric conjugate of the present invention includes a moiety having multiple charge groups, e.g., under physiological conditions.

A polymeric conjugate of the present invention may be formed using any suitable conjugation technique. For instance, two polymers such as a targeting moiety and a biocompatible polymer, a biocompatible polymer and a polyethylene glycol), etc., may be conjugated together using techniques such as EDC NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of such polymers, for instance, the conjugation of a poly(ester) and a poly(ether) to form a poly(ester-ether), can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety) comprising an amine. For instance, a targeting moiety, such as an aptamer, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated macromers may be washed away after such reactions, and the polymer may be precipitated in solvents such as, for instance, ethyl ether, hexane, methanol, or ethanol.

As a specific example, a nuclease-stable oligonucleotide, for instance, prostate specific membrane antigen (PSMA) aptamer, may be prepared as a targeting moiety in a particle as follows. Carboxylic acid modified poly(lactide-co-glycolide) (PLGA-COOH) may be conjugated to an amine-modified heterobifunctional poly(ethylene glycol) ($NH_2$—PEG-COOH) to form a copolymer of PLGA-PEG-COOH. By using an amine-modified PSMA aptamer ($NH_2$-Apt), a triblock polymer of PLGA-PEG-Apt may be formed by conjugating the carboxylic acid end of the PEG to the amine functional group on the aptamer. The multiblock polymer can then be used, for instance, as discussed below, e.g., for therapeutic, imaging, and/or diagnostic applications.

Another aspect of the invention is directed to particles that include polymer conjugates such as the ones described above. The particles may have a substantially spherical (i.e., the particles generally appear to be spherical), or non-spherical configuration. For instance, the particles, upon swelling or shrinkage, may adopt a non-spherical configuration. In some cases, the particles may include polymeric blends. For instance, a polymer blend may be formed that includes a first polymer comprising a targeting moiety and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree. Thus, in certain embodiments, a library of such particles may be created, as discussed below.

In some cases, the particle is a nanoparticle, i.e., the particle has a characteristic dimension of less than about 1 micrometer, where the characteristic dimension of a particle is the diameter of a perfect sphere having the same volume as the particle. For example, the particle may have a characteristic dimension of the particle may be less than about 300 nm, less than about 200 nm, less than about 150 nm, less than about 100 nm, less than about 50 nm, less than about 30 nm, less than about 10 nm, less than about 3 nm, or less than about 1 nm in some cases.

In some cases, a population of particles may be present. For example, a population of particles may include at least 20 particles, at least 50 particles, at least 100 particles, at least 300 particles, at least 1,000 particles, at least 3,000 particles, or at least 10,000 particles. Various embodiments of the present invention are directed to such populations of particles. For instance, in some embodiments, the particles may each be substantially the same shape and/or size ("monodisperse"). For example, the particles may have a distribution of characteristic dimensions such that no more than about 5% or about 10% of the particles have a characteristic dimension greater than about 10% greater than the average characteristic dimension of the particles, and in some cases, such that no more than about 8%, about 5%, about 3%, about 1%, about 0.3%, about 0.1%, about 0.03%, or about 0.01% have a characteristic dimension greater than about 10% greater than the average characteristic dimension of the particles. In some cases, no more than about 5% of the particles have a characteristic dimension greater than about 5%, about 3%, about 1%, about 0.3%, about 0.1%, about 0.03%, or about 0.01% greater than the average characteristic dimension of the particles.

In one set of embodiments, the particles may have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (e.g., an aptamer) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload may thus be contained within the interior of the particle, which may thus shelter it from the external environment surrounding the particle (or vice versa). For instance, a drug or other payload contained within a particle administered to a subject will be protected from a subject's body, and the body will also be isolated from the drug. A targeting moiety present on the surface of the particle may allow the particle to become localized at a particular targeting site, for instance, a tumor, a disease site, a tissue, an organ, a type of cell, etc. The drug or other payload may then, in some cases, be released from the particle and allowed to interact locally with the particular targeting site.

Yet another aspect of the invention is directed to polymer particles having more than one polymer or macromolecule present, and libraries involving such polymers or macromolecules. For example, in one set of embodiments, particles may contain more than one distinguishable macromolecule, and the ratios of the two (or more) macromolecules may be independently controlled, which allows for the control of properties of the particle. For instance, a first macromolecule may be a polymeric conjugate comprising a targeting moiety and a biocompatible portion, and a second macromolecule may comprise a biocompatible portion but not contain the targeting moiety, or the second macromolecule may contain a distinguishable biocompatible portion from the first macromolecule. Control of the amounts of these macromolecules within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle may comprise a first macromolecule comprising a poly(ethylene glycol) and a targeting moiety conjugated to the poly(ethylene glycol), and a second macromolecule comprising the poly(ethylene glycol) but not the targeting moiety, or comprising both the poly(ethylene glycol) and the targeting moiety, where the poly(ethylene glycol) of the second macromolecule has a different length (or number of repeat units) than the poly (ethylene glycol) of the first macromolecule. As another example, a particle may comprise a first macromolecule comprising a first biocompatible portion and a targeting moiety, and a second macromolecule comprising a second biocompatible portion different from the first biocompatible portion (e.g., having a different composition, a substantially different number of repeat units, etc.) and the targeting moiety. As yet another example, a first macromolecule may comprise a biocompatible portion and a first targeting moiety, and a second macromolecule may comprise a biocompatible portion and a second targeting moiety different from the first targeting moiety.

Libraries of such particles may also be formed. For example, by varying the ratios of the two (or more) polymers within the particle, libraries of particles may be formed, which may be useful, for example, for screening tests, high-throughput assays, or the like. Entities within the library may vary by properties such as those described above, and in some cases, more than one property of the particles may be varied within the library. Accordingly, one embodiment of the invention is directed to a library of nanoparticles having different ratios of polymers with differing properties. The library may include any suitable ratio(s) of the polymers or macromolecules. For example, in a particle having a first macromolecule and a second macromolecule, the first and second macromolecule may be present in a ratio of 0 to about 5%:1, about 10%:1, about 15%:1, about 20%:1, about 5%1 to about 10%:1, etc.

Another aspect of the present invention is directed to a "payload," or a species (or more than one species) contained within a particle, such as those described above. For instance, the targeting moiety may target or cause the particle to become localized at specific portions within a subject, and the payload may be delivered to those portions. For example, a targeting portion may cause the particles to become localized to a tumor, a disease site, a tissue, an organ, a type of cell, etc. within the body of a subject, depending on the targeting moiety used. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, or the like.

Those of ordinary skill in the art will be identify targeting species specific to a targeting moiety of interest, as previously discussed; for example, PSMA aptamer may become localized to prostate cancer cells. Other examples of payloads include, but are not limited to, nucleic acids such as DNA or RNA (e.g., for RNA interference), peptides or proteins, enzymes, antibodies, carbohydrates, small molecules (e.g., having a molecular weight of less than about 1000 Da), or the like.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. Non-limiting examples of potentially suitable drugs include antimicrobial agents, analgesics, antiinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable medicaments may be selected from contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Specific non-limiting examples of drugs include doxorubicin, mitomycin, cisplatin, daunorubicin, bleomycin, actinomycin D, neocarzinostatin, carboplatin, stratoplatin, Ara-C. Other examples include Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb); Ceclor, Lorabid, Dynabac, Prozac, Darvon, Permax, Zyprexa, Humalog, Axid, Gemzar, Evista (Eli Lily); Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.); Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn); Lopid, Accrupil, Dilantin, Cognex, Neurontin, Loestrin, Dilzem, Fempatch, Estrostep, Rezulin, Lipitor, Omnicef, FemHRT, Suramin, or Clinafloxacin (Warner Lambert).

As another example, if the targeting moiety targets a cancer cell, then the payload may be an anti-cancer drug such as 20-epi-1,25 dihydroxyvitamin D3,4-ipomeanol, 5-ethynyluracil, 9-dihydrotaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedeflngol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambesoidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemeitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine; ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosie acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

Further specific non-limiting examples of drugs that can be included within a particle of the present invention include acebutolol, acetaminophen, acetohydroxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydrase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfuram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecamide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenyloin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulos, methyldopa, methylergonovine, methylphenidate, methylprednisolone, methysergide, metoclopramide, matolazone, metoprolol, metronidazole, minoxidil, mitotane, monamine oxidase inhibitors, nadolol, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystafin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenyloin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyridoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocamide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B12, vitamin C, vitamin D, vitamin E, vitamin K, xanthine, and the like.

In another set of embodiments, the payload is a diagnostic agent. For example, the payload may be a fluorescent molecule; a gas; a metal; a commercially available imaging agents used in positron emissions tomography (PET), computer assisted tomography (CAT), single photon emission computerized tomography, x-ray, fluoroscopy, and magnetic resonance imaging (MRI); or a contrast agents. Non-limiting examples of suitable materials for use as contrast agents in MRI include gadolinium chelates, as well as iron, magnesium, manganese, copper, and chromium. Examples of materials useful for CAT and x-ray imaging include, but are not limited to, iodine-based materials.

As another example, the payload may include a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present invention include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F. The radionucleides may be contained within the particle (e.g., as a separate species), and/or form part of a macromolecule or polymer that forms the particle.

Another aspect of the invention is directed to systems and methods of making such particles. In one set of embodiments, the particles are formed by providing a solution comprising one or more polymers, and contacting the solution with a polymer nonsolvent to produce the particle. The solution may be miscible or immiscible with the polymer nonsolvent. For example, as is discussed in the examples, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles.

Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Once the inventive conjugates have been prepared, they may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

As used herein, the term "pharmaceutically acceptable carrier" means a nontoxic, inert solid, semi-solid or liquid filler, diluent, encapsulating material or formulation auxiliary of any type. Remington's Pharmaceutical Sciences Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives, such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the inventive conjugate with suitable non-irritating excipients or carriers such as cocoa butter, polyethylene glycol, or a suppository wax which are solid at ambient temperature but liquid at body temperature and therefore melt in the rectum or vaginal cavity and release the inventive conjugate.

Dosage forms for topical or transdermal administration of an inventive pharmaceutical composition include ointments, pastes, creams, lotions, gels, powders, solutions, sprays, inhalants, or patches. The inventive conjugate is admixed under sterile conditions with a pharmaceutically acceptable carrier and any needed preservatives or buffers as may be required. Ophthalmic formulations, ear drops, and eye drops are also contemplated as being within the scope of this invention. The ointments, pastes, creams, and gels may contain, in addition to the inventive conjugates of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof. Transdermal patches have the added advantage of providing controlled delivery of a compound to the body. Such dosage forms can be made by dissolving or dispensing the inventive conjugates in a proper medium. Absorption enhancers can also be used to increase the flux of the compound across the skin. The rate can be controlled by either providing a rate controlling membrane or by dispersing the inventive conjugates in a polymer matrix or gel.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

When administered orally, the inventive conjugates can be, but are not necessarily, encapsulated. A variety of suitable encapsulation systems are known in the art ("Microcapsules and Nanoparticles in Medicine and Pharmacy," Edited by Doubrow, M., CRC Press, Boca Raton, 1992; Mathiowitz and Langer J. Control. Release 5:13, 1987; Mathiowitz et al. Reactive Polymers 6:275, 1987; Mathiowitz et al. J. Appl. Polymer Sci. 35:755, 1988; Langer Acc. Chem. Res. 33:94, 2000; Langer J. Control. Release 62:7, 1999; Uhrich et al. Chem. Rev. 99:3181, 1999; Zhou et al. J. Control. Release 75:27, 2001; and Hanes et al. Pharm. Biotechnol. 6:389, 1995). The inventive conjugates may be encapsulated within biodegradable polymeric microspheres or liposomes. Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and other biodegradable polyesters. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain embodiments, the adjuvant stimulates the immune response. Any adjuvant may be used in accordance with the present invention. A large number of adjuvant compounds is known in the art (Allison Dev. Biol. Stand. 92:3-11, 1998; Unkeless et al. Annu. Rev. Immunol. 6:251-281, 1998; and Phillips et al. Vaccine 10:151-158, 1992).

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

It will be appreciated that the exact dosage of the inventive conjugate is chosen by the individual physician in view of the patient to be treated. In general, dosage and administration are adjusted to provide an effective amount of the inventive conjugate to the patient being treated. As used herein, the "effective amount" of an inventive conjugate refers to the amount necessary to elicit the desired biological response. As will be appreciated by those of ordinary skill in this art, the effective amount of inventive conjugate may vary depending on such factors as the desired biological endpoint, the drug to be delivered, the target tissue, the route of administration, etc. For example, the effective amount of inventive conjugate containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The conjugates of the invention may be formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions of the present invention will be decided by the attending physician within the scope of sound medical judgment. For any conjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

The present invention also provides any of the above-mentioned compositions in kits, optionally with instructions for administering any of the compositions described herein by any suitable technique as previously described, for example, orally, intravenously, pump or implantable delivery device, or via another known route of drug delivery. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the conjugate and the mode of use or administration. Suitable solvents for drug compositions are well known, for example as previously described, and are available in the literature. The solvent will depend on the conjugate and the mode of use or administration.

The invention also involves, in another aspect, promotion of the administration of any of the conjugates described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

The following examples are intended to illustrate certain embodiments of the present invention, but do not exemplify the full scope of the invention.

Example 1

This example illustrates polymer synthesis of a triblock polymer according to one embodiment of the invention. Carboxylic end modified high molecular weight PLGA (with inherent viscosity of 0.6 dL/g in HFIP, hexafluoro-2-propanol) was purchased from Absorbable Polymers International. Bifunctional PEG ($NH_2$—PEG-COOH) was purchased from Nektar Therapeutics. Amine modified PSMA aptamer was purchased from RNA-Tec NV (Leuven, Belgium). All other reagents were purchased from Sigma Aldrich.

The conjugation of PLGA and PEG were achieved in the presence of EDC and NHS. Briefly, PLGA particles were dissolved in acetonitrile. The carboxylic end of PLGA was activated by mixing with NHS and EDC at a molar ratio of COOH to EDC and NHS and stirred overnight at room temperature. The excess EDC and NHS in the solution were quenched by adding 2-mercaptoethanol. The NHS activated PLGA was purified by precipitation in a solution containing ethyl ether and methanol, and followed by centrifugation at 3000 g for 10 minutes. To conjugate the amine end of $NH_2$—PEG-COOH with the NHS-activated PLGA, both polymers mixed at a molar ratio of 1:1.3 (PLGA-NHS: $NH_2$—PEG-COOH) at room temperature overnight. The resulting PLGA-PEG-COOH copolymer was purified by precipitation in ethyl ether-methanol solution.

To make PLGA-PEG-aptamer triblock copolymer, PLGA-PEG copolymers were first dissolved in acetonitrile, and aptamers were dissolved in DMSO (dimethylsuloxide) and formamide. The conjugation of the carboxylic end of COOH-PEG-PLGA and the amine end of aptamer was done using the same EDC/NHS reaction as described for the PLGA-PEG conjugation reaction.

The nanoparticles were formed by precipitating the triblock copolymer in water. Briefly, the triblock polymer was dissolved in acetonitrile at a concentration between 1 to 50 mg/mL, and then added drop by drop in water. The nanoparticles formed instantly upon mixing. The residual acetonitrile in the suspension was evaporated by continuously stirring the suspension at room temperature for 4 hours, followed by washing and rinsing the nanoparticles using ultracentrifugation.

Example 2

This example illustrates the synthesis of a multi-block polymer for the development of small scale particles (i.e. pico, nano or microparticles) that have a predetermined functionalized surface for applications such as targeting certain cells, tissues, or organs of the body; and may have the ability of minimizing host immunogenicity by the presence of "stealth" materials on the particle surface which may be a part of the multi-block copolymer; and may have the ability of releasing pharmaceutical drugs at a sustained rate. These small particles may have utility as research tools or for clinical applications for targeting certain cells, tissues, or organs for diagnostic, therapeutic, or a combination of diagnostic and therapeutic applications. This example also shows the pre-functionalization of the polymer by a biomacromolecule block before nanoparticle formulation.

This example illustrates a technology platform for synthesizing multi-block polymer that can be used for formulating functionalized particle drug delivery system with unique abilities such as targeting. The multi-block polymer includes a unique targeting molecule that can bind to its specific receptor, and a biodegradable polymeric material that can release bioactive drugs at a sustained rate upon administration; and may also include a third utility, i.e., a "stealth" material that can minimize the host immunogenicity and/or increase the circulation half-life. Additional molecules can be integrated into the block such as fluorescent agents to develop targeted fluorescent particles for combined imaging and therapeutic applications. The particles may be generated at a nanoscale size by precipitation of the multi-block copolymer in an aqueous medium. Taking advantage of the differences in hydrophilicity and hydrophobicity of the distinct polymers within the multi-block co-polymer system, nanoparticles can be synthesized that can encapsulate a drug in the hydrophobic component of the multi-block system forming the core of the nanoparticle, while the hydrophilic targeting biomacromolecule polymer, such as polynucleotides (i.e. aptamers) or polypeptides, with or without a polyalkylene glycol polymer will be present on the surface of the nanoparticle, resulting in a single step synthesis or targeted nanoparticles.

Such nanoparticles can reach their targets after skin, subcutaneous, mucosal, intramuscular, ocular, systemic, oral, or pulmonary administration. The target tissue may represent generalized systemic absorption or more specifically, targeting of particles to distinct cells, tissues, or organs of the body. One specific use of such targeted nanoparticles may be in the field of cancer. It is possible to achieve specific and efficient tumor specific targeting by systemic administration of multi-block polymers containing targeting molecules that are directed against epitopes or antigens present on tumor cells. The success of this approach may depend on the prospect of high throughput synthesis of cancer targeted nanoparticles. By developing libraries of particles with distinct but overlapping biophysical and/or chemical characteristics, as shown in this example, nanoparticles with high cancer cell target specificity can be screened with desired anti-cancer drug release kinetics. Thus, the multi-block polymer synthesis platform discussed in this example enables the targeted molecules to conjugate with stealth and drug release polymers, and subsequently forms the desired nanoparticles to a one step reaction under ambient condition.

This example describes a platform technology that enables conjugation of targeted ligand onto a biodegradable polymer and formation of functionalized nanoparticles in as few as a one-step reaction. The composition of the nanoparticle and its surface property can be accurately quantified. The potential implication of this invention is broadly important to the field of nanotechnology and cancer. Further, this example relates to multi-block copolymers and at least one component of the multi-block may be a biomacromolecule for targeted delivery, such as polynucleotide or polypeptide. This example describes the synthesis of a multi-block copolymer system for rapid synthesis of particles which may be targeted with polypeptides or polynucleotides (i.e. aptamers).

The synthesis of a multi-block polymer is initiated by conjugation of functionalized biodegradable polyesters with chemical groups such as, but not limited to, malimide or carboxylic acid for easy conjugation to one end of thiol, amine or similarly functionalized polyethers. The conjugation of polymer esters and polyethers will be performed in organic solvents such as but not limited to dichloromethane, acetonitrile, chloroform, dimethylformamide, tetrahydrofuran, and acetone. The other free end of the polyether would be functionalized with chemical groups for conjugation to a library of targeting molecules such as but limited to polymer of nucleic acids, fatty acids, peptides, carbohydrates, peptidoglycans, or glycopeptides. The polynucleotides may contain unique RNA, DNA, or modified RNA or DNA fragments which are generated using natural nucleotides or nucleotides having a substitution of a functional group including but not limited to 2'-F, 2'-OCH$_3$, 2'-NH$_3$; or polynucleotides generated using L-enantiomeric nucleotides. The conjugation reaction between the targeting molecules and the poly-ester-ether copolymer is achieved by adding the targeted molecules solubilized in an organic solvent such as but not limited to formamide, dimethylformamide, pyridines, dioxane, and dimethysulfoxide, to a solution of Copolymer of poly(ester-ether) in the solvents described above. Following each of the two conjugation reactions, unconjugated macromers are washed away by precipitating the polymer of interest in solvents such as but not limited to ethyl ether, hexane, methanol and ethanol. Biodegradable and biocompatible polymer poly(lactide-co-glycolide) (PLGA) and polyethylene glycol (PEG) can be used as a model for the block copolymer of poly(ester-ether). In one example, a nuclease-stable oligonucleotide can be used for prostate specific membrane antigen (PSMA) aptamer as the targeting molecule to prostate cancer cells. Carboxylic acid modified PLGA (PLGA-COOH) can be conjugated to the amine modified heterobifunctional PEG (NH$_2$—PEG-COOH) and form a copolymer of PLGA-PEG-COOH. By using an amine modified PSMA aptamer (NH$_2$-Aptamer), a triblock polymer of PLGA-PEG-Aptamer can be obtained by conjugating the carboxylic acid end of PEG and amine functional group on the aptamer. The multiblock polymer can also be useful for imaging and diagnostic applications. In such embodiment, a photo-sensitive or environmental-responsible compound will be linked to the multiblock polymer.

The targeted nanoparticles are formed by precipitation of the multi-block polymer in an aqueous environment, in this example. The nanoparticle formulation system described here is compatible with high throughput biological assays in order to test the nanoparticles generated from the multi-block polymer. It is possible to perform high throughput assays to determine cellular update of nanoparticles with different surface properties in vivo. For an example, a combinatorial method could be used by changing the composition of the multi-block polymer and its mixing ratio in the nanoparticle formulation and thereby generating a library of distinct formulations of pegylated nanoparticle-aptamer bioconjugates: nanoparticle size (by varying the molecular weight of PEG in the multiblock polymer), surface charge (by mixing the multiblock polymer formulation with PEG polymer with a terminal carboxylic acid group COOH-PEG-PLGA), surface hydrophilicity (by mixing multiblock polymer with linear or branched PEG polymers of various molecular weight, and/or density of aptamers on nanoparticle surface (by controlling the mixing ratios of multiblock polymer and methoxy modified PEG (mPEG-PLGA) or carboxylic acid modified PEG (PLGA-PEG-COOH) which can be conjugated to NH$_2$-modified aptamers)). This example of the multi-block copolymer allows for a rapid and reproducible synthesis of a library of nanoparticles for further evaluation and characterization.

Example 3

Figure 9A:
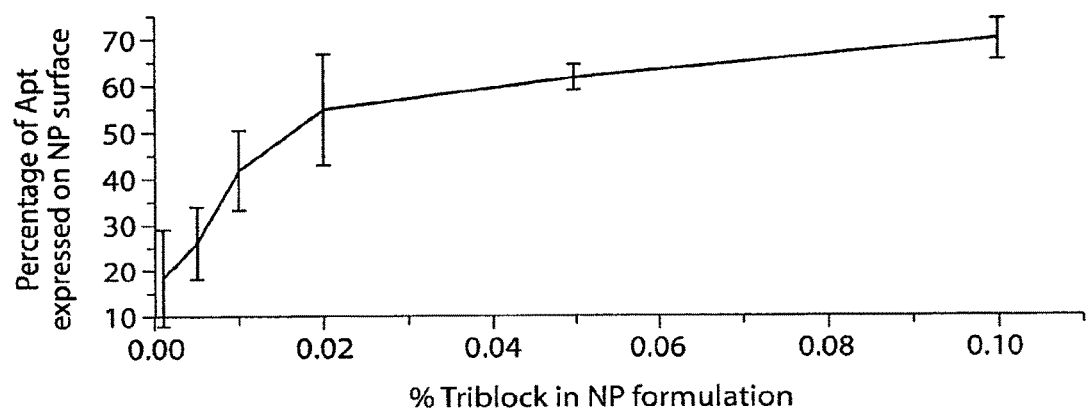
FIGS. 9A-9B illustrate the determination of the amount of aptamer on the nanoparticle surfaces, in still another embodiment of the invention.
Figure 9B:
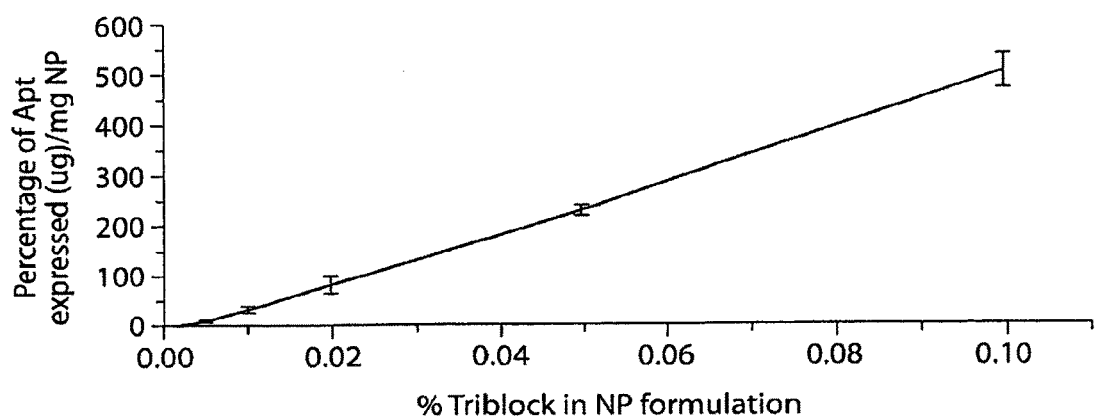

This example illustrates determination of the amount of aptamer expressed on the nanoparticle surfaces. To demonstrate that a library of nanoparticles containing different ligand densities on the nanoparticle surface can be formulated by diluting the aptamer-PEG-PLGA triblock of Example 1 with diblock solution, the triblock copolymer was serially diluted in PLGA-PEG diblock copolymer then precipitated in water. To quantify the A10 aptamer ligand density on the nanoparticle surface, the amide bond between the A10 aptamer and the carboxyl functional group of PEG remained on the nanoparticle surface was hydrolyzed in base, and the amount of RNA aptamer recovered was quantified spectrophotometrically. It was found that increasing the aptamer triblock in the nanoparticle formulation linearly increased the amount of aptamer recovered from the nanoparticle surface. For example, increasing the aptamer triblock to diblock ratio from 0.02 to 0.10, the amount aptamer on the nanoparticle surface increased from 100 micrograms to 450 micrograms. By comparing the amount of aptamer ligand recovered from the nanoparticle surface with the total amount of aptamers present in the NP formulation, it was found that increasing aptamer triblock formulation increased the total proportion of aptamer that can be expressed on the NP surface. By combining FIGS. 9A and 9B with the in vitro and in vivo uptake study, the amount of ligand surface density can be precisely controlled for the desired therapeutic application. For example, based on the in vitro nanoparticle uptake study and the in vivo study, it was found that the 2% triblock formulation was sufficient to target LNCap prostate cancer tumors with minimal amount of nonspecific uptake. Using FIGS. 9A and 9B, it was determined that about 50% of the aptamer in the 2% formulation was expressed on the nanoparticle surface, which translates to approximately 100 micrograms of aptamer per mg of aptamer.

The nanoparticles were prepared as follows. Nanoparticles containing different amount of aptamer-PEG-PLGA triblock copolymer and PLGA-PEG copolymer was precipitated in water. The aptamers on the surface of the nanoparticles were hydrolyzed from the nanoparticles were separated from the nanoparticles by ultracentrifugation. Briefly, the nanoparticles were incubated in 10 mM KOH at 60° C. for 30 minutes. The nanoparticle size before and after base treatment was monitored by light scattering. It was found that the nanoparticle diameter after the treatment decreased by 6-8 nm. The aptamers removed from the nanoparticles surface were separated from the nanoparticle core by ultra-centrifugation. The mass of the aptamers collected was determined spetrophotometrically at UV absorbance at 260 nm. The percentage of aptamer expressed on the nanoparticles surface was determined by the amount of aptamer separated from the NP surface divided by the total amount of aptamers triblock copolymer used in the NP formulation.

Example 4

In this example, a well-characterized nanoparticle formulation is illustrated with physicochemical properties, drug release kinetics and stability characteristics suitable for use in the clinic. Here, a chemotherapeutic drug encapsulated biodegradable nanoparticles is shown. The composition of the targeted nanoparticles is made of the following four components: poly(lactic-co-glycolic acid) (PLGA), an FDA approved controlled release polymer system that can encapsulate a drug and release it over time (properties that can be mediated by both drug diffusion and polymer degradation); poly(ethylene glycol) (PEG), an FDA approved polymer that can increase the circulating half-life of nanoparticles; the drug docetaxel (Dtxl), an FDA approved chemotherapeutic that is widely used in clinical practice; and a 56 base pair A10 2'-fluoropyrimidine nuclease stabilized RNA aptamer (referred to as Aptamer) that can bind with high affinity and specificity to Prostate Specific Membrane Antigen (PSMA), which is significantly up-regulated on the surface of PCa cells and on many tumor microvasculatures, and is recycled from cell surface at a basal rate, allowing for the uptake of nanoparticle-aptamer bioconjugates into the target cells.

In this example, the PLGA segment on the triblock copolymer serves as the biodegradable matrix used to encapsulate drugs; the PEG segment provides an attachment point while also enhances circulating half-life; and the A10 aptamer segment represents the PSMA specific targeting molecule. A PLGA-PEG-Apt triblock copolymer was synthesized which can self assemble in water to form drug encapsulated nanoparticles with functionalized molecules on the surface of nanoparticles. Thus, an aptamer-PEG-PLGA triblock copolymer system that enables conjugation of aptamers directly onto the PLGA-PEG diblock copolymer before nanoparticle formation is illustrated. The PLGA segment on the triblock copolymer serves as the biodegradable drug delivery matrix that can be used to encapsulate the drugs to be released at the targeted site; the PSMA aptamer segment represents the PSMA specific targeting molecule; and the PEG enhances circulating half-life by minimizing passive non-specific uptake of particles. This technology of making an aptamer-PEG-PLGA triblock copolymer can be used as a platform technology is potentially suited to develop large scale production of prefunctionalized nanoparticles while minimizing production time and the nanoparticle batch to batch variation observed in the post-particle surface modification. Another advantage of the making targeted nanoparticles using triblock copolymer is to enable high throughput synthesis of a large batch of prefunctionalized nanoparticles with different surface and chemical properties by simply mixing the triblock copolymer with other polymers containing the desired properties.

Figure 10:
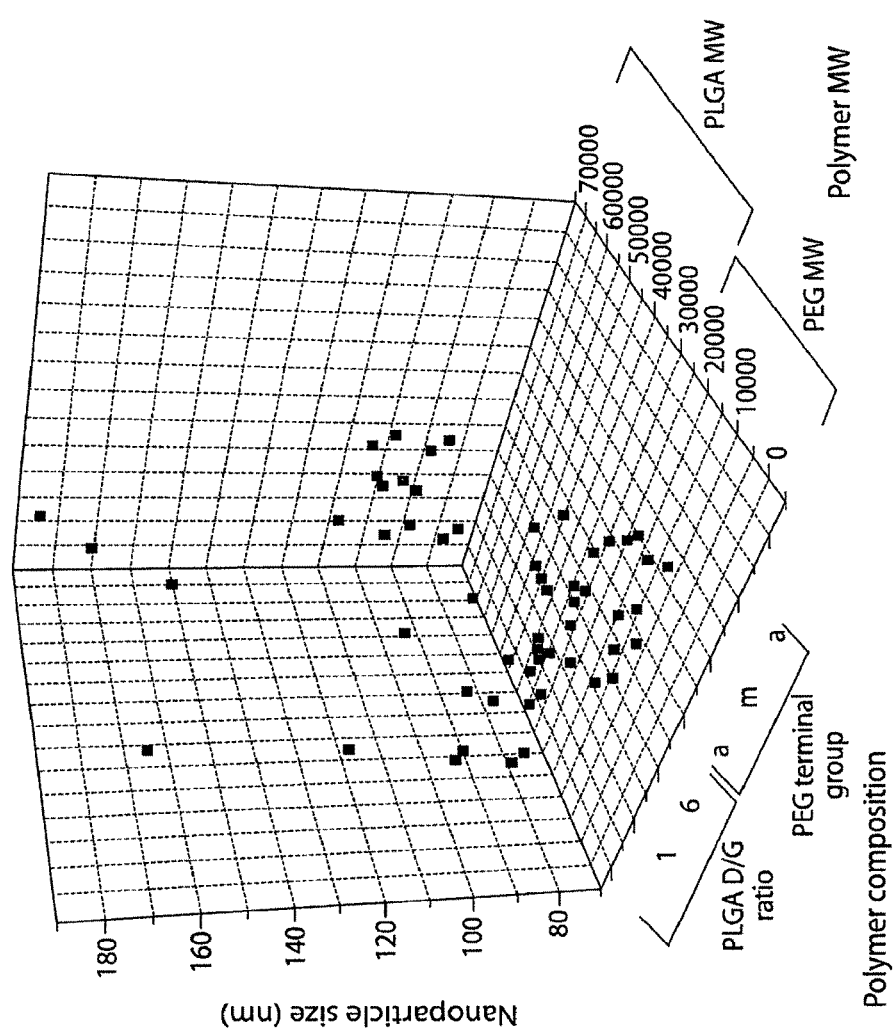
FIG. 10 illustrates the relationship between nanoparticle size and molecular weight, in another embodiment of the invention.
Figure 11A:
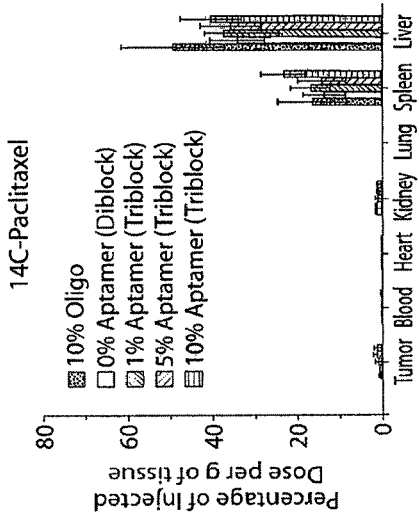
FIGS. 11A-11D in vitro targeting of aptamer-containing nanoparticles, according to still another embodiment of the invention.
Figure 11B:
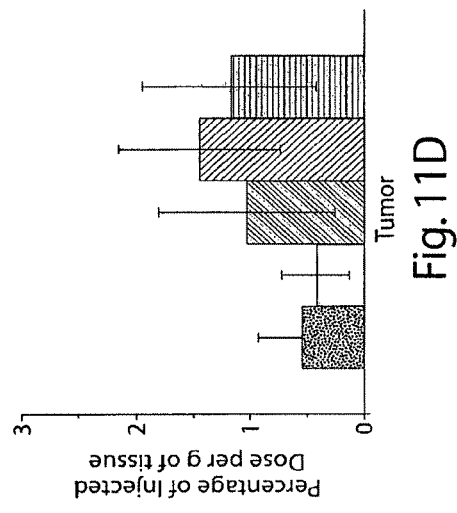
Figure 11C:
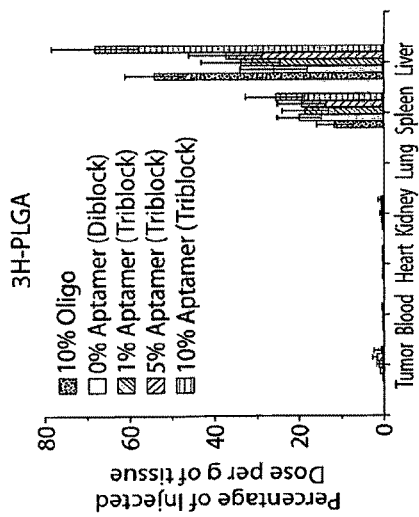
Figure 11D:
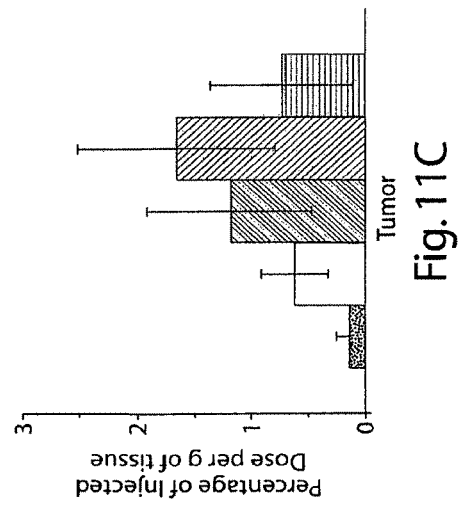

Here, a library of nanoparticles with hydrodynamic radius was generated by using different compositions of PLGA-PEG diblock copolymer. As shown in the 3D plot in FIG. 10, the nanoparticle size was directly proportional to the PLGA-PEG molecular weight, whereby increasing the PLGA and/or PEG molecular weight increased the size of nanoparticles. The nanoparticle size was more sensitive to PLGA molecular weight than to PEG. The functional group on the PLGA and PEG terminal end had no influence on the nanoparticle size. Based on this plot, appropriate types of PLGA-PEG copolymer can be chosen for mixing with aptamer triblock copolymer to generate nanoparticles with different particle size.

Details of the synthesis process are as follows. Carboxylic end modified high molecular weight PLGA (with inherent viscosity of 0.6 dL/g in HFIP) was purchased from Absorbable Polymers International. Bifunctional PEG ($NH_2$—PEG-COOH) was purchased from Nektar Therapeutics. Amine modified PSMA aptamer was purchased from RNA-Tec NV (Leuven, Belgium). All other reagents were purchased from Sigma Aldrich.

The conjugation of PLGA and PEG were achieved in the presence of EDC and NHS. Briefly, PLGA particles were dissolved in acetonitrile. The carboxylic end of PLGA was activated by mixing with NHS and EDC at a molar ratio of COOH to EDC and NHS and stir overnight at room temperature. The excess EDC and NHS in the solution were quenched by adding 2-mercaptoethanol. The NHS activated PLGA was purified by precipitation in a solution containing ethyl ether and methanol, and followed by centrifugation at 3000 g for 10 minutes. To conjugate the amine end of $NH_2$-PEG-COOH with the NHS-activated PLGA, both polymers mixed at a molar ratio of 1:1.3 (PLGA-NHS: $NH_2$—PEO-COOH) at room temperature overnight. The resulting PLGA-PEG-COOH copolymer was purified by precipitation in ethyl ether-methanol solution. To make PLGA-PEG-aptamer triblock copolymer, PLGA-PEG copolymers were first dissolved in acetonitrile, and aptamers were dissolved in dimethylsulfoxide and formamide. The conjugation of the carboxylic end of COOH-PEG-PLGA and the amine end of aptamer was done using the same EDC/NHS reaction as described for the PLGA-PEG conjugation reaction.

Nanoparticles were formed by precipitating the copolymer in water. Briefly, the triblock polymer was dissolved in acetonitrile at a concentration between 1 to 50 mg/mL, and then added drop by drop in water. The nanoparticles formed instantly upon mixing. The residual acetonitrile in the suspension was evaporated by continuously stirring the suspension at room temperature for 4 hrs, followed by washing and rinsing the nanoparticles by ultracentrifugation. To encapsulate chemotherapeutic drugs into the nanoparticle core, triblock copolymer was mixed with hydrophobic chemotherapeutic drugs such as docetaxel and paclitaxel, and then precipitated in water followed by the same purification steps as described above.

Example 5

Figure 7A:
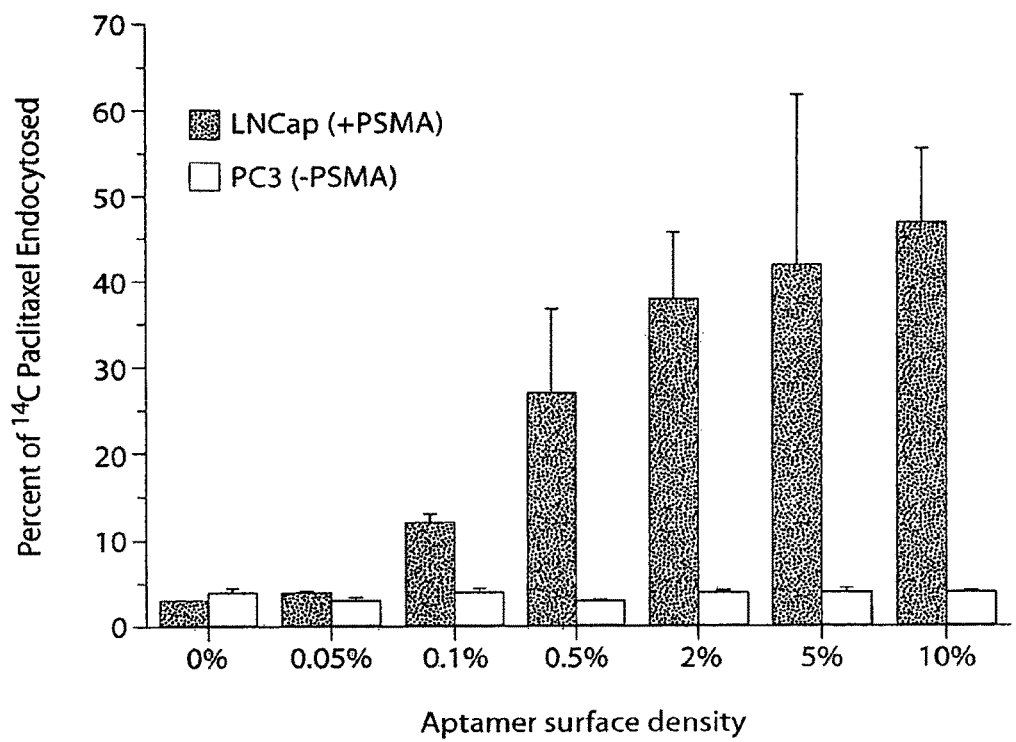
FIGS. 7A-7B illustrate in vitro activity of an aptamer-containing nanoparticle, produced in still another embodiment of the invention.
Figure 7B:
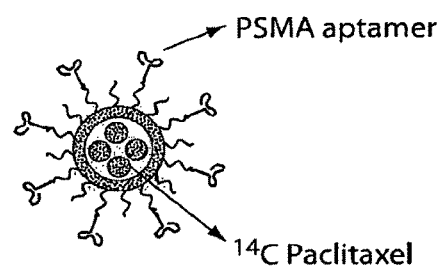

This example demonstrates that binding of PEGylated aptamer-nanoparticle bioconjugates to LNCaP cells was significantly enhanced when compared to control pegylated nanoparticles lacking the A10 aptamer (FIG. 7). Targeted nanoparticles were formulated by mixing the aptamer triblock copolymer with different amount of PLGA-PEG diblock copolymer (FIG. 4A). Nanoparticles were coencapsulated with $^{14}C$-radiolabelled paclitaxel. The percentage of nanoparticles endocytosed by the PCa cells was quantified by the amount of radioactivity of 14C detected in the cells. In the case of PC3 prostate epithelial cells, which do not express the PSMA protein, no measurable difference in binding was observed between the bioconjugate and the control group (FIG. 11).

In LNCaP cells, which do express PSMA protein, the data demonstrates significant enhancement in the binding of targeted nanoparticles vs. the non-targeted nanoparticles in LNCaP cells. A notable observation was a remarkably low binding efficiency of nanoparticles in non-targeted nanoparticles to both PC3 and LNCaP cells, presumably attributed to the presence of PEG group. Additionally, this example also showed that nanoparticles developed from tri-block copolymer using random nucleic acid molecules failed to have any targeting effect and behaved similar to the non-targeted nanoparticles.

FIG. 7 shows the effect of aptamer concentration on the nanoparticle surface on the rate of nanoparticle endocytosis by the PCa cells in vitro. LNCaP cells (which express the PSMA protein; left bars) and PC3 cells (which do not express PSMA; right bars) were grown in 6 well tissue culture plates in the presence of nanoparticles with different aptamer concentration on their surface. Each formulation was obtained by mixing PLGA-PEG-aptamer triblock with different amount of PLGA-PEG diblock copolymer prior to particle formation. The PSMA cell specific uptake was quantified after 4 hours using nanoparticles which had Dtxl and trace amount of $^{14}C$-paclitaxel encapsulated within them (note that $^{14}C$-Dtxl is not commercially available and vehicle optimization was carried out with trace $^{14}C$-paclitaxel together with Dtxl) (n=5). The data was significant in that with as little as 0.1% triblock in the formulation of nanoparticles we begin seeing targeting effects, and this targeting effect was largely plateaued after using 5% triblock in the formulation. Additional use of triblock after this point results in the masking of the PEG on the nanoparticle surface which can accelerate clearance of particles and make the particles less "stealth."

In this example, to demonstrate the cellular uptake of triblock nanoparticles was aptamer mediated, nanoparticles made with various proportion of triblock copolymer were seeded onto LNCap (PSMA+) and PC3 (PSMA−) cells. Briefly, 500,000 LNCap and PC3 cells were seeded to a 6-well tissue culture plate and incubated at 37° C. overnight. Nanoparticles with different concentrations of aptamers on the particle surface were formulated by diluting aptamer triblock copolymers with PLGA-PEG diblock copolymer. The nanoparticles were coencapsulated with docetaxel and $^{14}C$ radiolabelled paclitaxel. The percentage of nanoparticles endocytosed by the PCa cells was quantified by the amount of radioactivity of $^{14}C$ detected in the cells. The controls were nanoparticles made without aptamer triblock copolymer, and nanoparticles made using a nontargeting DNA triblock copolymer. The nanoparticle formulations were seeded onto LNCaP cells and PC3 cells for two hours at 37° C. The cells were then rinsed 3× with PBS to remove unbound nanoparticles from the culture media. To quantify nanoparticle uptake, cells were trypsinized and collected in a glass vial containing scintillation cocktail. The amount of radioactivity in the cells collected were detected by using a TriCarb scintillation counter.

Example 6

This example shows in vivo targeting LNCap tumor cells in mice. Human xenograft prostate cancer tumors were induced in 8-week old balb/c nude mice (Charles River Laboratories, Wilmington, Mass., USA). Mice were injected subcutaneously in the right flank with 4 million LNCaP cells suspended in a 1:1 mixture of media and matrigel (BD Biosciences, Franklin Lakes, N.J., USA). Prior to use in tumor induction, LNCaP cells were cultured in RPMI-1640 medium supplemented with 10% fetal bovine serum, 100 units/mL penicillin 0, and 100 mg/mL streptomycin. Tumor targeting studies were carried out after the mice developed 100 mg tumors. 20 mice were randomly divided into groups of four (5% aptamer triblock nanoparticles, 2% aptamer triblock nanoparticles, 5% nonfunctional DNA triblock, nanoparticles without triblocks). For intratumoral injections, mice were anesthesized by intraperitoneal injection of avertin (200 mg/kg body weight), and dosed with different nanoparticle formulations intratumorally. For systemic administrations, nanoparticles were administered by retroorbital injection. The nanoparticles were traced by encapsulating $^{14}C$-paclitaxel prior to administration. Different groups were euthanized at 24 h, and 200 mL of blood was drawn by cardiac puncture from each mouse. The tumor, heart, lungs, liver, spleen and kidneys were harvested from each animal. The $^{14}C$ content of tissues was assayed in a Packard Tri-Garb Scintillation Analyser (Downers Grove, Ill., USA). The tissues were solubilized in Solvable (Packard), and activity was counted in Hionic-Fluor scintillation cocktail (PerkinElmer, Boston, Mass., USA). The liver from each mouse was homogenized due to its large size, and 100 mg of tissue was placed in a scintillation vial for analysis. The other organs were placed directly in scintillation vials. Each organ was solubilized in 2 mL solvent for 12 h at 60° C., and the resulting solution was de-colored with 200 mL hydrogen peroxide for 1 h at 60° C. For the blood, 400 mL Solvable was added, and the vials were otherwise treated similarly to the tissues. To determine 100% dose, vials of the formulated nanoparticles were counted along with the tissues. Data is presented as percent injected dose per gram of tissue.

Figure 8A:
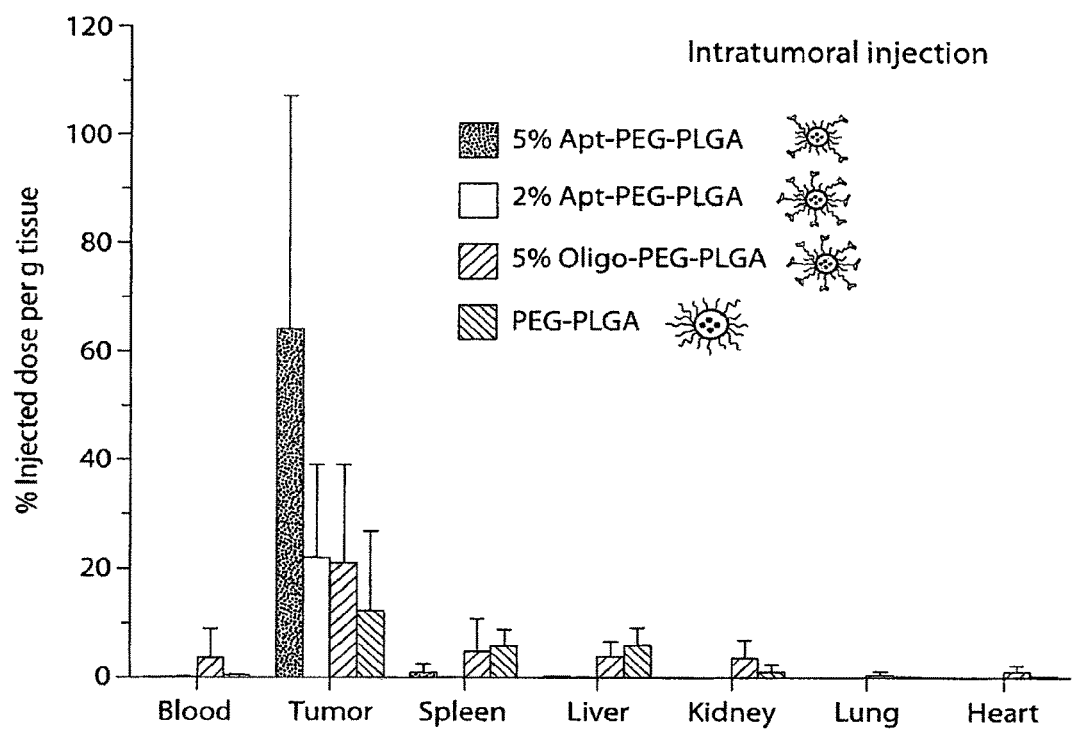
Figure 8B:
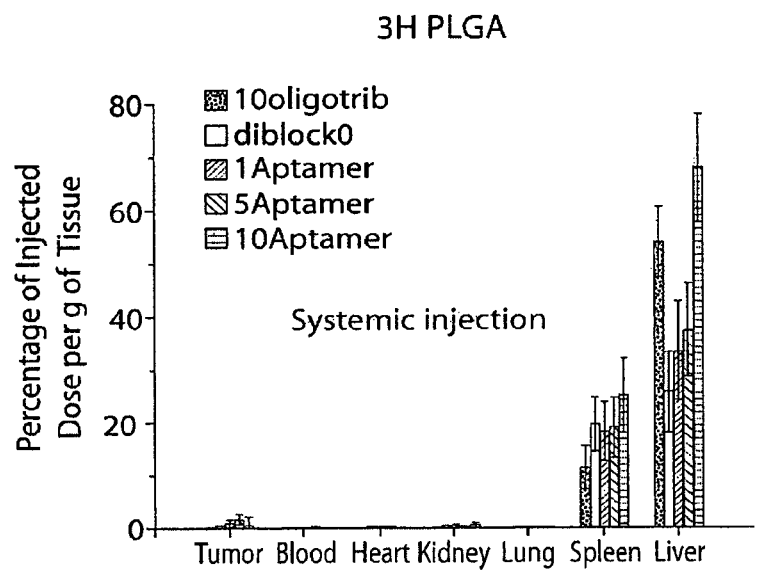
Figure 8C:
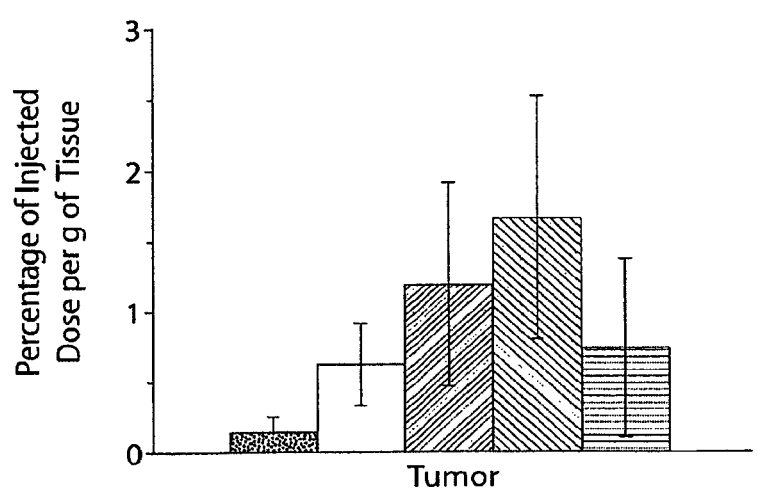

As can be seen in FIG. 8A, the nanoparticles were highly targeted to the tumor in these mice with intratumoral injunction, although less targeting was seen with systemic injection (FIG. 8B). FIG. 8C shows the percentage of injected dose per gram of tissue as a function of aptamer formulation.

Referring now to FIG. 11, to examine to effect of aptamer surface density on targeting prostate cancer tumor in vivo, a biodistribution study using radiolabelled nanoparticles was conducted. The nanoparticle formulation was carried out according to the FIG. 2B of the embodiment scheme slides. Briefly, aptamer triblock was premixed with $^3H$ radiolabelled PLGA (component A in FIG. 3B), and $^{14}C$ radiolabelled paclitaxel (lipophilic drug). The radiolabelled PLGA and paclitaxel were used to trace the biodistributions of the particles and the drugs, respectively. Systemic administration of targeted nanoparticles with varying concentration of triblock confirmed that maximal targeting of nanoparticles was achieved with the 5% tri-block nanoparticle formulation. Similar experiments performed with higher concentration of the tri-block copolymer demonstrated a decrease in tumor targeting as these particles are more susceptible to early clearance presumably secondary to excessive masking of the PEG layer on nanoparticle surface. Additionally, in other experiments where nanoparticles were developed from tri-block copolymer using random nucleic acid molecules, these failed to have any targeting effect and behaved similar to non-targeted nanoparticles in vivo. Another important finding was that increasing the aptamer ligand expression on the nanoparticle surface increased nanoparticle liver retention. This finding suggested that the aptamer ligand density on the nanoparticle surface must be precisely controlled in order to achieve tumor specific targeting while ensuring the nanoparticle surface has enough stealth coating to bypass liver filtration.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of making particles, comprising:
providing a solution comprising
  (i) a first population of an amphiphilic macromolecule comprising a biocompatible hydrophobic polymer at one end and a biocompatible hydrophilic polymer at the other end, and
  (ii) a second population of a second macromolecule comprising a biocompatible hydrophobic polymer;
wherein one or more of the first or second macromolecule further comprises a moiety selected from the group consisting of a targeting moiety, an imaging moiety, a chelating moiety, a moiety having multiple charge groups, and a therapeutic moiety; and
contacting the solution with a polymer nonsolvent for the macromolecules under conditions wherein the macromolecules orient to form particles having hydrophobic polymer ends of the amphiphilic macromolecule on the inside of the particles and hydrophilic polymer ends of the amphiphilic macromolecules on the surface of the particles,
wherein the ratio between the first population of the amphiphilic macromolecule and the second population of the second macromolecule is controlled to form particles with a specific surface density of moieties.

2. The method of claim 1, wherein the particles are nanoparticles.

3. The method of claim 1, wherein one or more of the first or second macromolecule comprises an antigenic moiety.

4. The method of claim 1, further comprising adding a therapeutic, prophylactic, or diagnostic agent prior to forming the particles so that the agent is encapsulated within the particles.

5. The method of claim 1, wherein the hydrophobic polymers of the amphiphilic macromolecule and the second macromolecule have a different molecular structure.

6. The method of claim 1, wherein the hydrophobic polymers of the amphiphilic macromolecule and the second macromolecule have the same molecular structure.

7. The method of claim 5, wherein the hydrophobic polymers of the amphiphilic macromolecule and the second macromolecule comprise a polyester.

8. The method of claim 6, wherein the hydrophobic polymers of the amphiphilic macromolecule and the second macromolecule comprise a polyester.

9. The method of claim 8, wherein the hydrophilic polymer of the amphiphilic macromolecule comprises a poly(alkylene glycol).

10. The method of claim 9, wherein the polyester is selected from the group consisting of poly(lactide-co-glycolide), poly(lactide), and poly(glycolide).

11. The method of claim 10, wherein the poly(alkylene glycol) is poly(ethylene glycol).

12. The method of claim 4, wherein the agent is an immunosuppressive agent.

* * * * *

SEQUENCE LISTING

```
<160> NUMBER OF SEQ ID NOS: 1

<210> SEQ ID NO 1
<211> LENGTH: 56
<212> TYPE: RNA
<213> ORGANISM: Artificial Sequence
<220> FEATURE:
<223> OTHER INFORMATION: Aptamer

<400> SEQUENCE: 1
gggaggacga ugcggaucag ccauguuuac gucacuccuu gucaauccuc aucggc         56
```